US010596206B1

(12) United States Patent
Sonnenberg et al.

(10) Patent No.: US 10,596,206 B1
(45) Date of Patent: Mar. 24, 2020

(54) PROBIOTIC COMPOSITIONS AND METHODS OF USE

(71) Applicant: Cornell University, Ithaca, NY (US)

(72) Inventors: Gregory F. Sonnenberg, New York, NY (US); Nicholas J. Bessman, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/921,357

(22) Filed: Mar. 14, 2018

Related U.S. Application Data

(60) Provisional application No. 62/471,041, filed on Mar. 14, 2017.

(51) Int. Cl.
| | |
|---|---|
| A61K 35/741 | (2015.01) |
| A61K 38/20 | (2006.01) |
| A61K 35/00 | (2006.01) |
| A61P 1/00 | (2006.01) |
| A61K 35/15 | (2015.01) |
| A61K 38/22 | (2006.01) |

(52) U.S. Cl.
CPC ............ *A61K 35/741* (2013.01); *A61K 35/15* (2013.01); *A61K 38/20* (2013.01); *A61K 38/2066* (2013.01); *A61K 38/22* (2013.01); *A61P 1/00* (2018.01); *A61K 2035/115* (2013.01)

(58) Field of Classification Search
CPC .... A61K 35/741; A61K 35/742; A61K 35/74; A61K 35/744; A61K 35/745; A61K 35/747; A61K 9/0053; A61K 35/37; A61K 45/06; A61K 9/48; A61K 9/4816; A61K 2035/115; A61K 31/7004; A61K 31/7016; A61K 31/715; A61K 35/39; A61K 38/46; A61K 9/0031; A61K 9/19; Y02A 50/473; Y02A 50/402; Y02A 50/469; Y02A 50/475; Y02A 50/478; Y02A 50/48; Y02A 50/481; Y02A 50/49; Y02A 50/401; Y02A 50/414; C12N 1/20; C12Q 1/04; C12Q 1/689; G01N 33/56911
See application file for complete search history.

(56) References Cited

U.S. PATENT DOCUMENTS

| | | | |
|---|---|---|---|
| 6,500,423 | B2 | 12/2002 | Olshenitsky et al. |
| 7,927,584 | B2 | 4/2011 | Allende |
| 8,206,726 | B2 | 6/2012 | Kasper et al. |
| 9,649,345 | B2 | 5/2017 | Honda et al. |
| 2012/0258135 | A1* | 10/2012 | Gunn ............... A61K 39/0008 424/206.1 |
| 2014/0328896 | A1 | 11/2014 | Jewll et al. |
| 2015/0224152 | A1 | 8/2015 | Littman et al. |
| 2016/0022592 | A1 | 1/2016 | Kabadi et al. |
| 2016/0193258 | A1 | 7/2016 | Berry et al. |
| 2016/0250312 | A1* | 9/2016 | Longley ............... A61K 39/015 424/199.1 |
| 2017/0281695 | A1 | 10/2017 | Gantz et al. |

FOREIGN PATENT DOCUMENTS

| | | |
|---|---|---|
| WO | 2017/035526 A1 | 3/2017 |
| WO | 2017/160711 A1 | 9/2017 |

OTHER PUBLICATIONS

Kaur et al. Cellular and Molecular Immunology 12: 96-106, 2015.*
Ronacher et al. Front. Immunol. 9: Article 2209, pp. 1-7, Sep. 25, 2018.*
Chow et al., Host-Bacterial Symbiosis in Health and Disease, Advances in Immunology, vol. 107, chpt. 8, 2010, Elsevier Inc., pp. 243-274.
Fung et al., Anatomical localization of commensal bacteria in immune cell homeostasis and disease, Immunological Reviews 2014, vol. 260, 2014, pp. 35-49.
Brenchley et al., Microbial Translocation Across the GI Tract, The Annual Review of Immunology, vol. 30, Jan. 3, 2012, pp. 149-173.
Manichanh et al., The gut microbiota in IBD, Nature Reviews Gastroenterology & Hepatology., vol. 9, Aug. 21, 2012, pp. 599-608.
Hooper et al., Immune adaptations that maintain homeostasis with the intestinal microbiota, Nature Reviews Immunology, vol. 10, 2010, pp. 159-169.
Sonnenberg et al., Innate Lymphoid Cells Promote Anatomical Containment of Lymphoid-Resident Commensal Bacteria, Science, vol. 336, Jun. 6, 2012, pp. 1321-1325.
Obata et al., Indigenous opportunistic bacteria inhabit mammalian gut-associated lymphoid tissues and share a mucosal antibody-mediated symbiosis, PNAS, vol. 107, No. 16, Apr. 20, 2010, pp. 7419-7424.
Kunisawa et al., Alcaligenes is commensal bacteria habituating in the gut-associated lymphoid tissue for the regulation of intestinal IgA responses, Frontiers in Immunology, vol. 3, art. 65, Apr. 2, 2012, pp. 1-5.
Hooper et al., Interactions Between the Microbiota and the Immune System, Science, vol. 336, Jun. 6, 2012, pp. 1268-1273.
Corthesy, B. et al., Cross-talk between Probiotic Bacteria and the Host Immune System, The Journal of Nutrition, 2007, vol. 137, No. 3, pp. 781S-790S.

* cited by examiner

*Primary Examiner* — Sarvamangala Devi
(74) *Attorney, Agent, or Firm* — Hodgson Russ LLP

(57) ABSTRACT

Provided herein are probiotic compositions and methods to enhance bacterial diversity in the intestinal tract of a subject. A probiotic is provided comprising lymphoid tissue-resident commensal bacteria, and optionally IL-10, IL-22, and/or hepcidin. The probiotic can be used to promote intestinal health or to treat or prevent intestinal disease or condition.

20 Claims, 37 Drawing Sheets

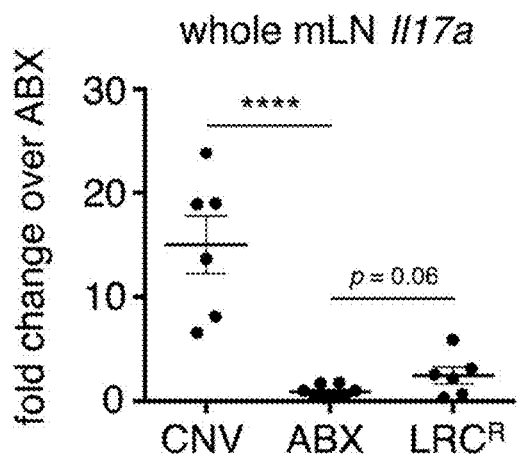
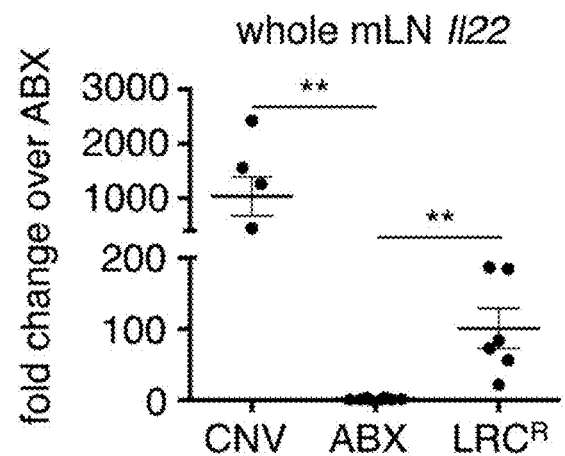
Figure 5F
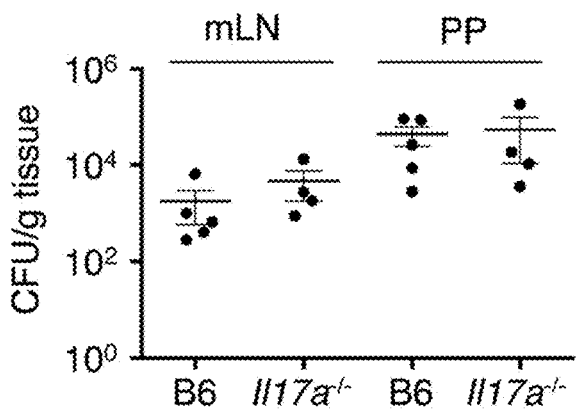
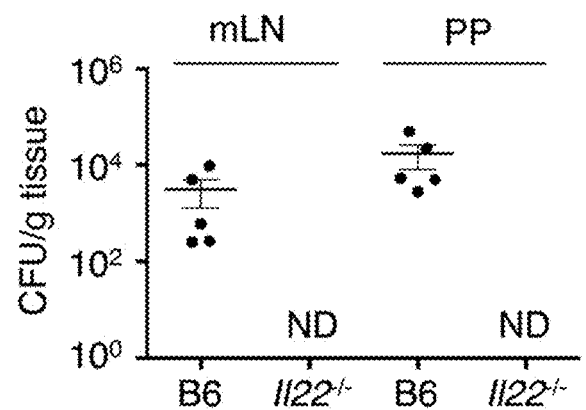
Figure 5G
Figure 5H
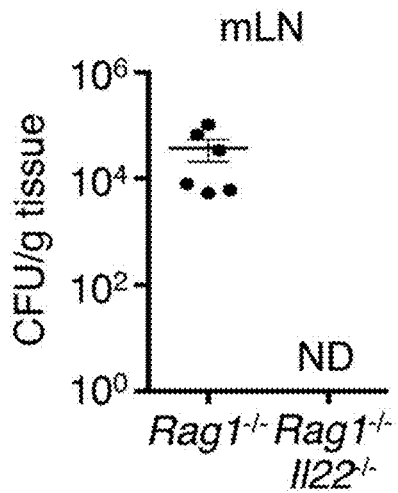
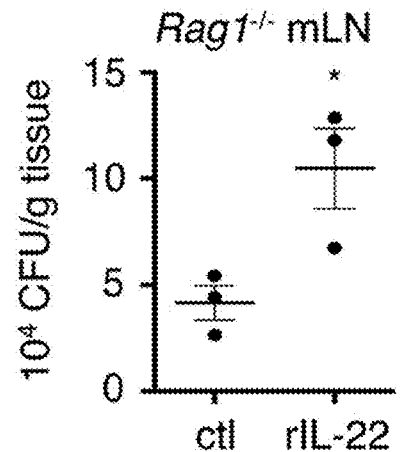
Figure 5I
Figure 5J

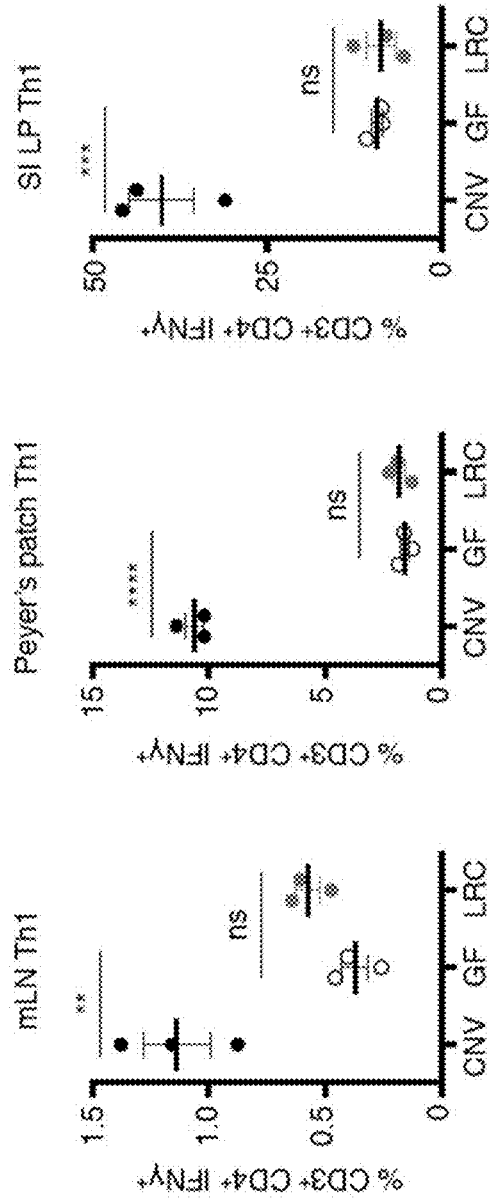
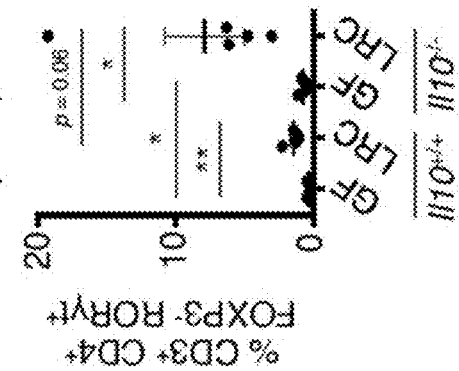
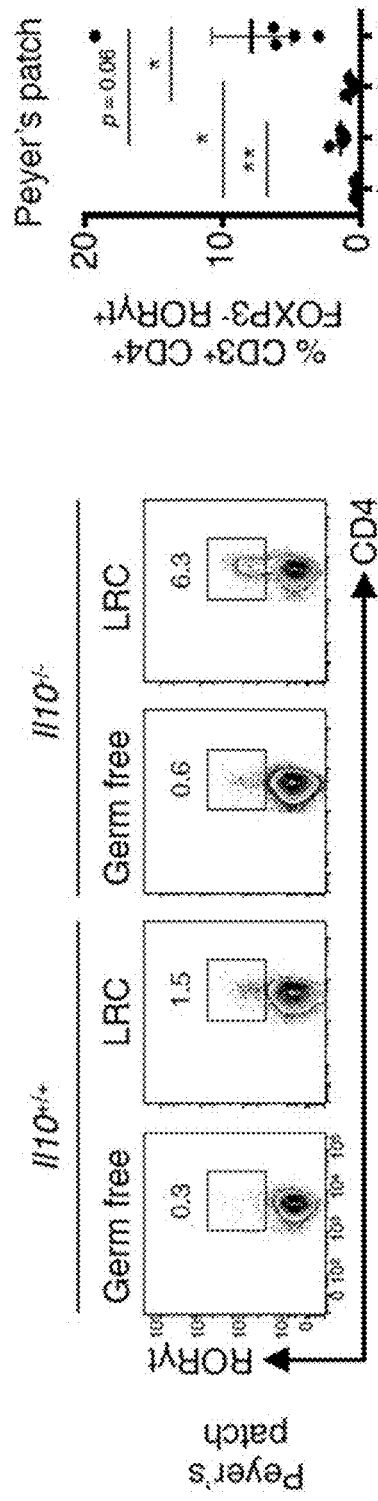
Figure 9B
Figure 9C
Figure 9D

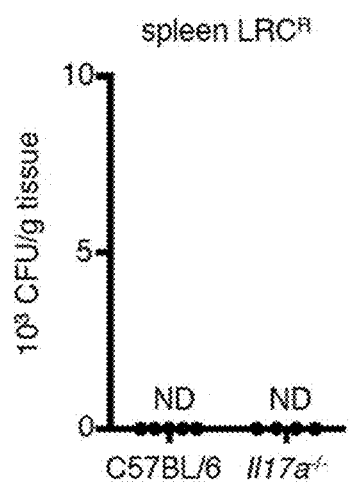
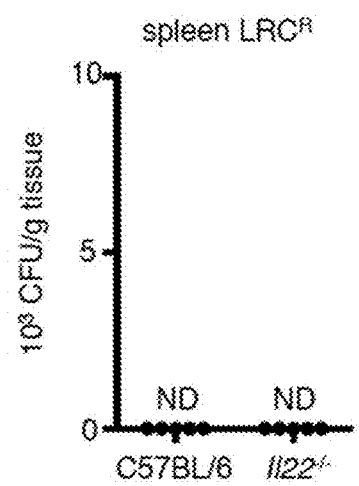
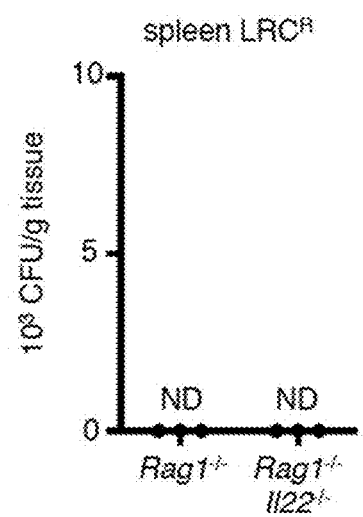
Figure 10C
Figure 10D
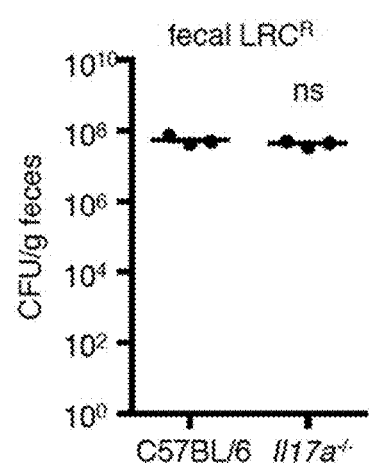
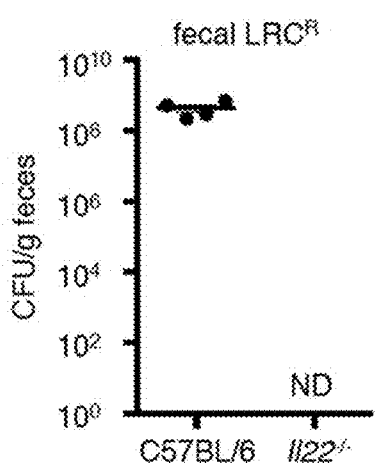
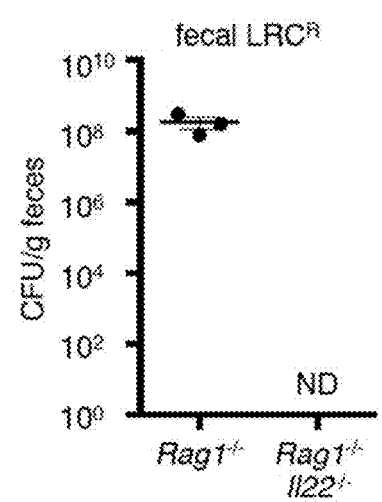
Figure 10E
Figure 10F

PROBIOTIC COMPOSITIONS AND METHODS OF USE

CROSS-REFERENCE TO RELATED APPLICATIONS

This application claims priority to U.S. Provisional application No. 62/471,041 filed on Mar. 14, 2017, the disclosure of which is incorporated herein by reference.

STATEMENT REGARDING FEDERALLY SPONSORED RESEARCH

This invention was made with government support under Grant Numbers DK110262, OD012116, AI114724 and AI123368 awarded by the National Institutes of Health. The United States Government has certain rights in the invention.

FIELD OF THE DISCLOSURE

This disclosure relates generally to probiotic compositions useful for promoting the intestinal health, and more specifically to a probiotic composition comprising lymphoid tissue-resident commensal bacteria.

BACKGROUND OF THE DISCLOSURE

Trillions of microorganisms constitutively colonize the mammalian gastrointestinal (GI) tract and are essential to aid in nutrient metabolism and resistance to pathogen infection, as well as the development and maturation of the immune system. In the healthy intestine, most commensal bacteria are restricted to the lumen of the GI tract or found associated with the surface of the intestinal epithelium and remain physically separated from the immune cells that populate the lamina propria and intestinal-associated lymphoid tissues including isolated lymphoid follicles (ILF), Peyer's patches (PP) and the mesenteric lymph nodes (mLN) (Chow et al., 2010, Advances in immunology 107, 243-274; Hooper et al., 2012, Science 336, 1268-1273; Hooper and Macpherson, 2010, Nat Rev Immunol 10, 159-169). Physical separation of commensal bacteria from immune cells is achieved by multiple physical and biochemical mechanisms that include epithelial cells that line the intestine, tight junction proteins, and secretion of antimicrobial peptides, mucus and immunoglobulin A (Chow et al., 2010, Advances in immunology 107, 243-274; Hooper et al., 2012, Science 336, 1268-1273; Hooper et al., 2010, Nat Rev Immunol 10, 159-169). Anatomical segregation of commensal bacteria from the immune system, often referred to as the "demilitarized zone", is essential to prevent pathologic immune responses against commensal bacteria. Consistent with this, translocation of commensal bacteria across the intestinal epithelium can lead to the generation of pro-inflammatory immune cell responses and are often associated with the pathogenesis of multiple chronic diseases, such as inflammatory bowel disease, metabolic disorders and HIV/AIDS (Brenchley et al., 2012, Annual review of immunology 30, 149-173; Manichanh et al., 2012, Nature reviews, Gastroenterology & hepatology 9, 599-608).

Recent studies suggest that a unique subset of commensal bacteria can colonize the interior of intestinal-associated lymphoid tissues of healthy mammals (Fung et al., 2014, Immunological reviews 260, 35-49; Kunisawa et al., 2012, Frontiers in immunology 3, 65; Obata et al., 2010, Proceedings of the National Academy of Sciences of the United States of America 107, 7419-7424; Sonnenberg et al., 2012, Science 336, 1321-1325). Using 16S rDNA sequencing and fluorescence in situ hybridization (FISH), one report identified the presence of multiple species of commensal bacteria in the interior of ILFs, PPs and the mLN of healthy mice, non-human primates and humans (Obata et al., 2010, Proceedings of the National Academy of Sciences of the United States of America 107, 7419-7424). These bacteria include *Alcaligenes* spp., *Achromobacter* spp., *Bordetella* spp. and *Ochrobactrum* spp. 16S rDNA for many of these lymphoid tissue-resident commensal bacteria (LRCs) were found associated with CD11c+ dendritic cells (DCs), suggesting a role for DCs in lymphoid tissue colonization. In a subsequent study, it was demonstrated that interleukin (IL)-22 and group 3 innate lymphoid cells (ILC3) are important in preventing systemic dissemination of one LRC, *Alcaligenes xylosoxidans*, and subsequent induction of systemic inflammation (Sonnenberg et al., 2012, Science 336, 1321-1325). These data highlight that intestinal-associated lymphoid tissues are potential sites for colonization by commensal bacteria and innate immune pathways maintain anatomical containment between LRCs and the systemic immune system. However, the functional significance of this colonization to the host remain undefined.

SUMMARY

Physical separation between the mammalian immune system and commensal bacteria is necessary to limit chronic inflammation. However, selective species of commensal bacteria can reside within intestinal-associated lymphoid tissues of healthy mammals. Here, we demonstrate that lymphoid tissue-resident commensal bacteria (LRC) colonized murine dendritic cells and modulate their cytokine production. In germ-free and antibiotic-treated mice, LRCs colonized intestinal-associated lymphoid tissues and induced multiple members of the IL-10 cytokine family, including dendritic cell-derived IL-10 and group 3 innate lymphoid cell (ILC3)-derived IL-22. Notably, IL-10 limited the development of pro-inflammatory Th17 cell responses, and IL-22 production enhanced LRC colonization in the steady state. Furthermore, LRC colonization protected mice from lethal intestinal damage in an IL-10-IL-10R-dependent manner. Collectively, our data reveal a unique host-commensal bacteria dialogue whereby selective subsets of commensal bacteria interact with dendritic cells to facilitate tissue-specific responses that are mutually beneficial for both the host and the microbe.

The present disclosure provides a method to promote the health of the intestinal tract of a mammalian subject by delivering to the intestinal tract a composition comprising lymphoid tissue-resident commensal bacteria selected from *Alcaligenes* species, *Achromobacter* species, *Bordetella* species, and/or *Ochrobactrum* species. The composition may be a probiotic composition. The probiotic may comprise one or more, two or more, or three or more bacteria selected from *Achromobacter* species, *Achromobacter* species, *Bordetella* species, and *Ochrobactrum* species. In one embodiment, the probiotic may comprise all of the following bacteria: *Alcaligenes* species, *Achromobacter* species, *Bordetella* species, and *Ochrobactrum* species. The subject may be a human. The probiotic may comprise one or more bacteria species selected from the group: *Achromobacter xylosoxidans* also known as *Alcaligenes xylosoxidan*, *Alcaligenes faecalis*, *Ochrobactrum* anthropi, *Ochrobactrum intermedium*, *Bordetella holmesii*, and *Bordetella hinzii*. In one embodiment, the probiotic does not have any bacteria that are predominantly present in the lumen of the GI tract (compared to the lymphoid tissue). In one embodiment, the *Alcaligenes* species, *Achromobacter* species, *Bordetella* species, and *Ochrobactrum* species are the only bacteria present in the probiotic. The probiotic may additionally comprise IL-10, IL-22 and/or hepcidin. The present compositions may be used to increase or enhance the intestinal microbiota of a mammalian subject. Microbiota may be enhanced by increasing the number/proportion of a particular bacterial genus or species, or by increasing the diversity—i.e. increasing the number of genuses or species of bacteria in the intestine. Microbiota may also be altered in that useful bacteria are increase over those that are not useful or that are harmful.

This disclosure also provides a method to treat or prevent an intestinal disease or condition in a mammalian subject by administering a probiotic comprising lymphoid tissue-resident commensal bacteria selected from *Alcaligenes* species, *Achromobacter* species, *Bordetella* species, and *Ochrobactrum* species. The subject may be a human. The probiotic may comprise one or more bacteria species selected from the group: *Achromobacter xylosoxidans* also known as *Alcaligenes xylosoxidan*, *Alcaligenes faecalis*, *Ochrobactrum anthropi*, *Ochrobactrum intermedium*, *Bordetella holmesii*, and *Bordetella hinzii*. The method may also comprise administering to the subject IL-10, IL-22 and/or hepcidin, which may be administered separately or together with the bacteria.

In one aspect, the disclosure provides kits for promoting the health of the intestinal tract of a subject. The kit can comprise a probiotic comprising bacteria selected from *Alcaligenes* species, *Achromobacter* species, *Bordetella* species, and *Ochrobactrum* species, and optionally, IL-10, IL-22 and/or hepcidin. The IL-10, IL-22 and/or hepcidin may be formulated in the probiotic or may be packaged separately. The kit can also contain instructions for use of the probiotic and accompanying agents. The instructions may include guidance on dosage, timing, frequency of administration, and storage instructions.

The disease or condition that may be treated or prevented with the present probiotics may be selected from inflammatory bowel diseases such as Crohn's disease and ulcerative colitis, irritable bowel syndrome, side effects of drug treatment such as chemotherapy or antibiotic treatment, an autoimmune condition mediated in part by gut microflora such as allergy, asthma and diabetes mellitus type 1, obesity, and metabolic syndrome, liver disease, and cancers including but not limited to cancers of intestines, lung, skin, pancreas, brain, and liver. The method may further comprise administering to the subject IL-10, IL-22, and/or hepcidin which may be formulated with the probiotic or administered separately.

The present probiotic compositions may be formulated to oral delivery. In other embodiments, the compositions may be formulated for delivery via other routes.

The present probiotic may be used in combination with fecal matter transplant, wherein the probiotic improves colonization with bacteria and increases the diversity of intestinal microbiota after FMT. The probiotic may be administered prior to, together with, or after the FMT treatment.

In one aspect, a method is provided to treat or prevent a disease or condition in a mammalian subject by administering dendritic cells to said subject, which dendritic cells have been cultured with lymphoid tissue-resident commensal bacteria selected from *Alcaligenes* species, *Achromobacter* species, *Bordetella* species, and *Ochrobactrum* species. The subject may be a human. The disease or condition may be selected from inflammatory bowel diseases such as Crohn's disease and ulcerative colitis, irritable bowel syndrome, side effects of drug treatment such as chemotherapy or antibiotic treatment, an autoimmune condition mediated in part by gut microflora such as allergy, asthma and diabetes mellitus type 1, obesity, and metabolic syndrome, liver disease, and cancer, which includes cancer of intestines, lung, skin, pancreas, brain, and liver. The lymphoid tissue-resident commensal bacteria used to culture the dendritic cells comprise one or more bacteria species selected from the group: *Achromobacter xylosoxidans* also known as *Alcaligenes xylosoxidan*, *Alcaligenes faecalis*, *Ochrobactrum anthropi*, *Ochrobactrum intermedium*, *Bordetella holmesii*, and *Bordetella hinzii*. The dendritic cells may be autologous and may be cultured with one or more of IL-10, IL-22 and hepcidin. The invention also comprises administering one or more of IL-10, IL-22 and hepcidin to the subject to whom the dendritic cell therapy is administered. IL-10, IL-22 and/or hepcidin may be formulated with the dendritic cell therapy composition.

BRIEF DESCRIPTION OF THE DRAWINGS

FIGS. 5A-5L. Lymphoid tissue-resident commensal bacteria colonize antibiotic-treated mice and elicit innate immune responses that enhance colonization. Bacterial CFUs were determined in antibiotic (ABX)-treated control and ABX-resistant *Achromobacter* (LRC$^R$)-colonized C57BL/6 PP and mLN homogenates (A and B) or Rag1$^{-/-}$ mLN homogenates (C). Data representative of at least 2 independent experiments. (D) LRC$^R$ 16S rDNA was measured in sorted CD11c$^+$ cells from ABX-treated control or LRC$^R$-colonized Rag1$^{-/-}$ mLN. (E) Expression of Il1b, Il10 and Il23a was measured in sorted CD11c$^+$ cells from ABX-treated control or LRC$^R$-colonized Rag1$^{-/-}$ mLN. Data pooled from 2 independent experiments for a total of 6 mice per group. (F) mLNs of CNV, ABX-treated and LRC$^R$-colonized were analyzed for expression of Il17a and Il22. Data pooled from 2 independent experiments for a total of 6-8 mice per group. One-way ANOVA, Il17a—**p<0.0001; Il22—p<0.01. (G and H) mLN and PP homogenates from LRC$^R$-colonized C57BL6, Il17a$^{-/-}$ and Il22$^{-/-}$ mice were cultured to determine CFUs. (I) mLN homogenates from LRC$^R$-colonized Rag1$^{-/-}$ and Rag1$^{-/-}$ Il22$^{-/-}$ mice were cultured to determine CFUs. Data pooled from 2 independent experiments for a total of 5-6 mice per group. (J) mLN homogenates from control or recombinant mouse IL-22 (rIL-22)-treated Rag1$^{-/-}$ mice were cultured to determine CFUs. Data representative of 2 independent experiments using recombinant mouse IL-22 or IL-22-Fc. (K and L) Whole PP and mLN were stained with *Alcaligenes*-specific 16S FISH probes ALBO (red) and BPA (green), and wheat germ agglutinin (blue). Data representative of 2 independent experiments with 2-5 mice per group. Number of puncta per mm$^3$ of tissue was quantified. Data are represented as mean±SEM. Statistics shown in panels E, F, J, K and L were performed using unpaired, two-tailed, student's t test (E, J, K and L) and one-way ANOVA with uncorrected Fisher's LSD test (F). *, p<0.05; , p<0.01; *, p<0.001. ND, not detectable. See also FIGS. 10A-10H FIG. 10.

FIGS. 9A-9E. Colonization of germ-free mice with lymphoid tissue-resident commensal bacteria does not promote intestinal inflammation and Th1 cell responses (Related to FIGS. 3A-3K). (A) H&E staining of small intestine and colon of conventional (CNV), germ-free (GF) and mice monocolonized with Bordetella spp. (LRC-monocolonized) for 2 weeks. (B) Frequencies of Th1 (CD3$^+$CD4$^+$IFNγ$^+$) cells in the mesenteric lymph node (mLN), Peyer's patch (PP) and small intestine lamina propria (SI LP) of CNV, GF and LRC monocolonized mice. One-way ANOVA, mLN—$p<0.01$; PP—$p<0.0001$; SI LP—*$p<0.001$. Data representative of 3 independent experiments. (C and D) Frequencies of Th17 cells (CD3$^+$CD4$^+$RORγt$^+$FOXP3$^-$) in the PP of LRC-monocolonized Il10$^{+/+}$ or Il10$^{-/-}$ mice. Data representative of 2 independent experiments with 2-5 mice per group using either Il10$^{-/-}$ monocolonized mice or C57BL/6 monocolonized mice with anti-IL-10R treatment (500 μg/mouse every 3 days, analyze on day 7). One-way ANOVA, **$p<0.01$. (E) Numbers of total or IL-22$^+$ ILC3 in the mLN of CNV, GF, SFB-monocolonized and LRC-monocolonized mice. Data representative of 2 independent experiments with 4-5 mice per group. Statistics shown in panels B and D were performed using one-way ANOVA with uncorrected Fisher's LSD test (B) or unpaired, two-tailed, student's t test with no correction for multiple comparisons (D). *, $p<0.05$; , $p<0.01$; *, $p<0.001$.

FIGS. 10A-10H. IL-22 may promote lymphoid tissue-resident commensal bacteria colonization by limiting competing commensal microbes (Related to FIGS. 5A-5L). (A) Peyer's patches (PP) of CNV, ABX-treated and ABX-resistant Achromobacter (LRC$^R$)-colonized C57BL/6 mice were analyzed for frequencies of IL-22$^+$ ILC3. One-way ANOVA, *$p<0.01$. (B) Small intestinal (SI) tissues of CNV, ABX-treated and LRC$^R$-colonized Rag1$^{-/-}$ mice were analyzed for expression of Il17a and Il22. Data pooled from 2 independent experiments for a total of 6-8 mice per group. One-way ANOVA, Il17a—*$p<0.001$; Il22—$p<0.01$. (C) Bacterial CFUs were determined in spleen homogenates of LRC$^R$-gavaged C57BL/6, Il17a$^{-/-}$ and Il22$^{-/-}$ mice. (D) Bacterial CFUs were determined in spleen homogenates of LRC$^R$-gavaged Rag1$^{-/-}$ and Rag1$^{-/-}$Il22$^{-/-}$ mice. (E) Fecal CFUs were determined in LRC$^R$-gavaged C57BL/6, Il17a$^{-/-}$, Il22$^{-/-}$, Rag1$^{-/-}$ and Rag1$^{-/-}$Il22$^{-/-}$ mice. Data representative of at least 2 independent experiments. (F) Fecal CFUs were determined in ampicillin and gentamicin (AG)-treated, LRC$^R$-gavaged C57BL/6, Il22$^{+/+}$ and Il22$^{-/-}$ mice. (G) Fecal CFUs were determined in AG-treated, LRC$^R$-gavaged C57BL/6, Il22$^{+/+}$ and Il22$^{-/-}$ mice following treatment with neomycin, metronidazole and vancomycin (NMV) for 1 week. One-way ANOVA, **, $p<0.0001$. (H) Fecal and mLN CFUs were determined in AG-treated, LRC$^R$-gavaged C57BL/6, C57BL/6 mice co-housed with Il22$^{-/-}$ (C57BL/6 CH) and Il22$^{-/-}$ mice. Data in F, G and H are representative of 2 independent experiments. Statistics shown in panels A and B were performed using one-way ANOVA with uncorrected Fisher's LSD test. Statistics shown in panel G were performed using one-way ANOVA and the Tukey's multiple comparisons test. , $p<0.01$; *, $p<0.001$; **, $p<0.0001$.

DETAILED DESCRIPTION

Figure 1A:
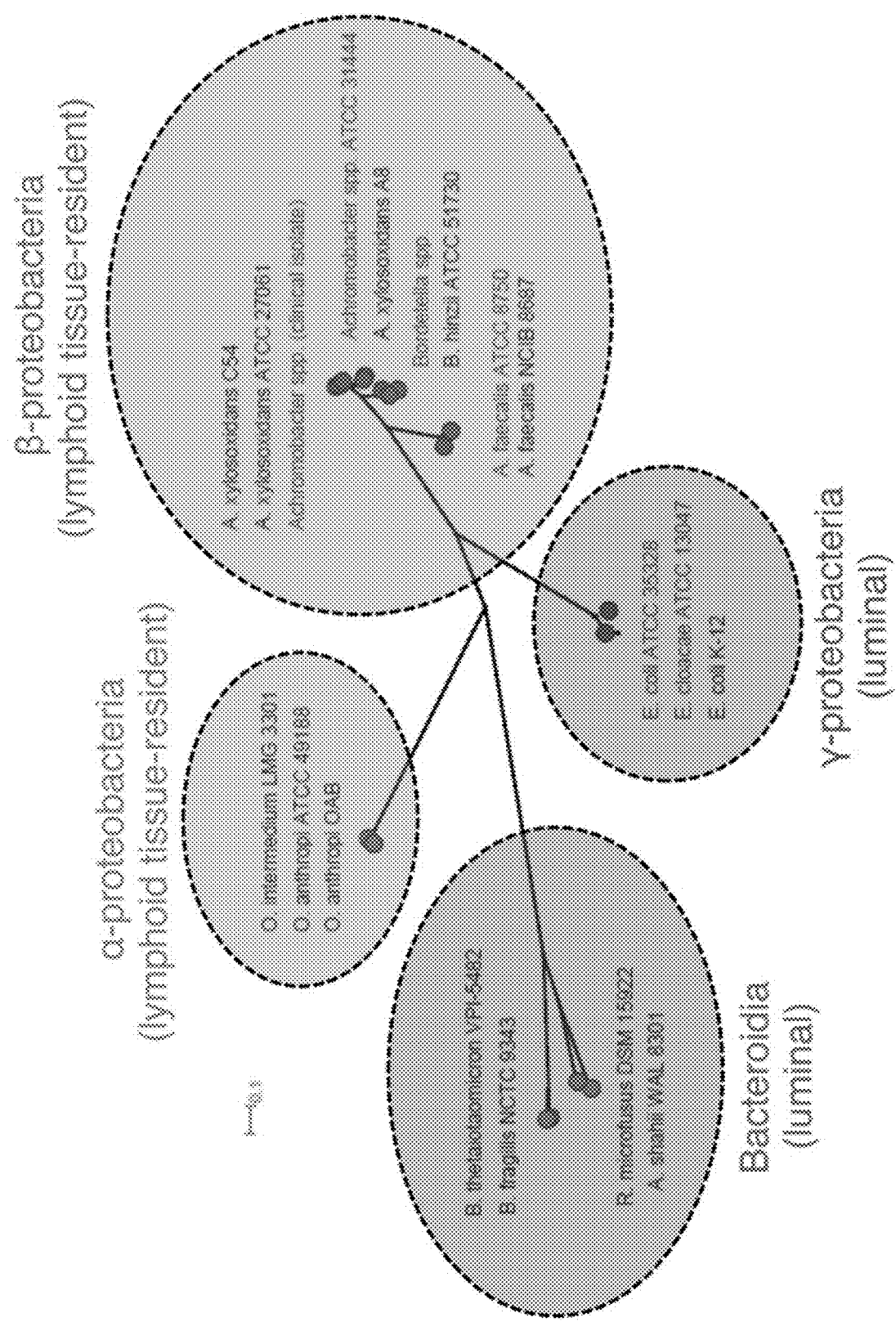
FIGS. 1A-1F. Lymphoid tissue-resident commensal bacteria colonize bone marrow-derived and primary dendritic cells. (A) Maximum-likelihood tree of 47 bacterial genomes based on 40 universal single copy marker genes. Scale bar indicates number of substitutions per site. (B) Bone marrow-derived dendritic cells (BMDCs) were co-cultured with representative LRCs or luminal-resident commensals and bacterial survival was measured at 0, 48 and 96 hours. l.o.d., limit of detection. Data are representative of at least 2 independent experiments. (C) Primary DCs isolated from the mesenteric lymph node (mLN) of C57BL/6 mice were co-cultured with the mouse-derived LRC, *Bordetella* spp. or luminal-resident commensal, *E. coli* ATCC 35328, and bacterial survival was measured at 0 and 96 hours. l.o.d., limit of detection. Data representative of 2 independent experiments (D) *Bordetella*-colonized BMDCs were analyzed at day 5 post co-culture by transmission electron microscopy. Images are representative of 10 individual bacteria-containing DCs. (E) *Bordetella*- and *E. coli*-colonized BMDCs were analyzed at day 0, 2 and 5 post-co-culture by immunofluorescence. Scale bar—5 µm. Data representative of 2 independent experiments. (F) Percentage of BMDCs containing live bacteria was quantified across 7-16 distinct fields of view. Infection efficiency (BMDCs containing live or dead bacteria/total BMDCs) on day 0 was approximately 15% for *Bordetella* spp. and 30% for *E. coli*. Data are represented as mean±SEM. Statistics shown were performed using unpaired, two-tailed, student's t test. ***, $p<0.0001$. ND, not detectable. See also FIGS. 7A and 7B FIG. 7 and Table 1.

In the following description, reference is made to the accompanying drawings that form a part hereof, and in which are shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

In this disclosure, we demonstrate that LRCs can colonize murine DCs, modulate DC cytokine production in a viability-dependent manner and promote local Th17 cell and ILC3 responses in intestinal-associated lymphoid tissues in vivo. Further, our data indicate that ILC3-derived IL-22 enhanced LRC colonization of intestinal-associated lymphoid tissues, and LRC-induced IL-10 limited pro-inflammatory responses in the steady state and could protect mice in a model of intestinal damage. Collectively, these data demonstrate that LRCs engage in a mutualistic dialogue with mammalian hosts by eliciting members of the IL-10 cytokine family.

Our results define a unique host-commensal bacteria dialogue whereby direct interactions between LRCs and the mammalian immune system orchestrate tissue-specific immune responses that are mutually beneficial for the host and microbe. While most studies of host-microbiota interactions to date have focused on populations of commensal bacteria residing in the intestinal lumen or attached to the intestinal epithelium, here we interrogate an under-appreciated class of commensal bacteria that has the potential to reside closely associated with immune cells in the interior of intestine-associated lymphoid tissues. This colonization pattern is paradoxical to our current understanding of interactions between the immune system and the majority of other commensal bacteria, which suggests that anatomical segregation must occur to limit the development of pathologic immune responses. Our data highlighting this unique colonization pattern and selective interactions with the healthy mammalian immune system represent a key advance in our understanding of host-commensal bacteria relationships.

Interrogating functional interactions between the host immune system and several species of LRCs revealed that LRCs but not luminal members of the microbiota (that reside in the lumen, but not in the lymphoid tissue) could colonize and persist within DCs and modulate selective DC cytokine responses in a viability-dependent manner. Constitutive colonization of DCs by LRCs likely maintains expression of viability-dependent cytokines, including IL-1β, IL-10 and IL-23. This is in direct contrast to luminal-resident or epithelial-attached commensal bacteria in which viable bacteria belonging to these groups are not typically found beyond the intestinal epithelium. Therefore, these commensal bacteria predominantly influence immune cells through indirect interactions, such as via production of metabolites or modulation of intestinal epithelial cell responses. Furthermore, our data suggest that induction of tissue-specific immune responses by commensal bacteria is linked to their anatomical localization in the GI tract and associated lymphoid tissues. In the present disclosure, we demonstrate that LRCs colonize and activate DCs to selectively promote Th17 and ILC3 responses within intestinal-associated lymphoid tissues.

Our data demonstrates that IL-22 facilitates colonization of lymphoid tissues by LRCs. We demonstrate that $Il22^{-/-}$ mice harbor intestinal microbes that limit LRC colonization in the lumen likely through competition for space or nutrients. These data suggest that IL-22 indirectly promotes LRC colonization in multiple contexts by restricting colonization of competing intestinal microbes. In the current study, we did not observe systemic dissemination of a distinct but related LRC, but rather impaired lymphoid tissue entry and colonization in mice deficient in IL-22. Therefore, our findings highlight a multifaceted role for IL-22 in maintaining anatomical localization of LRCs, by both promoting lymphoid tissue colonization and limiting systemic dissemination.

LRC colonization is sufficient to protect mice from lethal intestinal damage, supporting the hypothesis that host recognition of commensal bacteria provides beneficial microbial stimulation to limit intestinal damage. Despite our understanding of microbial recognition pathways in host protection from intestinal injury, the downstream signals induced are not fully understood. Our current data suggest that MYD88-dependent IL-10 induction by LRCs is one pathway that provides tissue protective functions in the context of intestinal injury and systemic inflammation. Our data support a model whereby, following LRC colonization, IL-10 produced by DCs in intestinal-associated lymphoid tissues has local effects in limiting Th17 cell responses in the steady state, as well as distal effects on the intestinal epithelium and systemic circulation in the context of intestinal damage. These findings demonstrate a previously unrecognized and mutually beneficial dialogue between the host and LRCs. Colonization of lymphoid tissues by commensal bacteria modulates the host immune system in a tissue-specific manner and confers protective effects in the context of intestinal damage.

This disclosure also describes that intestinal diversity can be affected by delivery of LRCs to the intestine. This was since LRCs are typically anatomically segregated from the microbiota of the lumen and one would not expect the LRCs to have any effect on the lumen microbiota diversity. For example, a much greater increase in intestinal microbiota diversity was observed after FMT treatment if the FMT treatment was carried out in conjunction with LRC delivery to the intestinal lumen as compared to delivery of a lumen resident bacteria (such as *E. coli*). These data suggest that LRCs may represent a bacteria that are essential to maintain the diversity of microbiota found in the intestinal lumen. The present probiotic compositions may be used to increase intestinal bacterial diversity either by itself or in conjunction with administration of a recolonizing composition, which may be FMT material.

Probiotics

Probiotics are microorganisms that are believed to provide health benefits when administered to a subject.

Compositions

The probiotic compositions of the subject invention include lymphoid tissue-resident commensal bacteria selected from one or more *Achromobacter* species, *Alcaligenes* species, *Bordetella* species, and *Ochrobactrum* species.

Examples of *Achromobacter* species include *A. arsenitoxydans, A. cholinophagum, A. clevelandea, A. cycloclastes, A. denitrificans, A. insolitus, A. lyticus, A. marplatensis, A. obae, A. piechaudii, A. ruhlandii, A. spanius, A. xylosoxidans*. Preferred *Achromobacter* species include *A. xylosoxidans* and *A. denitrificans*.

Examples of *Alcaligenes* species include *A. xylosoxidans, A. faecalis, A. aestus, A. aquatilis, A. cupidus, A. defragrans, A. denitrificans, A. piechaudii*, and *A. xylosoxidans*. Preferred *Alcaligene* species include *A. xylosoxidans* and *A. faecalis*. Note that *A. xylosoxidan* has been classified both under *Alcaligenes* and *Achromobacter*.

Examples of *Bordetella* species include *B. holmesii, B. hinzii, B. ansorpii, B. avium, B. bronchiseptica, B. parapertussis, B. pertussis, B. petrii*, and *B. trematum*. Preferred *Bordetella* species include *B. holmesii* and *B. hinzii*.

*Ochrobactrum* species include *O. anthropi, O. intermedium, O. ciceri, O. cytisi, O. daejeonense, O. gallinifaecis, O. grignonense, O. guangzhouense, O. haematophilum, O. intermedium, O. lupini, O. oryzae, O. ecoris, O. pituitosum, O. pseudintermedium, O. pseudogrignonense, O. rhizosphaerae, O. thiophenivorans*, and *O. tritici*. Preferred *Ochrobactrum* species include *O. anthropi* and *O. intermedium*.

The invention also provides cell therapy compositions comprising dendritic cells that have been cultured with any of the lymphoid tissue-resident commensal bacteria compositions of the invention. The dendritic cells may be cultured with IL-10 and/or IL-22. The dendritic cells may be genetically modified before being administered to the subject. The dendritic cells may be harvested from the subject to which they will be administered, or may be allografts. Methods to harvest, culture, genetically modify, and administer dendritic cells as part of a cell therapy are well known in the art of cancer immunotherapy. See for example Ramachandran 2017; Anguille et al., 2014; Palucka and Banchereau, 2012; and Humbert and Halary, 2012, which are incorporated herein in their entirety. These methods may be adopted to treat the intestinal diseases and conditions and cancers discussed herein. The probiotic or cell therapy may be formulated with one of both of the cytokines IL-10 or IL-22, or one or both of these may be separately administered. For use in a human, human proteins are preferred. If administered separately, IL-10 and/or IL-22 may be administered before, during, or after the administration of the probiotic. If administered before or after, the IL-10 and/or IL-22 may be administered between one week before or after and immediately before or after.

Human IL-10 is a 178 amino acid protein that has been well described, for example at the UniProt database as entry P22301, where the reference sequence is provided, and which is incorporated herein in its entirety. Human IL-22 is a 179 amino acid protein that has been well described, for example at the UniProt database as entry Q9GZX6, where the reference sequence is provided, and which is incorporated herein in its entirety. Without limiting the scope of the invention, one mechanism by which IL-22 is beneficial is by enhancing bacteria colonization.

Those of skill in the art will recognize that in other useful IL-10 and IL-22 proteins, numerous residues of any of the above-described IL-10 or IL-22 amino acid sequences can be substituted with other, chemically, sterically and/or electronically similar residues without substantially altering IL-10 or IL-22 biological activity. In addition, larger polypeptide sequences containing substantially the same coding sequences as IL-10 and IL-22 (e.g., splice variants) are contemplated.

Human hepcidin, a 25 amino acid peptide with antimicrobial and iron-regulating activity (Krause et al., FEBS Lett. 480:147 (2000); Park et al., J. Biol. Chem. 276:7806 (2001)). A hepcidin cDNA encoding an 83 amino acid pre-propeptide in mice and an 84 amino acid pre-propeptide in rat and human were reported (Pigeon et al., J. Biol. Chem. 276:7811 (2001)). The 24 residue N-terminal signal peptide is first cleaved to produce pro-hepcidin, which is then further processed to produce mature hepcidin, found in both blood and urine. See UniProt database at entry P81172. Any form of hepcidin that is biologically active may be used.

As employed herein, the term "substantially the same amino acid sequence" refers to amino acid sequences having at least about 60% sequence homology or identity with respect to any of the amino acid sequences described herein ("reference sequences"), including IL-10, IL-22 and hepcidin, and retaining comparable functional and biological activity characteristic of the protein defined by the reference sequences described, particularly with respect to neoplastic cellular proliferation and/or transformation or its inhibition. More preferably, proteins having "substantially the same amino acid sequence" will have at least about 80%, still more preferably about 90% amino acid identity with respect to a reference amino acid sequence, such as IL-10, IL-22 and hepcidin; with greater than about 95% amino acid sequence identity being especially preferred. It is recognized, however, that polypeptide containing less than the described levels of sequence identity arising as splice variants or that are modified by conservative amino acid substitutions are also encompassed within the scope of the present invention. The degree of sequence homology is determined by conducting an amino acid sequence similarity search of a protein data base, such as the database of the National Center for Biotechnology Information (ncbi.nlm.nih.gov/BLAST), using a computerized algorithm, such as Power-BLAST, QBLAST, PSI-BLAST, PHI-BLAST, gapped or ungapped BLAST, or the "Align" program through the Baylor College of Medicine server (hgsc.bcm.tmc.edu/seq_data). (e.g., Altchul et al., Nucleic Acids Res. 25(17): 3389-402 (1997); Zhang et al., Genome Res. 7(6):649-56 (1997); Madden, T. L., et al., Methods Enzymol. 266:131-4 (1996); Altschul et al., Basic local alignment search tool, J. Mol. Biol. 215(3):403-10 (1990)).

Also encompassed by the terms IL-10 or IL-22 proteins or hepcidin, respectively, are biologically functional or active peptide analogs thereof. The term peptide "analog" includes any polypeptide having an amino acid residue sequence substantially identical to a sequence specifically shown herein in which one or more residues have been conservatively substituted with a functionally similar residue and which displays the ability to mimic the biological activity of IL-10, IL-22, or hepcidin respectively, particularly with respect to their activity promoting colonization by the probiotics described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue, provided that such polypeptide displays the requisite biological activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The inventive polypeptide of the present invention also include any polypeptide having one or more additions and/or deletions of residues, relative to the sequence of a polypeptide whose sequence is shown herein, so long as the requisite PTTG or PTTG-C biological activity is maintained.

In one embodiment, the disclosure provides a probiotic composition comprising bacteria of the genus *Alcaligenes*. In one embodiment, the only bacteria present in the probiotic belong to the genus *Alcaligenes*. In one embodiment, the probiotic may further comprise bacteria from one or more of the genuses *Achromobacter, Bordetella*, and *Ochrobactrum*. In one embodiment, the only bacteria present in the probiotic belong to the genuses *Alcaligenes, Achromobacter, Bordetella*, and *Ochrobactrum*.

In one embodiment, the disclosure provides a probiotic composition comprising bacteria of the genus *Achromobacter*. In one embodiment, the only bacteria present in the probiotic belongs to the genus *Achromobacter*.

In one embodiment, the disclosure provides a probiotic composition comprising bacteria of the genus *Bordetella*. In one embodiment, the only bacteria present in the probiotic belong to the genus *Bordetella*.

In one embodiment, the disclosure provides a probiotic composition comprising bacteria of the genus *Ochrobactrum*. In one embodiment, the only bacteria present in the probiotic belong to the genus *Ochrobactrum*.

In different embodiments, the probiotic may comprise or consist essentially of the following bacteria, or these may be the only bacteria present in the probiotic composition: *Alcaligenes* and *Achromobacter*; *Alcaligenes* and *Bordetella*; *Alcaligenes* and *Ochrobactrum*; *Achromobacter* and *Bordetella*; *Achromobacter* and *Ochrobactrum*; *Bordetella* and *Ochrobactrum*; *Alcaligenes, Achromobacter* and *Bordetella*; *Alcaligenes, Achromobacter* and *Ochrobactrum*; *Alcaligenes, Achromobacter* and *Ochrobactrum*; *Achromobacter, Bordetella*, and *Ochrobactrum*; and *Alcaligenes, Achromobacter, Bordetella*, and *Ochrobactrum*.

In one embodiment, the probiotic composition comprises bacteria that are beta-proteobacteria class only. For example, the probiotic composition may comprise bacteria from one or more of the following *Alcaligenes, Achromobacter, Bordetella*, and *Ochrobactrum*, but does not comprise bacteria that are gamma-proteobacteria, the bacteriodetes phylum, and/or the firmicutes phylum. In one embodiment, the number of bacteria that belong to gamma-proteobacteria, the bacteriodetes phylum, or the firmicutes phylum is less than 10 million or less than 1 million per dose.

The amount of bacteria per dose may be 100 million to 1 billion and all values and ranges therebetween. In one embodiment, a dose may have more than 1 billion bacteria. A dose may be a tablet, capsule, or a specified amount of the formulation in any form. In various embodiments, the bacteria per dose may be 100, 200, 300, 400, 500, 600, 700, 800, 900 million or 1 billion, 2 billion, 3, billion etc.

The composition can be formulated for oral administration. The present oral compositions may be in the form of a chewable formulation, a dissolving or dissolved formulation, an encapsulated/coated formulation, a multi-layered lozenge (to separate active ingredients and/or active ingredients and excipients), a slow release/timed release formulation, or other forms suitable for oral delivery known in the art. It may be in the form of a tablet, lozenges, pill, capsule, drops or the like. The probiotic formulations, including pediatric formulations, may be flavored (e.g. fruit flavored, such as cherry, strawberry, blueberry etc.) and may be in a variety of shapes or colors.

In addition to the one or more genuses of bacteria, the probiotic may also comprise IL-10, IL-22 and/or hepcidin. Alternative, the IL-10, IL-22 and of hepcidin can be provided separately (such as in a prebiotic formulation). If provided separately from the bacteria, IL-10, IL-22 and hepcidin may be provided in one separate composition, or may be as individual compositions, or as various combinations, such as IL-10 and IL-22, IL-10 and hepcidin, or IL-22 and hepcidin. The amount of each of IL-10, IL-22 and hepcidin per dose may be 10 micrograms per kilogram to 1 mg per kilogram/body weight and all values and ranges therebetween. For example, the amount of each may be 50 to 200 micrograms per kilogram.

Pharmaceutical Formulations.

In another aspect, the present invention provides pharmaceutically acceptable compositions which comprise a therapeutically-effective amount of one or more of the bacterial species as described above, the cell therapies as described above, and/or the cytokines as discussed above, formulated together with one or more pharmaceutically acceptable excipients. In another aspect, the present invention provides pharmaceutically acceptable compositions which comprise a therapeutically-effective amount of one or more of the bacteria species, cell, and/or cytokines as described above, formulated together with one or more pharmaceutically acceptable excipients and other therapeutically effective medications known in the art allowing for but not limited to combination therapies to improve overall efficacy of each individual therapeutic or to limit the concentration of either therapeutic to avoid side effects and maintain efficacy. The active ingredient and excipient(s) may be formulated into compositions and dosage forms according to methods known in the art. As described in detail below, the pharmaceutical compositions of the present invention may be specially formulated for administration in solid or liquid form, including those adapted for the following: oral administration, for example, tablets, capsules, powders, granules, and aqueous or non-aqueous solutions or suspensions, drenches, or syrups, frozen or freeze-dried forms; or intrarectally, for example, as a pessary, cream or foam. In an embodiment, IL-10 or IL-22 is administered separately from the probiotic, and may be administered parenterally, for example, by subcutaneous, intramuscular or intravenous injection as, for example, a sterile solution or suspension; by topical application, for example, as a cream, ointment or spray applied to the skin, lungs, or mucous membranes; or intravaginally or intrarectally, for example, as a pessary, cream or foam; sublingually or buccally; transdermally; or nasally, and may be separately formulated as described herein or as is otherwise known in the art. In an embodiment, cell therapy is administered, and may be administered parenterally, for example, by subcutaneous, intramuscular or intravenous injection as, for example, a sterile solution or suspension; by topical application, for example, as a cream, ointment or spray applied to the skin, lungs, or mucous membranes; or intravaginally or intrarectally, for example, as a pessary, cream or foam; sublingually or buccally or nasally, and may be separately formulated as described herein or as is otherwise known in the art.

A therapeutically effective amount of the pharmaceutical composition of the present invention is sufficient to promote the health of the intestines, or to treat or prevent a disease characterized by symptoms comprising intestinal inflammation, autoimmune disease, or cancer. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the bacterial species and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may then be tableted, or other excipients may be added prior to tableting, such as a glidant and/or a lubricant.

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha, beta, or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259, hereby incorporated herein by reference) and Gramera, et al. (U.S. Pat. No. 3,459,731, hereby incorporated herein by reference) described electroneutral cyclodextrins. Other derivatives include cyclodextrins with cationic properties [Parmeter (II), U.S. Pat. No. 3,453,257, hereby incorporated herein by reference], insoluble crosslinked cyclodextrins (Solms, U.S. Pat. No. 3,420,788, hereby incorporated herein by reference), and cyclodextrins with anionic properties (Parmeter (III), U.S. Pat. No. 3,426,011, hereby incorporated herein by reference). Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin (see, Parmeter (III), supra]. Furthermore, sulfoalkyl ether cyclodextrin derivatives have been described by Stella, et al. (U.S. Pat. No. 5,134,127, hereby incorporated herein by reference).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 micrometers in diameter; large unilamellar vesicles (LUVS) are typically larger than 0.05 micrometers. Oligolamellar large vesicles and multilamellar vesicles have multiple, usually concentric, membrane layers and are typically larger than 0.1 micrometers. Liposomes with several nonconcentric membranes, i.e., several smaller vesicles contained within a larger vesicle, are termed multivesicular vesicles.

The liposome membrane may be formulated to provide increased carrying capacity. Alternatively or in addition, the probiotics of the present invention may be contained within, or adsorbed onto, the liposome bilayer of the liposome, or reside in the aqueous compartment.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057, both of which are hereby incorporated herein by reference; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, hereby incorporated herein by reference Release Modifiers The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween®. and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Subjects

The subject may be any animal, including human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

Preferred subjects include human subjects, who may be healthy or may be suffering from or at risk for a disease or condition of the intestines, immune system, or cancer. Examples of such conditions include inflammatory bowel diseases such as Crohn's disease and ulcerative colitis, irritable bowel syndrome, side effects of drug treatment such as chemotherapy or antibiotic treatment, an autoimmune condition mediated in part by gut microflora such as allergy, asthma and diabetes mellitus type 1, obesity, and metabolic syndrome, liver disease, and cancers including but not limited to cancers of intestines, lung, skin, pancreas, brain, and liver. The subject is generally diagnosed with the condition of the subject invention by skilled artisans, such as a medical practitioner. In a specific embodiment, the present probiotic compositions can be administered in conjunction with checkpoint inhibitor immunotherapies (such as for cancer).

In one aspect, the present disclosure provides a method of improving the health of the intestinal tract of a mammalian subject comprising administering to the subject a probiotic composition, such as an oral probiotic composition, described herein. For example, the disclosure provides a method of improving the health of the intestinal trach of a subject comprising administering to the subject a probiotic, such as an oral probiotic, comprising one or more of *Achromobacter* species, *Alcaligenes* species, *Bordetella* species, and *Ochrobactrum* species, and optionally further comprising administering one or more of IL-10, IL-12 and hecidin.

In one aspect, the present disclosure provides a method for preventing or treating a disease or condition comprising administering to an individual in need of treatment a probiotic composition, such as an oral probiotic composition, as described herein. For example, the disclosure provides a method of preventing or treating a condition comprising administering to the subject a probiotic comprising one or more of *Achromobacter* species, *Alcaligenes* species, *Bordetella* species, and *Ochrobactrum* species, and optionally further comprising administering one or more of IL-10, IL-12 and hecidin. The individual may have or may be at risk of having a condition such as inflammatory bowel diseases such as Crohn's disease and ulcerative colitis, irritable bowel syndrome, side effects of drug treatment such as chemotherapy or antibiotic treatment, an autoimmune condition mediated in part by gut microflora such as allergy, asthma and diabetes mellitus type 1, obesity, and metabolic syndrome, liver disease, and cancers including but not limited to cancers of intestines, lung, skin, pancreas, brain, and liver. In a specific embodiment, the present probiotic compositions can be administered in conjunction with checkpoint inhibitor immunotherapies (such as for cancer).

In one aspect, the present disclosure provides a method of increasing the bacterial colonization of the intestine of a mammalian subject comprising administering to the subject a probiotic composition, such as an oral probiotic composition, described herein. For example, the disclosure provides a method of increasing bacterial diversity in the intestine comprising administering to the subject a probiotic, such as an oral probiotic, comprising one or more of *Achromobacter* species, *Alcaligenes* species, *Bordetella* species, and *Ochrobactrum* species, and optionally further comprising administering one or more of IL-10, IL-12 and hecidin. Bacterial colonization may be increased by increasing the number of bacteria or diversity of bacteria (meaning the number of genuses and/or species of bacteria).

In one aspect, this disclosure provides a method to recolonize intestinal bacterial after the intestinal microbiota has been reduced or destroyed by disease, chemotherapy, radiation, antibiotics, injury, or any other condition comprising administration to a subject in need of treatment a probiotic composition described herein in conjunction with a recolonizing composition. The recolonizing composition may be a composition comprising one or more different types of bacteria that are desirable to be resident in the intestinal lumen. The recolonization composition may contain LRCs, although typically it will not have LRCs. In one embodiment, the recolonization composition (including FMT material) is free of bacteria belonging to the *Achromobacter* species, *Alcaligenes* species, *Bordetella* species, and *Ochrobactrum* species.

The present probiotic compositions and methods may be used in conjunction with fecal matter transplant therapies (FMT), which involves using intestinal bacteria from a healthy individual's fecal matter and then processing and transferring that bacteria to the infected patient directly. The fecal matter may be processed to extract the bacteria. The transplantation of the fecal matter is generally carried out by colonoscopy, endoscopy, sigmoidoscopy, or enema. FMT may also be carried out by using frozen or freeze-dried fecal microbiota administered in pill form As demonstrated by data presented herein, recolonization after FMT is improved by administration of a composition comprising LRC bacteria. Enhanced microbial diversity is a highly desirable outcome. Accordingly, in one embodiment, the present probiotic compositions may be administered before, together with, or after FMT, and can be continued as needed.

It was surprising that administration of LRCs controls the subsequent composition of bacteria that are resident in the lumen of the intestine (after FMT) given the anatomical segregation of these bacteria subsets. These data suggest that LRCs may represent a "keystone species" of bacteria that are essential to maintain the diversity of microbiota found in the intestinal lumen. Further, this appears to be a unique feature of LRCs as a luminal-resident *E. coli* was not able to induce the same diversity of microbiota following FMT reconstitution.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

The appropriate dosage and treatment regimen of the probiotic compositions may be determined or recommended by a clinician or nutritionist. In general, one or more doses may be administered per day for a day, week, month or longer if needed. For example, a dose may be administered every day for 1 week.

EXAMPLE 1

The present description is further illustrated by the following examples, which should not be construed as limiting in any way. The contents of all cited references (including literature references, issued patents, published patent applications as cited throughout this application) are hereby expressly incorporated by reference.

Experimental Procedures

Mice

C57BL/6 and Rag1$^{-/-}$ mice were purchased from Jackson Laboratories and used at 6-12 weeks of age. Conventional mice used as controls in gnotobiotic mice experiments were purchased from Jackson Laboratories and co-housed with mice bred in our conventional animal facility for at least 7 days before use. C57BL/6 and Rag1$^{-/-}$ mice used as controls for knockout mice were either bred in the same animal facility as the knockout mice, purchased from Jackson Laboratories and co-housed with mice bred in our SPF animal facility for at least 7 days or littermates as indicated to normalize for microbiota differences. All conventional mice were maintained in specific pathogen-free facilities at Weill Cornell Medical College. Germ-free and gnotobiotic C57BL/6 and Rag1$^{-/-}$ mice were maintained within sterile vinyl isolators at Weill Cornell Medical College Gnotobiotic Mouse Facility and monitored for germ-free or gnotobiotic status by weekly aerobic and anaerobic culturing. Germ-free and gnotobiotic Il10$^{+/+}$ and Il10$^{-/-}$ mice were maintained at the National Gnotobiotic Rodent Resource Center (University of North Carolina, Chapel Hill). Additional microbiology testing was performed on feces from mice under experimentation and at the endpoint of the experiment to confirm germ free or monocolonization status. DSS experiments using gnotobiotic mice were performed in a biosafety cabinet, and the gnotobiotic status of mice was confirmed by microbiology testing. Germ-free C57BL/6 mice were monocolonized with the mouse LRC isolate *Bordetella* spp., or SFB by oral gavage or cohousing with soiled bedding from previously monocolonized mice for at least 10 days. To establish LRC colonization in ABX-treated mice, conventional mice were treated in the drinking water with a limited ABX cocktail of ampicillin (1 mg/ml, Sigma) and gentamicin (1 mg/ml, Gemini Bio-Products) for C57BL/6, Il22$^{-/-}$ and mice or ampicillin (1 mg/ml), gentamicin (1 mg/ml) and neomycin (0.25 mg/ml, Sigma) for Rag1$^{-/-}$ and Rag1$^{-/-}$ Il22$^{-/-}$ for 3 days and then orally gavaged with the LRC isolate (LRC$^R$). Neomycin (0.25 mg/ml), metronidazole (0.5 mg/ml, Sigma) and vancomycin (0.25 mg/ml, Chem-Impex International) were added to the limited ABX cocktail as indicated. Antibiotic cocktails were supplemented with 1 packet of artificial sweetener (Sweet'N Low) per 250 ml. For cytokine treatments in vivo, rmIL-22 or PBS control (kindly provided by Pfizer) was injected i.p. at 25 µg/mouse every 2 days for 1 week and control- or IL-22-Fc (kindly provided by Pfizer) was injected i.p. at 50 µg/mouse every 3 days for 1 week. First injections were administered 1 day prior to LRC$^R$ colonization. All mice were used at least 10 days post LRC$^R$ colonization. All animals used are on a C57BL/6 background with the exception of Il10$^{-/-}$ and Il10$^{+/+}$ germ free mice, which are on a 12956/SvEv background. All experiments were performed according to the guidelines of the Weill Cornell Medical College Institutional Animal Care and Use Committee.

Microbiology

The LRC strain, *Bordetella* spp., used to colonized BMDCs or monocolonize germ-free mice was originally isolated from the spleen of an anti-CD90.2 mAb treated conventional Rag1$^{-/-}$ mice using a previously defined protocol (Sonnenberg et al., 2012, Science 336, 1321-1325). *E. coli* (human isolate) and *Ochrobactrum* spp. used to colonize BMDCs and the ABX-resistant (ampicillin, gentamicin, neomycin) LRC (LRC$^R$), *Achromobacter* used to colonize antibiotic-treated mice were human clinical isolates kindly provided by Kaede V. Sullivan (Children's Hospital of Philadelphia). Bacterial identities were determined by genomic sequencing (Wellcome Trust Sanger Institute) and confirmed by genus-specific 16S rDNA primers. *E. coli* R9 (ATCC 35328), *Enterobacter cloacae* (ATCC 13047) and gentamicin-sensitive *Achromobacter* spp. (ATCC 31444) used to colonize BMDCs were purchased from American Type Culture Collection. Feces from SFB-monocolonized mice were obtained from Dr. Yoshinori Umesaki and Dr. Tatsuichiro Shima (Yakult). All bacterial strains used to colonize GF mice and for in vitro DC assays were grown in LB broth and incubated at 250 RPM, 37° C. for 16-20 hours. For enumeration of tissue and fecal CFUs, the spleen, liver, feces, mesenteric lymph nodes (mLN) and Peyer's patches (PP) were isolated, homogenized in sterile PBS and plated on Brain Heart Infusion agar supplemented with 5% defibrinated horse blood. When culturing LRC$^R$ from tissues and feces, BHI blood agar plates were supplemented with 25 µg/ml ampicillin.

Bone Marrow-Derived and Primary Dendritic Cell Assays

Bone marrow-derived DCs were generated by culturing bone marrow cells in the presence of 20 ng/mL GM-CSF for 8-10 days. Culture media was replaced with fresh media every 3 days. Frequencies of CD11c$^+$ cells were ≥95%. To prepare primary splenic and mLN DCs, C57BL/6 mice were first injected subcutaneously in the right flank with 5×10$^6$ cells GM-CSF-expressing B16 melanoma (kindly provided by Jedd D. Wolchok, MSKCC). 10 days later, CD11c$^+$ cells were purified from Liberase TL (Roche)-digested spleen and mLN using CD11c positive selection beads (Miltenyi Biotec). Cell purities in the spleen were approximately 90% CD11c$^+$CD11b$^+$ of non-T and B cells. For intracellular bacterial survival assays, BMDCs were seeded on 6-well plates at 5×10$^6$ cells/well in antibiotic-free media and co-cultured with bacteria at an MOI of 50 for 2 hours, harvested and washed 3 times with sterile PBS. BMDCs were then plated in media containing gentamicin (100 µg/mL) at 200,000 cells/well on 48-well plates and lysed with sterile water every 48 hours to enumerate CFUs. For ELISA and qPCR, BMDCs were co-cultured with bacteria at an MOI of 50 for 2 hours and then gentamicin-treated to kill extracellular bacteria. Culture supernatants and cell lysates were harvested for ELISA and qPCR, respectively, 24 hours later. Heat killing was performed by incubating bacterial suspensions at 70° C. for 60 mins. For transmission electron microscopy, BMDCs colonized with *Bordetella* spp. for 5 days were harvested, processed and imaged using the Jeol-1010 transmission electron microscope. For microarray analysis, BMDCs were co-cultured with bacteria for 2 hours, washed extensively with PBS, incubated in media containing gentamicin (100 µg/mL) and lysed in TRIzol on day 4. All cell incubations were performed at 37° C. and 5% CO$_2$.

Immunofluorescent Detection of Intracellular Bacteria

BMDC-bacteria co-cultures were harvested on days 0, 2 and 5 and transferred to glass slides via cytospin. BMDCs were fixed with 4% PFA for 30 minutes at room temperature and stained with the Live/Dead BacLight Bacterial Viability Kit according to the manufacturer's instructions (Invitrogen). Cells were mounted with VectaShield mounting medium containing DAPI (Vector Laboratories) and imaged on the Nikon Eclipse Ti Fluorescence Inverted Microscope. PFA fixation did not affect the ability of the bacterial viability kit to distinguish between live and dead bacteria.

Gene Expression Profiling and Quantitative Real-Time PCR

RNA was isolated using TRIzol reagent (Life Technologies) according to the manufacturer's instructions. cDNA was generated using Superscript reverse transcriptase II (Invitrogen). Quantitative real-time PCR was performed using SYBR green chemistry (Invitrogen) and QuantiTect Primer Assays (Qiagen) on the ABI 7500 real-time PCR system (Applied Biosystems). Samples were normalized to β-actin and displayed as fold change over PBS-treated BMDCs or antibiotic-treated mice. For microarray analysis, BMDCs colonized with the LRC, *Bordetella* spp., for 4 days were lysed directly in TRIzol. RNA was isolated, amplified, reverse-transcribed to cDNA and hybridized to an Affymetrix GeneChip (Mouse Gene 1.0ST). Relative expression data was normalized by Z score transformation.

Histological Sections

Tissues from the small and large intestines were fixed with 4% PFA, embedded in paraffin, and 5 µm sections were cut and stained with H&E.

DSS-Induced Intestinal Damage

Mice were administered 2% DSS (MW 36,000-50,000, MP Biochemicals) in their drinking water ad libitum for the number of days indicated and then placed on regular drinking water. Disease severity was cumulatively scored based on rectal bleeding (out of 2), fecal consistency (out of 2), general appearance (out of 4), weight loss (out of 4) and rectal temperature (out of 4). For antibody treatments during DSS, mice were administered i.p. 500 µg/mouse of rat IgG, anti-IL22-01 (mouse neutralizing antibody developed by Pfizer) or anti-IL-10R (clone 1B1.3A, Bio X Cell) 1 day prior to DSS treatment, then on days 2, 5 and 7. Mice were sacrificed on day 8.

Statistical Analyses

Results represent mean±SEM and statistical analyses were performed by unpaired student's t-test, one- or two-way ANOVA with or without multiple comparisons tests as indicated in figure legends.

Data Accessibility

Sequenced microbial genome data are available at the European Nucleotide Archive under study number ERP012121. Array data are available at GEO under accession number GSE76731.

Flow Cytometry mLN and PP were harvested, and single-cell suspensions were prepared at necropsy. For small intestine lamina propria preparations, intestines were isolated, attached fat and PPs were removed and tissues were cut open longitudinally. Luminal contents were removed by shaking in cold PBS. Epithelial cells and intra-epithelial lymphocytes were removed by shaking tissue in stripping buffer (1 mM EDTA, 1 mM DTT and 5% FCS) at 37° C. for 30 minutes. The lamina propria layer was isolated by digesting the remaining tissue in 0.5 mg/mL collagenase/dispase (Roche) and 20 µg/mL DNase I (Sigma-Aldrich) for 30 minutes at 37° C. For flow cytometric analyses, cells were stained with antibodies against the following markers: anti-NK1.1 (clone PK136, eBioscience), anti-CD3 (clone 145-2C11, eBioscience), anti-CD5 (clone 53-7.3, eBioscience), anti-CD11c (clone N418, eBioscience), anti-CD4 (clone GK1.5, Abcam), anti-CD8a (clone 53-6.7, eBioscience), anti-B220 (clone RA3-6B2, eBioscience), anti-CD45 (clone 30-F11, eBioscience) and anti-CD11b (clone M1/70, eBioscience). For intracellular staining of RORγt, cells were fixed and permeabilized the Foxp3 intracellular staining buffer set (eBioscience) and stained with anti-RORγt (clone B2D, eBioscience). For intracellular cytokine staining, cells were stimulated ex vivo by incubation for 4 h with 50 ng/mL PMA, 750 ng/mL ionomycin, 10 μg/mL Brefeldin A (all obtained from Sigma-Aldrich) and 50 ng/mL rmIL-23 (eBioscience) and permeabilized as indicated above and stained with anti-IL-17A (clone eBioTC11-18H10.1, eBioscience), anti-IFN-γ (clone XMG1.2, eBioscience) and anti-IL22-02 (mouse cytokine detection antibody developed by Pfizer). Dead cells were excluded from analysis using the Live/Dead Aqua Viability Kit (Invitrogen). Flow cytometry data collection was performed on the LSR II (BD Biosciences). Data were analyzed using FlowJo software (Tree Star Inc.).

Histological Sections

Tissues from the small and large intestines were fixed with 4% PFA, embedded in paraffin, and 5 μm sections were cut and stained with H&E.

DNA Preparation, Sequencing, Assembly, and Annotation.

DNA was prepared and sequenced using the Illumina Hi-Seq platform with library fragment sizes of 200-300 bp and a read length of 100 bp at the Wellcome Trust Sanger Institute, as previously described (Harris et al., 2010, Science 327, 469-474). De novo assembly of 32 genomes was performed with Velvet v. 1.2.10 (Zerbino, 2008, Genome research 18, 821-829), SSPACE v. 2.0 (Boetzer et al., 2011,) and GapFiller v 1.1 (Boetzer, et a., 2012, Bioinformatics (Oxford, England) 27, 578-579) using an in-house pipeline developed at the Wellcome Trust Sanger Institute. De novo assemblies were annotated with Prokka v. 1.5-1 (Seemann, 2014, Bioinformatics (Oxford, England) 30, 2068-2069) using an in-house pipeline developed at the Wellcome Trust Sanger Institute, which is available on GitHub (sanger-pathogens/Bio-automatedannotation).

Phylogenetic Analysis

The fetchMG v. 1.0 was used to extract the protein information based on 40 universal single copy marker genes (Ciccarelli et al., 2006, Science 311, 1283-1287; Sorek et al., 2007, Science 318, 1449-1452) from each of the studied genome including 32 draft genomes and 15 reference genomes (Table 1). The protein sequences were then concatenated and aligned with MAFFT v. 7.205 (Katoh et al., 2013, Molecular biology and evolution 30, 772-780), and a maximum-likelihood tree was constructed using RAxML v. 7.8.6 (Stamatakis, 2006, Bioinformatics (Oxford, England) 22, 2688-2690) with 100 bootstrap replicates under the Gamma+WAG model. The tree was visualized using SplitsTree v. 4.13.1 (Huson et al., 2006, Molecular biology and evolution 23, 254-267).

Results

Lymphoid Tissue-Resident Commensal Bacteria Colonize Murine Dendritic Cells

We constructed a phylogenetic tree using in-house sequenced and publically available reference genomes of α-, β-, γ-proteobacteria and Bacteroidia members (Table 1).

Table 1. List of publically available reference genomes used in this study (Related to FIGS. 1A-1F).

TABLE 1

List of publically available reference genomes used in this study (Related to FIGS. 1A-1F).

| Strains | Accession No. |
|---|---|
| Achromobacter xylosoxidans A8 | CP002287 |
| Achromobacter xylosoxidans ATCC 27061 | CP006958 |
| Achromobacter xylosoxidans C54 | CP009448 |
| Achromobacter xylosoxidans NH44784-1996 | HE798385 |
| Alcaligenes faecalis subsp. faecalis NCIB 8687 | NZ_AKMR01000001.1 |
| Alistipes shahii WAL 8301 | FP929032.1 |
| Bacteroides fragilis NCTC 9343 | CR626927.1 |
| Bacteroides thetaiotaomicron VPI-5482 | AE015928.1 |
| Bordetella holmesii ATCC 51541 | CP007494 |
| Bordetella hinzii ATCC 51730 | NZ_AWNM01000071.1 |
| Escherichia coli str. K-12 substr. MG1655 | U00096.3 |
| Ochrobactrum anthropi ATCC 49188 | CP000758.1 |
| Ochrobactrum anthropi OAB | CP008820.1 |
| Ochrobactrum intermedium LMG 3301 | NZ_ACQA01000001.1 |
| Rikenella microfusus DSM 15922 | NZ_KE386488.1 |

Phylogenetic analyses indicated that members of the α-proteobacteria and β-proteobacteria LRCs form two distinct clades from γ-proteobacteria and Bacteroidia members, which are typically found in the lumen of the intestine and not associated with intestinal lymphoid tissues in healthy mammals (FIG. 1A).

Figure 1B:
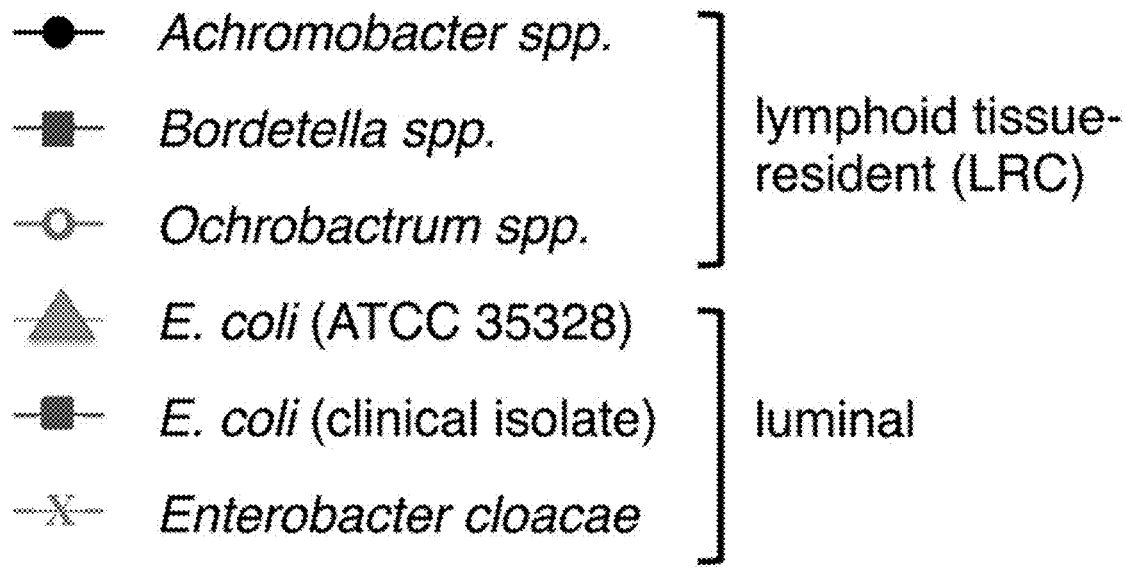
Figure 1B:
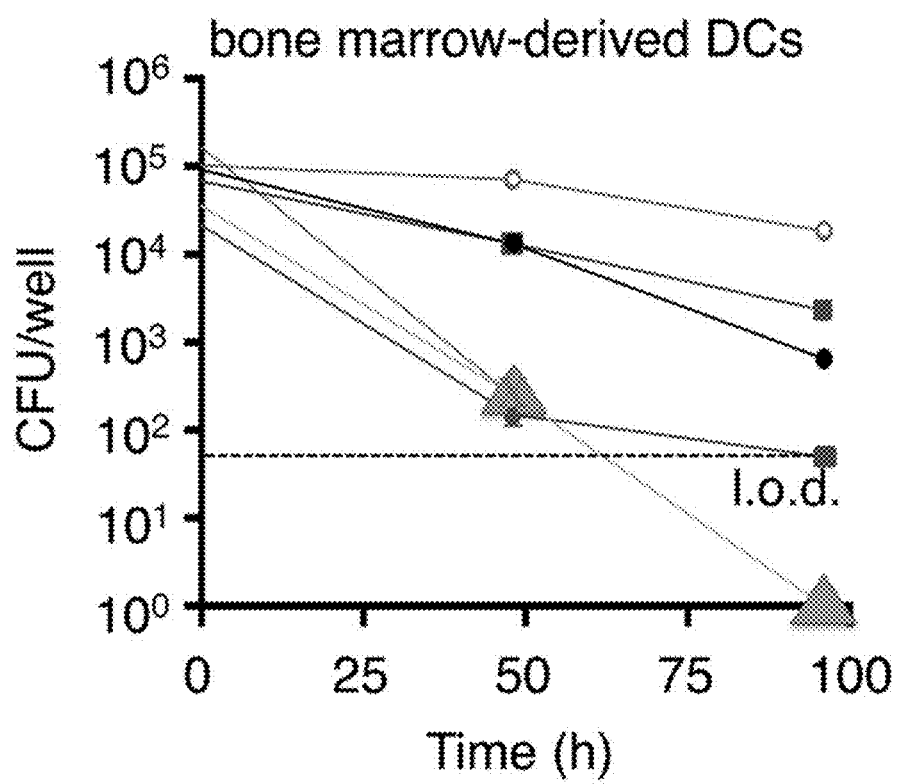
Figure 1C:
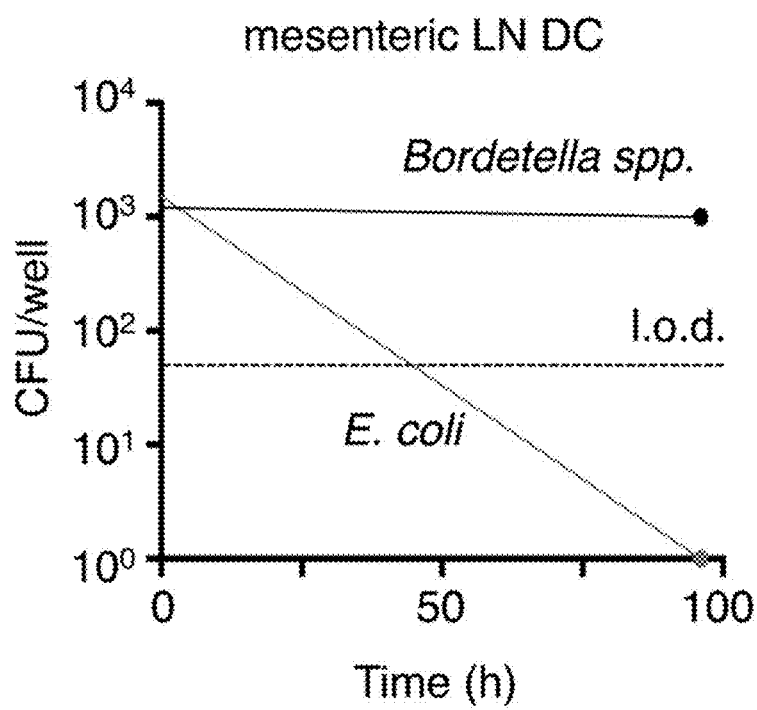
Figure 1D:
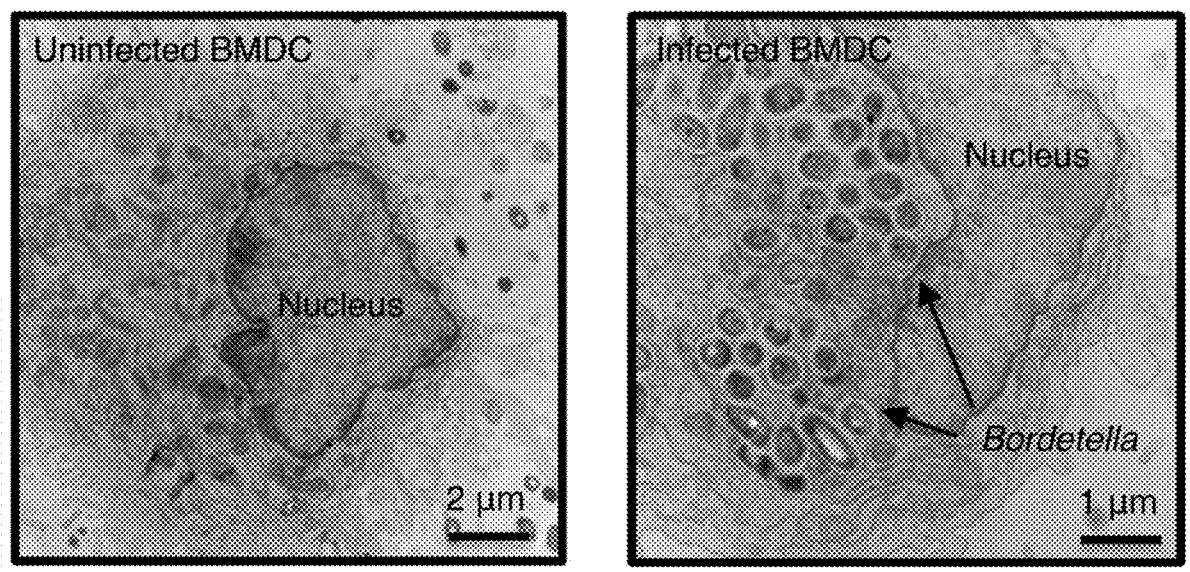
Figure 1E:
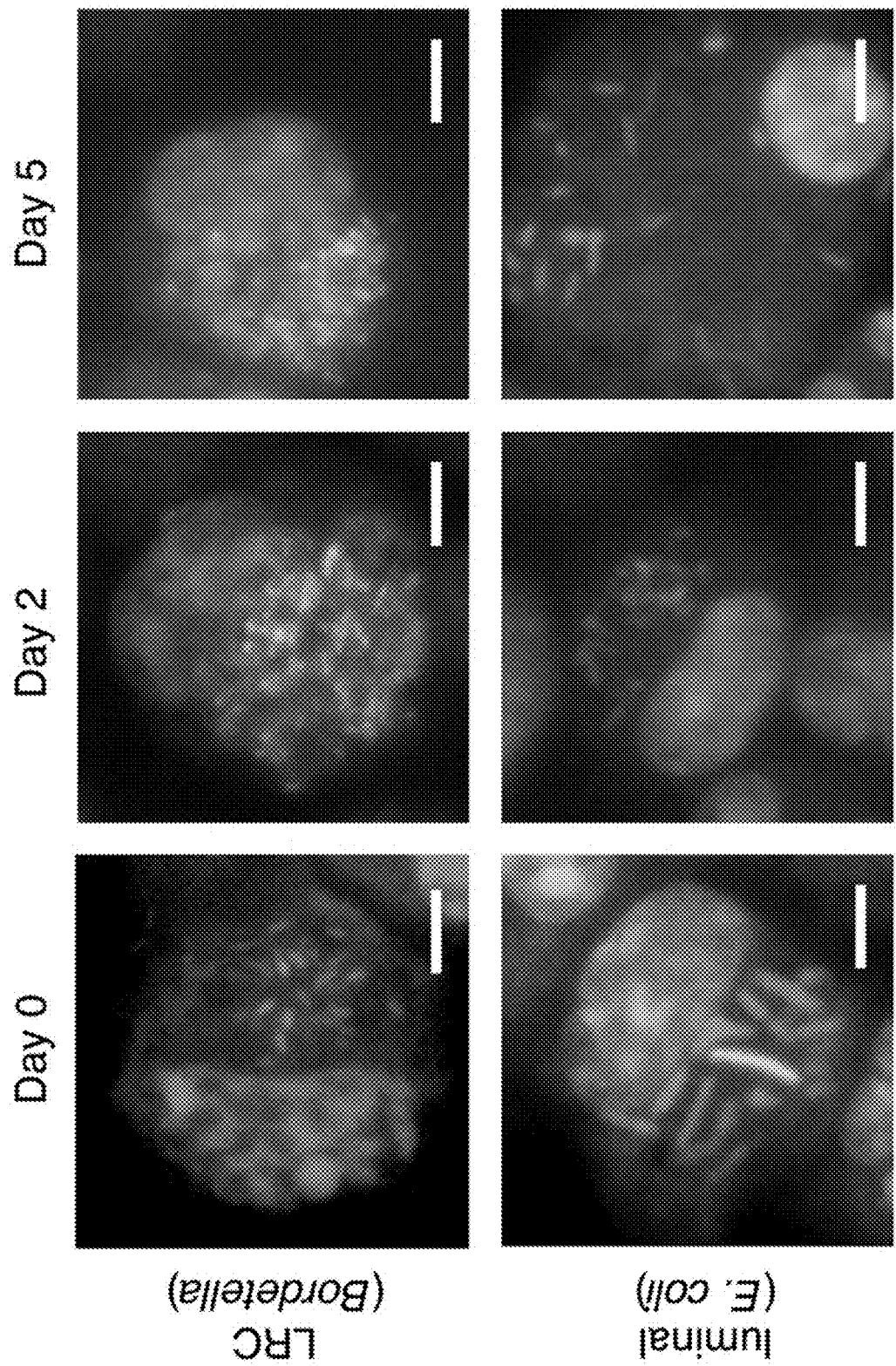
Figure 1F:
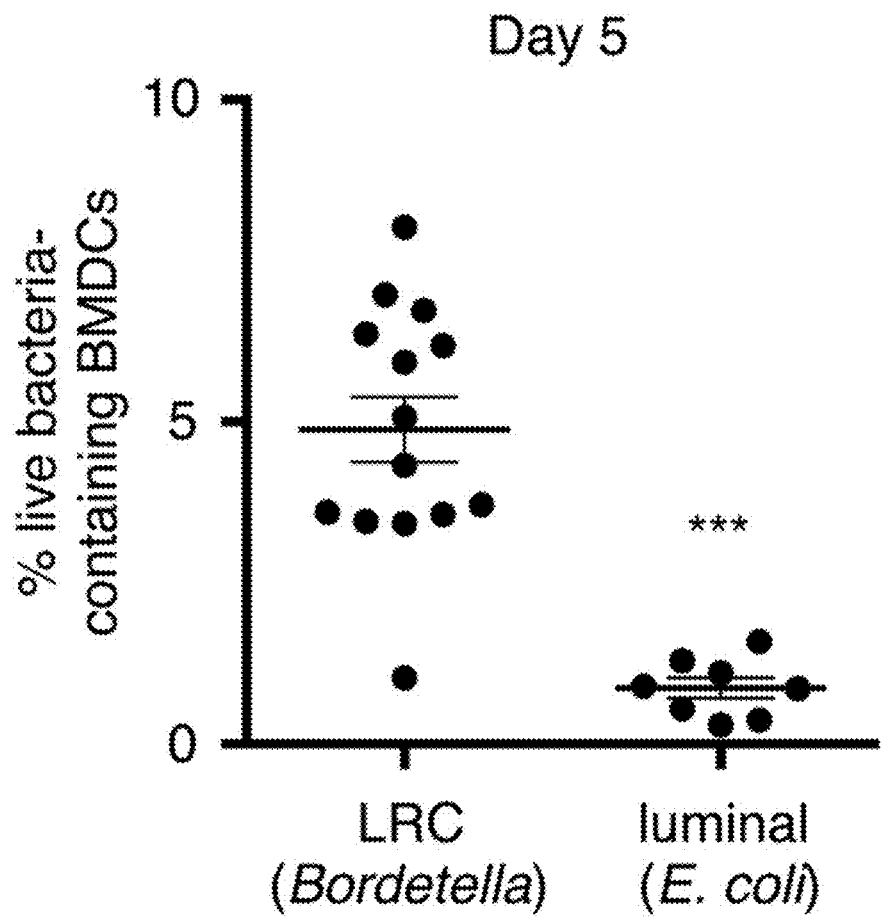
Figure 7A:
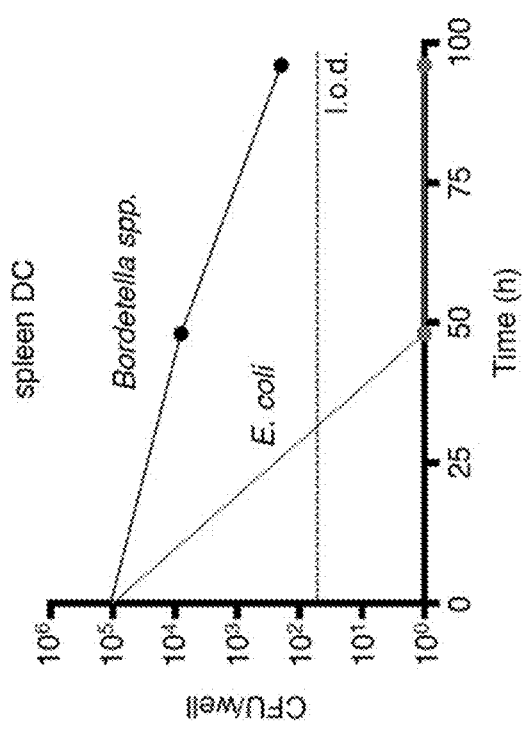
FIGS. 7A and 7B. Lymphoid tissue-resident commensal bacteria colonize primary splenic DCs and induce DC cytokine responses (Related to FIGS. 1A-1F). (A) Primary DCs isolated from the spleen of C57BL/6 mice were co-cultured with the mouse-derived LRC, *Bordetella* spp. or luminal-resident commensal, *E. coli* ATCC 35328, and bacterial survival was measured at 0, 48 and 96 hours. l.o.d., limit of detection. (B) Production of IL-1β, IL-6, IL-10 and IL-12p40 was measured in supernatants from *Bordetella*- or E. coli-spleen DC co-cultures at 96 h post-co-culture. Data representative of 2 independent experiments.

To test if LRCs may colonize DCs, bone marrow-derived DCs (BMDCs) were co-cultured with bacteria predicted to be LRCs or representative intestinal microbes not predicted to be LRCs (non-LRCs), and the ability of each bacterium to survive in DCs was determined using a gentamicin protection assay. LRCs and non-LRCs were both internalized by DCs, but the numbers of viable non-LRCs declined rapidly within the first 3 days of culture, while viable LRCs persisted at high levels on days 2 and 4 (FIG. 1B). LRCs but not non-LRCs were also able to colonize primary DCs isolated from the mLN and spleen (FIGS. 1C and 7A). Transmission electron microscopy demonstrated intracellular colonization of DCs by LRCs as noted by the presence of dense bacterial clusters within intracellular vesicles (FIG. 1D), and an immunofluorescence assay confirmed the presence of intracellular live LRCs on days 2 and 5 post colonization (FIG. 1E-F). Together, these data suggest that, in contrast to luminal-resident commensal bacteria, LRCs have the ability to efficiently colonize and persist in murine DCs.

Figure 2A:
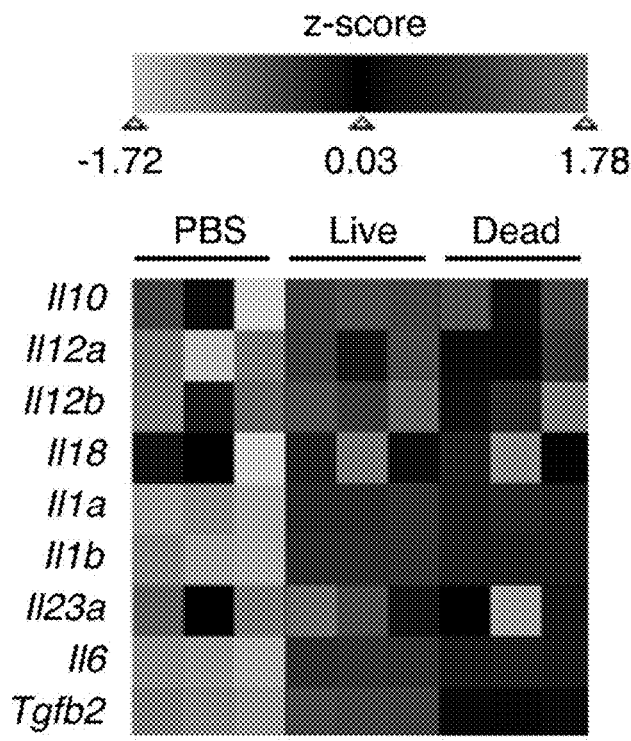
FIGS. 2A-2C. Lymphoid tissue-resident commensal bacteria modulate cytokine responses in bone marrow-derived dendritic cells in a viability-dependent manner. (A) Genome-wide transcriptional profiling was performed on BMDCs co-cultured with live or heat-killed *Bordetella* spp. for 4 days. Numbers in legend represent Z scores. (B) BMDCs co-cultured with live or heat-killed *Bordetella* spp. for 24 hours were analyzed for cytokine gene expression by qPCR. (C) BMDCs co-cultured with live or heat-killed *Bordetella* spp. for 24 hours were analyzed for cytokine protein secretion by ELISA. qPCR and ELISA data were representative of at least 2 independent experiments. Data are represented as mean±SEM. Statistics shown in B and C were performed using unpaired, two-tailed, student's t test. *, p<0.05; , p<0.01; *, p<0.001; ****, p<0.0001. See also FIGS. 8A and 8B FIG. 8.
Figure 2B:
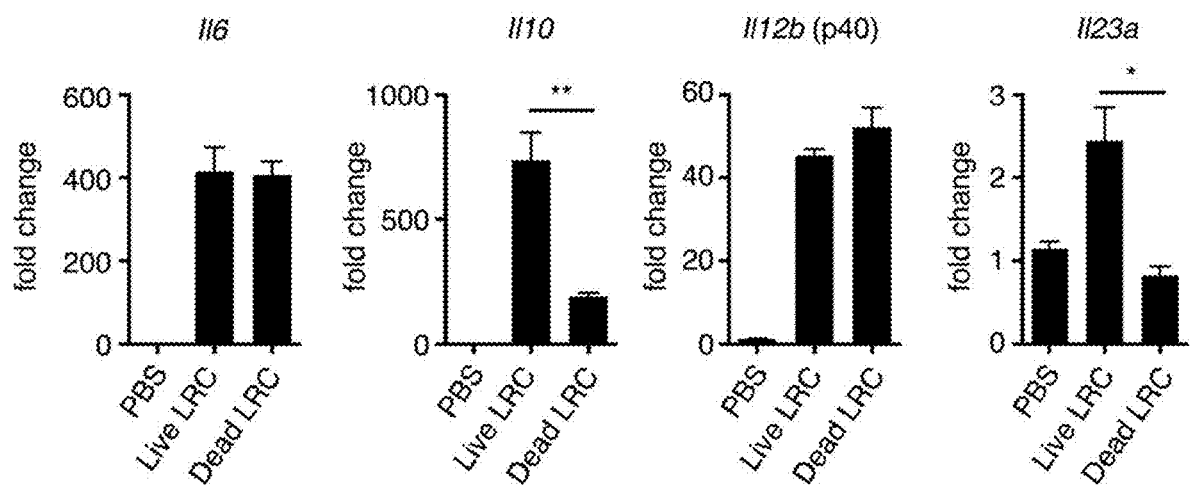
Figure 2C:
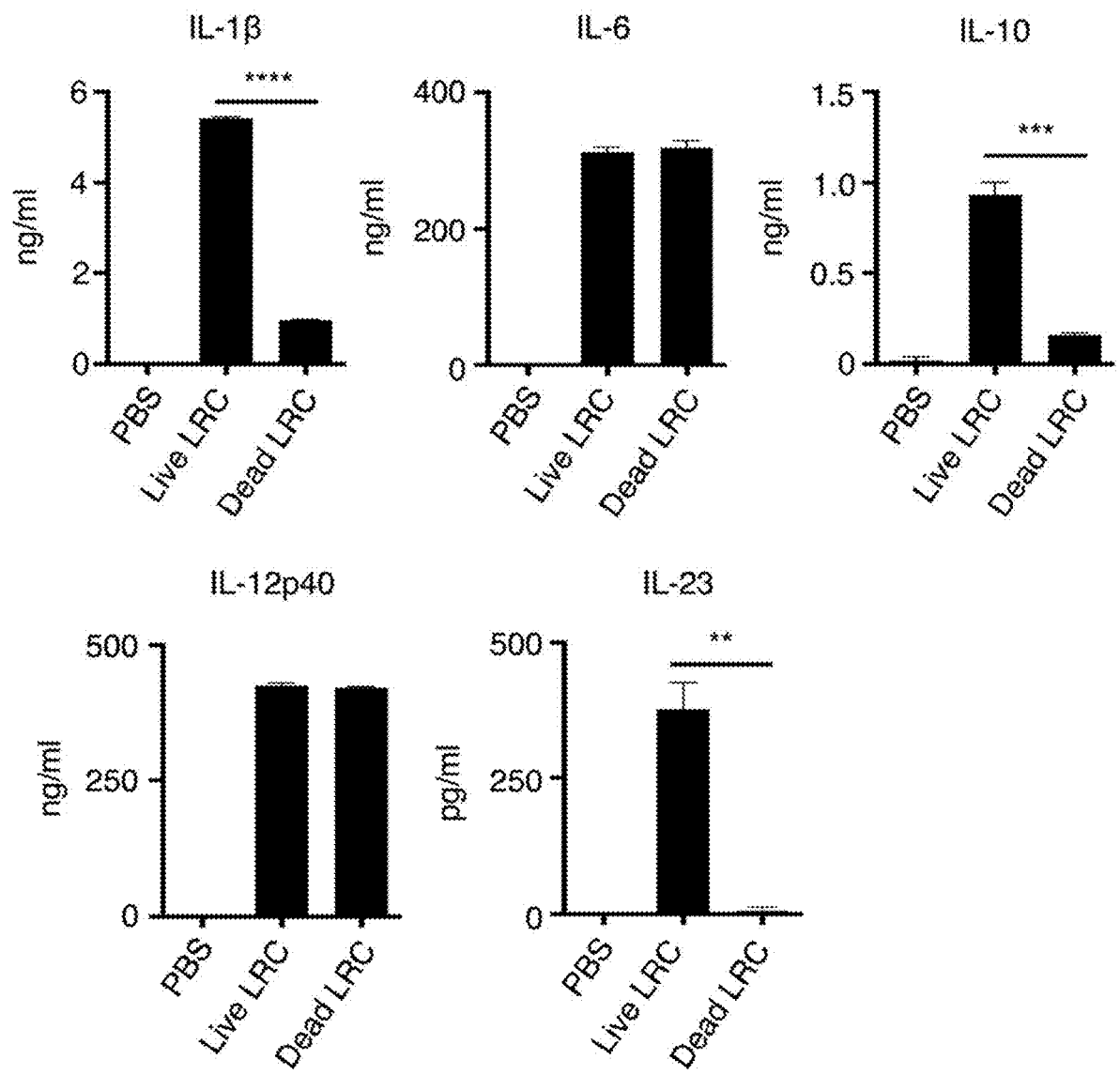
Figure 7B:
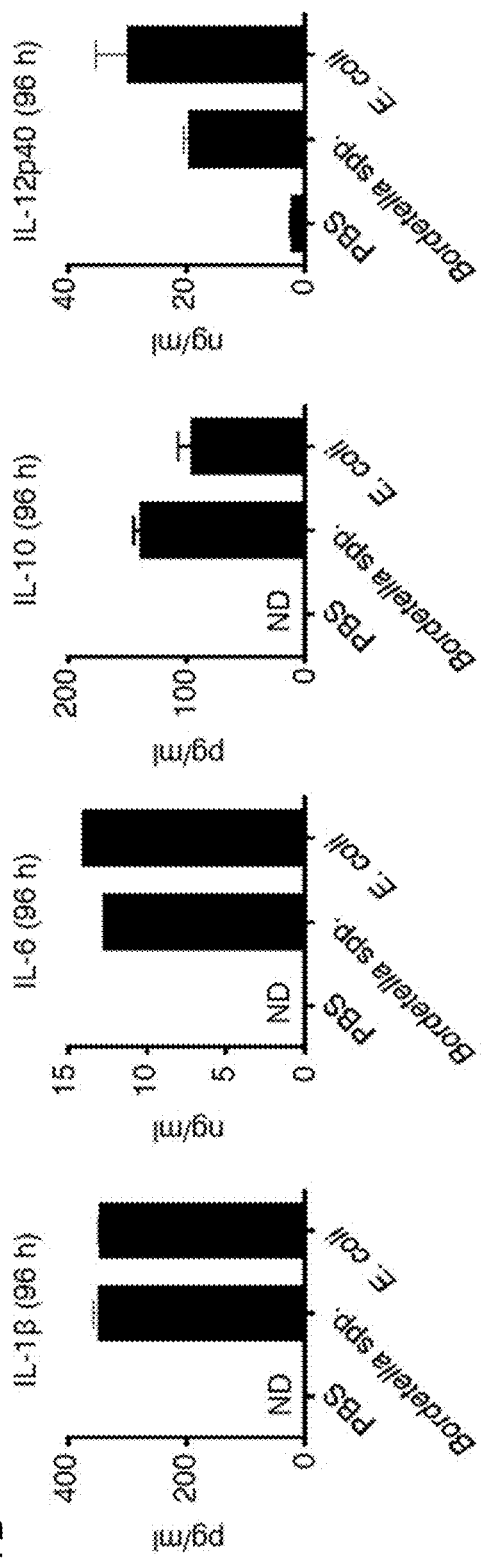
Figure 8A:
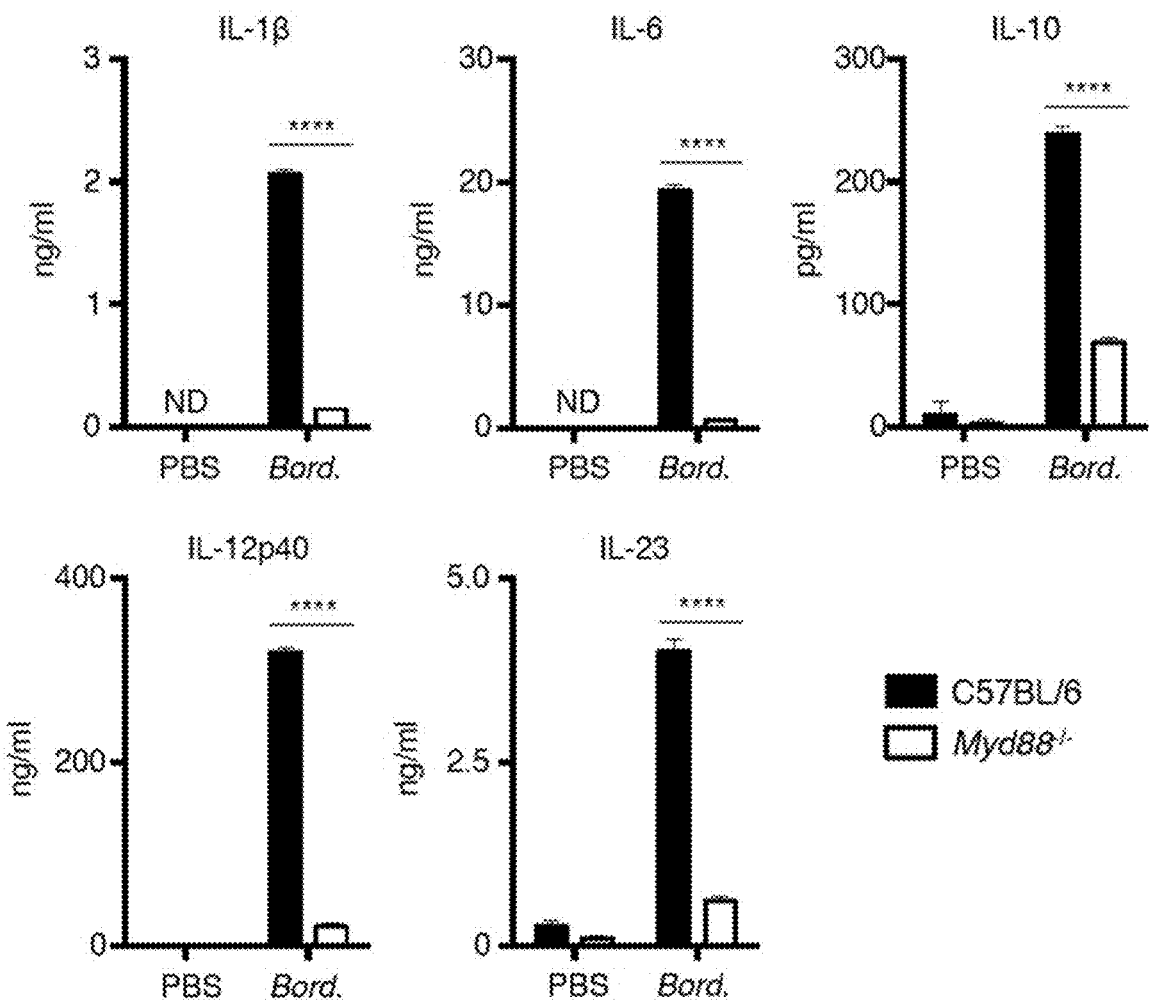
FIGS. 8A and 8B. Lymphoid tissue-resident commensal bacteria promote DC cytokine production in a MYD88-dependent manner (Related to FIGS. 2A-2C). (A) C57BL/6 and Myd88$^{-/-}$ BMDCs were exposed to PBS or Bordetella spp. for 24 hours and production of IL-1β, IL-6, IL-10, IL-12p40 and IL-23 was measured in the culture supernatant. (B) C57BL/6, Tlr2$^{-/-}$ and Tlr4$^{-/-}$ BMDCs were exposed to PBS or Bordetella spp. for 24 hours and production of IL-1β and IL-23 was measured in the culture supernatant. Data representative of 2 independent experiments. Statistics were performed using two-way ANOVA with Sidak's multiple comparisons test. ****, $p<0.0001$.
Figure 8B:
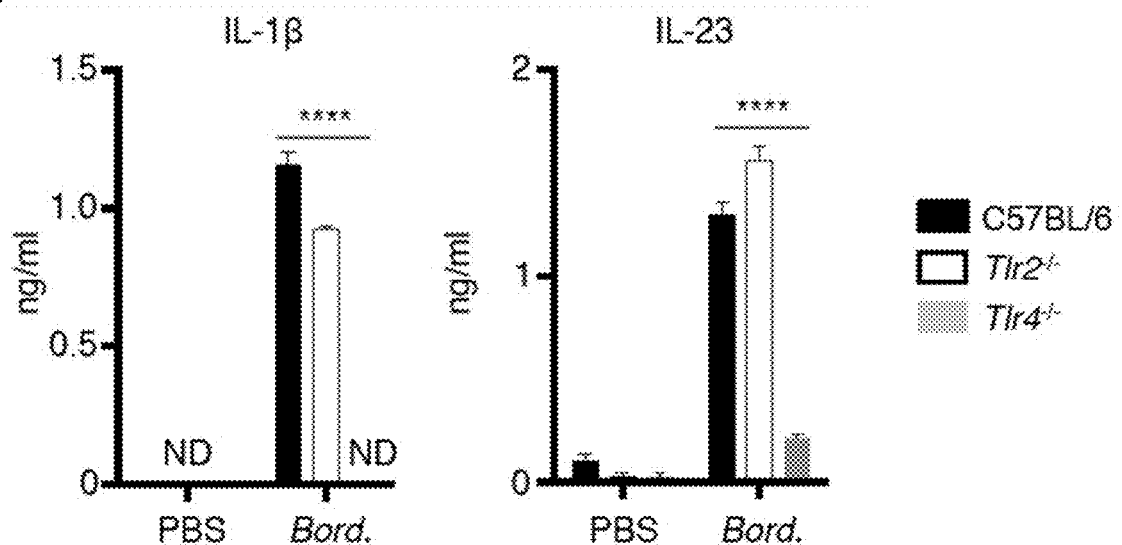

Lymphoid Tissue-Resident Commensal Bacteria Modulate Dendritic Cell Cytokine Production in a Viability-Dependent Manner Based on the ability of LRCs to colonize and persist in murine DCs, we sought to characterize DC cytokine induction following exposure to live versus heat-killed LRCs. To investigate this, genome-wide transcriptional profiling was performed on DCs treated with PBS, live or heat-killed Bordetella spp., a model LRC isolated from our mouse colony, at 4 days post-colonization. Analysis of canonical DC-derived cytokines revealed that DCs colonized with live LRCs expressed greater levels of both pro- and anti-inflammatory cytokines Il6, Il23a, Il18, Il12a, Il12b, Il10 and Tgfb2 as compared with PBS-treated DCs (FIG. 2A). Notably, the induction of mRNA and protein for several of these cytokines, including IL-10, IL-6, IL-10, IL-12p40 and IL-23, by live LRCs was detected as early as 24 hours post co-culture (FIGS. 2B and 2C), and the induction of IL-10 and IL-23 mRNA (FIGS. 2A and 2B) and secretion of IL-1β, IL-10 and IL-23 protein (FIG. 2C) did not occur in DCs exposed to only heat-killed LRCs, suggesting that viability-dependent factors expressed by LRCs induce selective DC cytokine responses. Primary splenic DCs exposed to live LRCs also produced IL-1β, IL-6, IL-10 and IL-12p40 (FIG. 7B). Efficient induction of both viability-(IL-1β, IL-10, IL-23) and non-viability-dependent cytokines (IL-6, IL-12p40) required MYD88, suggesting a role for Toll-like receptors (TLRs) in recognition of LRCs (FIG. 8A). Consistent with this, production of IL-1β and IL-23 was significantly reduced in Tlr4$^{-/-}$ but not Tlr2$^{-/-}$ BMDCs (FIG. 8B). Collectively, these data indicate that LRC colonization of DCs induces distinct pro- and anti-inflammatory cytokine responses in a viability- and TLR-dependent manner.

Figure 3A:
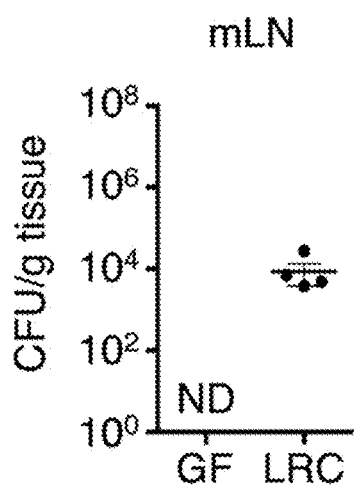
FIGS. 3A-3K. Colonization of intestinal-associated lymphoid tissues by lymphoid tissue-resident commensal bacteria modulates local Th17 cell responses. (A) Mesenteric lymph nodes (mLN) homogenates, (B) Peyer's patches (PP) homogenates and (C) small intestinal lumen contents from GF and *Bordetella* spp. (LRC)-monocolonized mice were cultured determine bacterial CFUs. Data in (A) and (B) are representative of at least 2 independent experiments. (D) mLN, (E) PP and (F) small intestine lamina propria (SI LP) of conventionally-housed (CNV), GF, SFB-monocolonized and LRC-monocolonized mice were analyzed for frequencies of IL-17A$^+$ and IFN$\gamma^+$ CD4$^+$ T cells by flow cytometry. (G) Frequencies of Th17 cells in CNV, GF, SFB-monocolonized and LRC-monocolonized mice. Values represent frequencies of IL-17A$^+$ cells among CD4$^+$ T cells. One-way ANOVA, mLN and SI LP—**p<0.0001; PP—p<0.01 (H and I) PPs of CNV, GF, SFB-monocolonized and LRC-monocolonized mice were analyzed for frequencies of IL-22-producing Th17 cells by flow cytometry. Values represent frequencies of IL-22$^+$ cells of IL-17A$^+$ CD4$^+$ T cells. One way ANOVA, mLN—**p<0.0001; PP—p<0.01; SI LP—*p<0.05. Data are pooled from 2 independent experiments for a total of 6-8 mice per group. (J and K) Frequencies of Th17 cells (gated as CD3$^+$CD4$^+$ROR$\gamma$t$^+$ FOXP3$^-$) in the mLN of LRC-monocolonized Il10$^{+/+}$ or Il10$^{-/-}$ mice. Data representative of 2 independent experiments with 2-5 mice per group using Il10$^{-/-}$ monocolonized mice or C57BL/6 monocolonized mice with anti-IL-10R treatment (500 μg/mouse i.p. every 3 days, analyzed on day 7). One-way ANOVA, ****p<0.0001. Cells in all flow cytometry plots are gated as live, CD3$^+$ and CD4$^+$. Data are represented as mean±SEM. Statistics shown in panels G, I and K were performed using one-way ANOVA with unpaired, two-tailed, student's t test with no correction for multiple comparisons. *, p<0.05; , p<0.01; *, p<0.001. ND, not detectable. See also FIGS. 9A-9E FIG. 9.
Figure 3B:
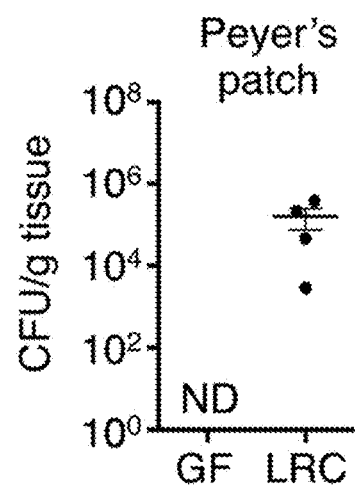
Figure 3C:
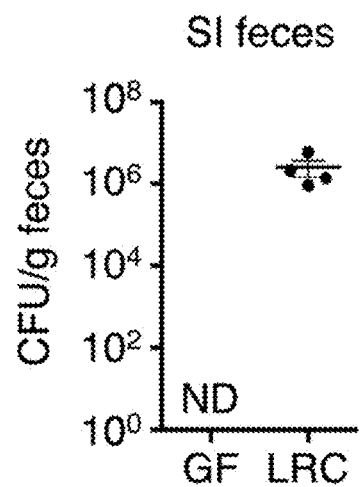
Figure 9A:
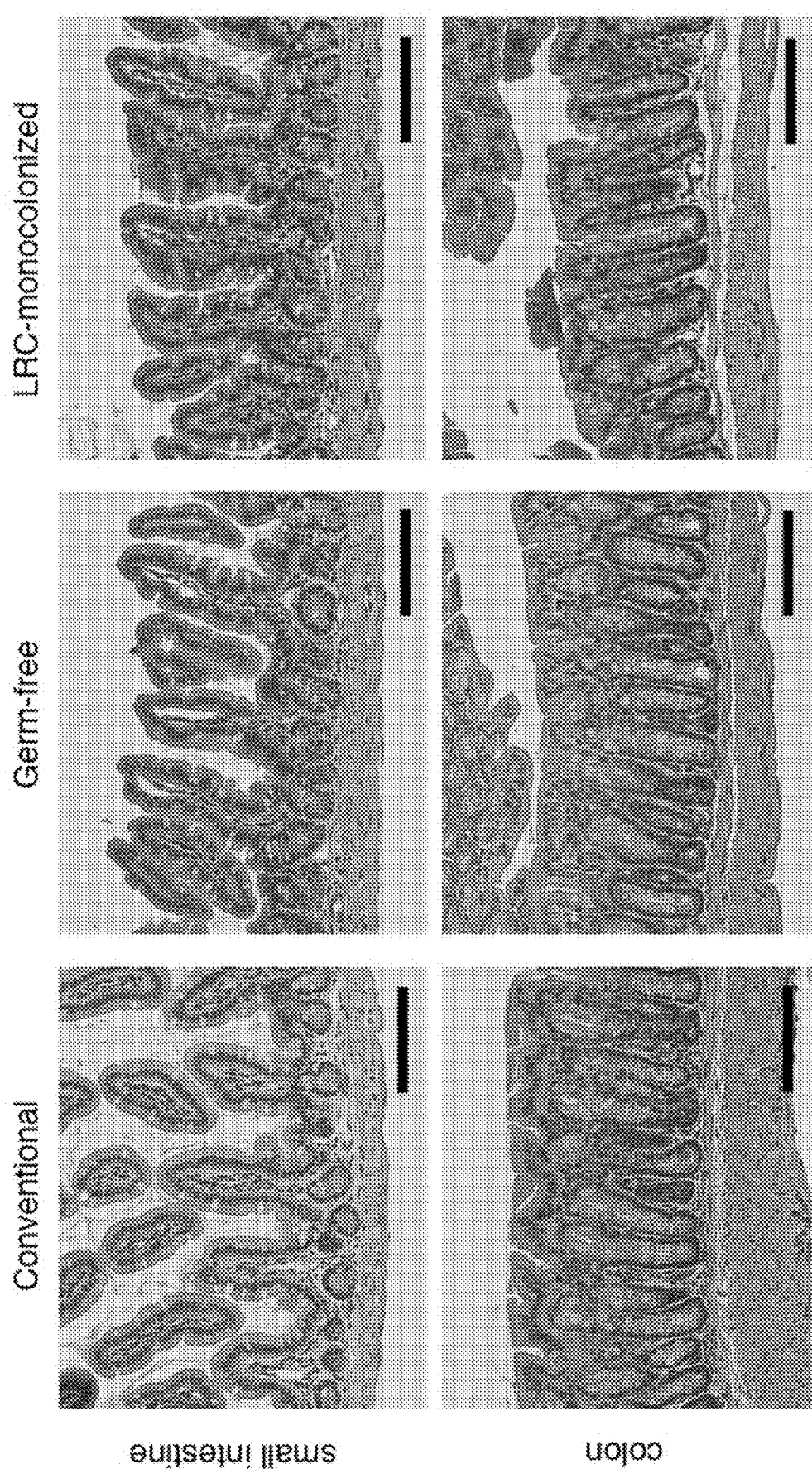

Lymphoid Tissue-Resident Commensal Bacteria Promote Tissue-Specific Th17 Cell Responses To test whether these LRCs can stably colonize and survive in intestinal-associated lymphoid tissues, germ-free (GF) mice were monocolonized with *Bordetella* spp., a model LRC isolated from our mouse colony. At day 10 post-inoculation, viable LRCs were consistently detected in the mLN (FIG. 3A), PPs (FIG. 3B) and fecal contents of the intestinal lumen (FIG. 3C), but not the spleen and liver. However, colonization by LRCs was not associated with macroscopic or microscopic inflammation in the intestine at 2 weeks post colonization (FIG. 9A). These data support the hypothesis that LRCs can colonize and persist in intestinal-associated lymphoid tissues of healthy mammals.

Figure 3D:
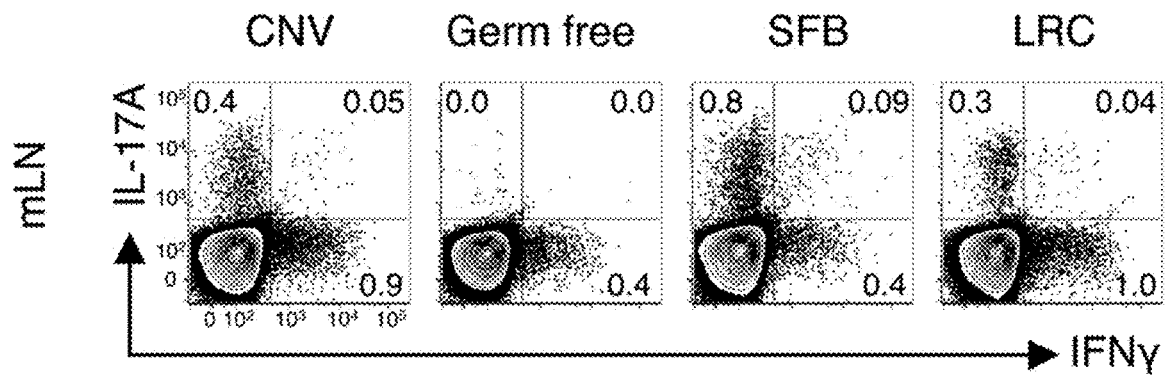
Figure 3E:
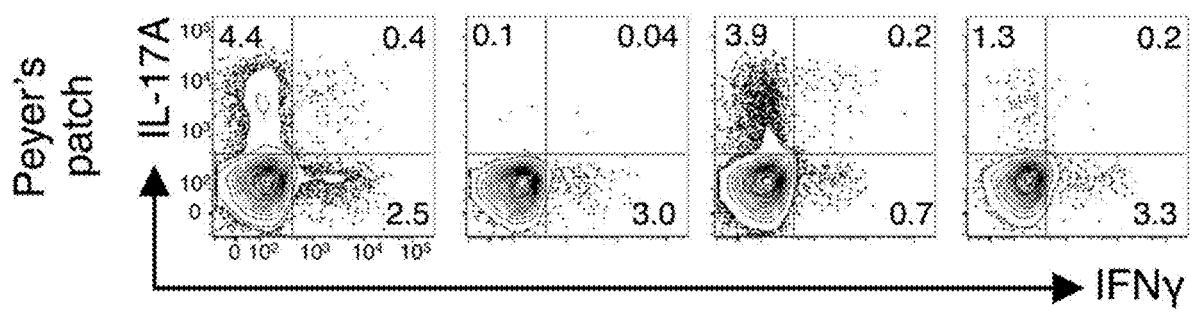
Figure 3F:
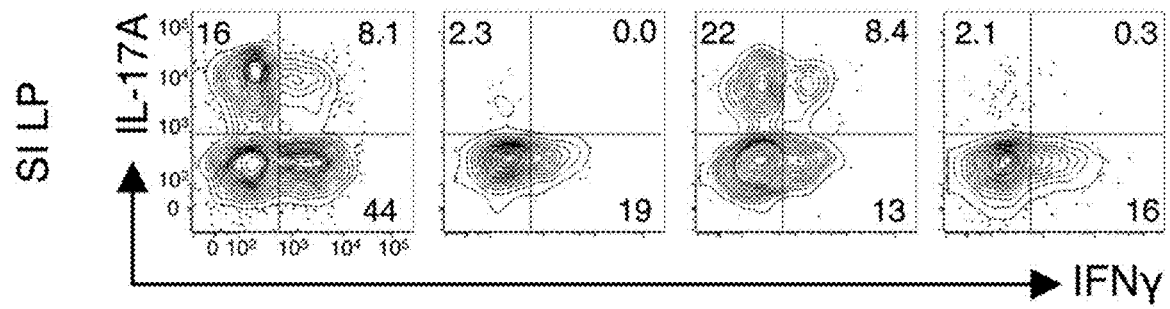
Figure 3G:
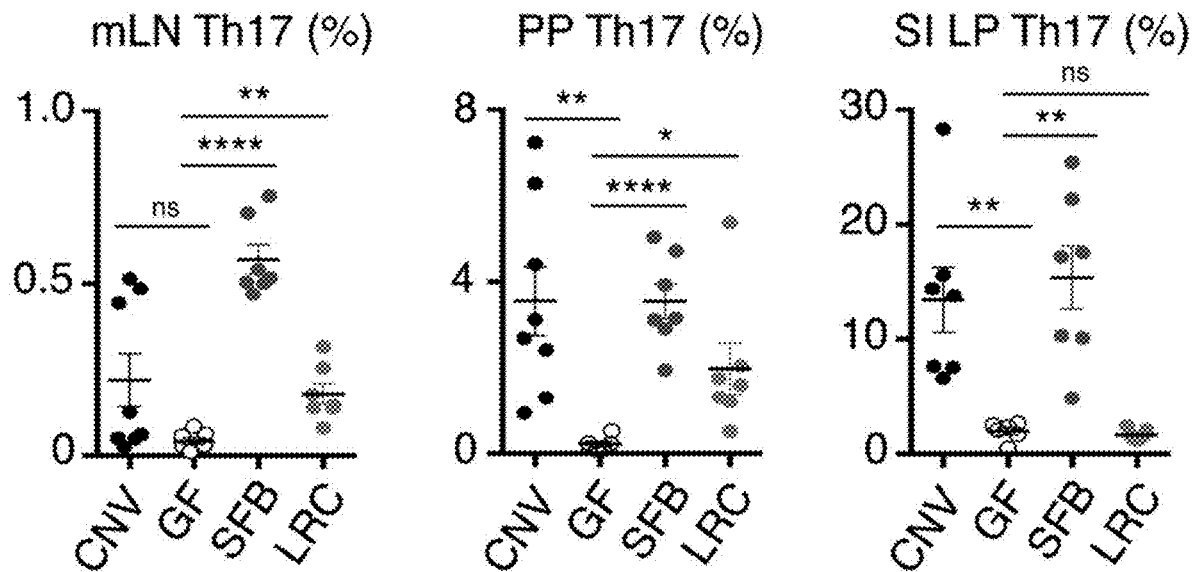
Figure 3H:
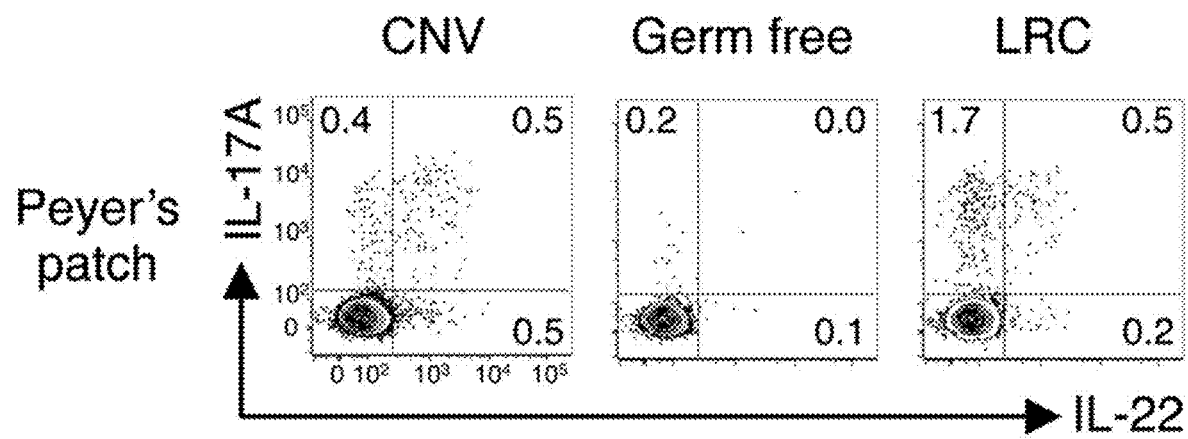
Figure 3I:
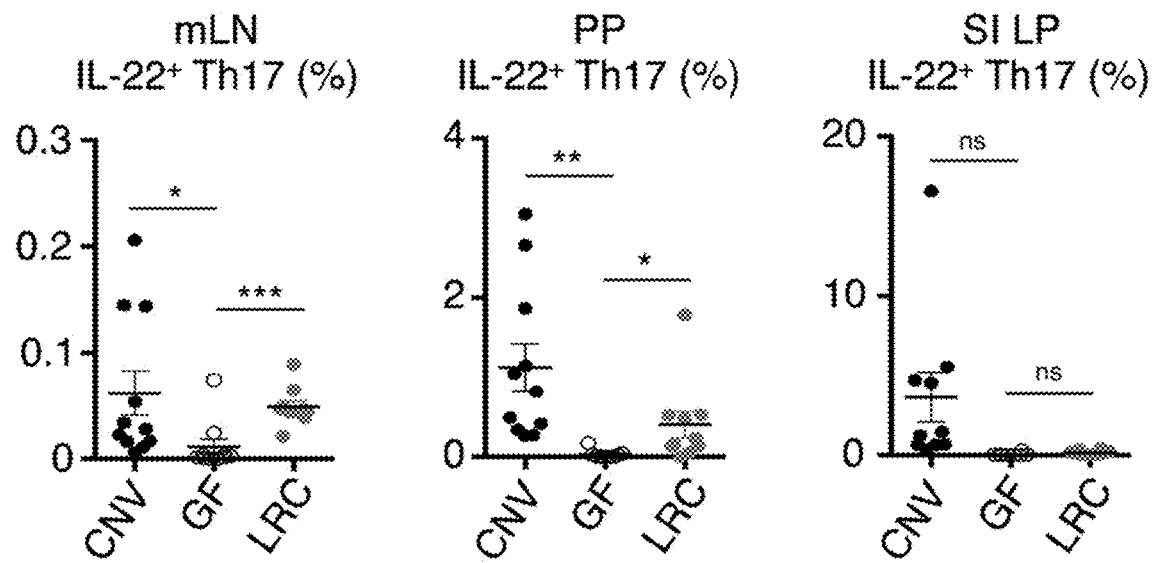
Figure 3J:
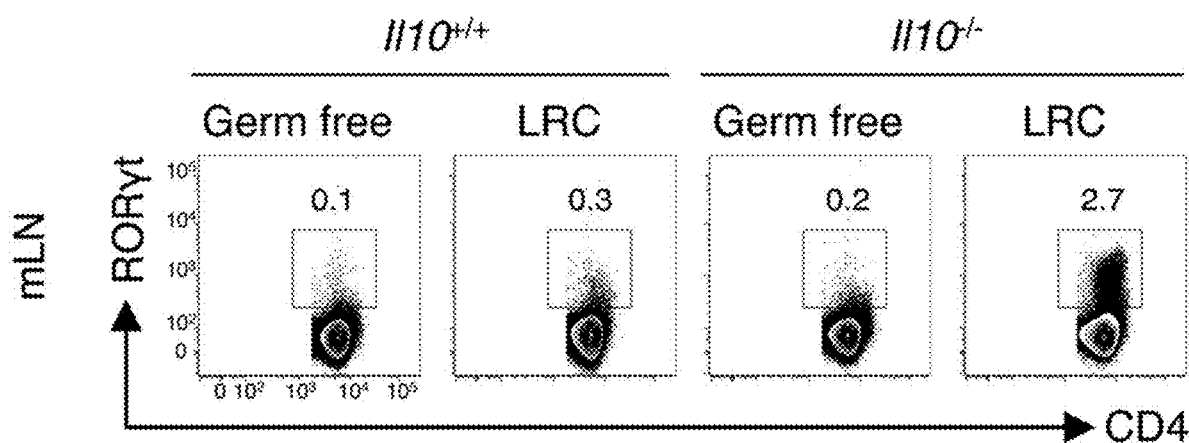
Figure 3K:
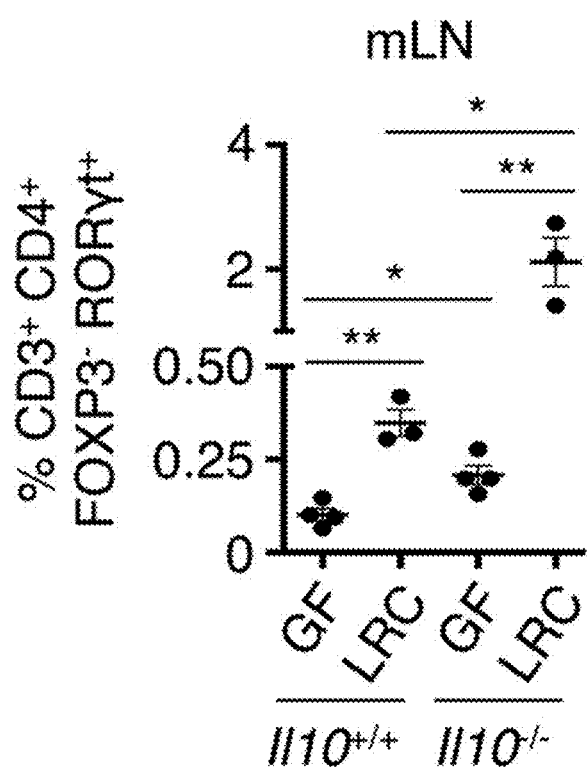

To test if LRCs promote Th17 cell responses in colonized lymphoid tissues, we analyzed CD4$^+$ T cells in the PP, mLN and small intestine lamina propria (SI LP) of conventionally-housed (CNV), GF, LRC-monocolonized mice, as well as mice monocolonized with segmented filamentous bacteria (SFB), an epithelial-associated commensal bacterium which has previously been shown to induce robust Th17 cell responses (Gaboriau-Routhiau et al., (2009), Immunity 31, 677-689). We observed that GF mice lacked Th17 cells in the mLN (FIG. 3D), PP (FIG. 3E) and SI LP (FIG. 3F) compared to CNV mice, and SFB was sufficient to promote robust Th17 cell responses in these tissues. In contrast, LRCs promoted Th17 cell responses in the mLN and PP (FIGS. 3D, 3E and 3G) but failed to promote Th17 cell responses in the SI LP, suggesting tissue-specific modulation of the immune system (FIG. 3F-G). Analysis of LRC-elicited Th17 cells in the PP revealed co-expression of the IL-10 family cytokine, IL-22 (FIGS. 3H and 3I). Accumulation of Th17 cells was selective, as LRCs did not significantly promote IFNγ-producing Th1 cell responses in the mLN, PP or SI LP (FIG. 9B). Although significant Th17 cell responses were observed in the PP and mLN of LRC-monocolonized mice, the magnitude of these responses was lower than that observed in SFB-monocolonized mice (FIG. 3D-F), suggesting that LRCs are less efficient at inducing Th17 cell responses or are actively suppressing Th17 cell responses. Since LRCs could promote IL-10 by DCs in vitro (FIGS. 2A-C and 7B) and IL-10 has been shown to suppress Th17 cell responses (Liu et al., 2011, Gastroenterology 141, 653-662, 662.e651-654; McGeachy et al., 2007, Nature immunology 8, 1390-1397; Ouyang et al., 2011, Annual review of immunology 29, 71-109), we tested if IL-10 restrain LRC-induced Th17 cells. We observed that Th17 cells were significantly increased in the mLN (FIGS. 3J and 3K) and PP (FIGS. 9C and 9D) of LRC-monocolonized Il10$^{-/-}$ mice compared to LRC-monocolonized Il10$^{+/+}$ mice. Thus, LRCs selectively promote local Th17 cell responses in intestinal-associated lymphoid tissues, and the magnitude of these responses is limited by co-induction of IL-10.

Figure 4A:
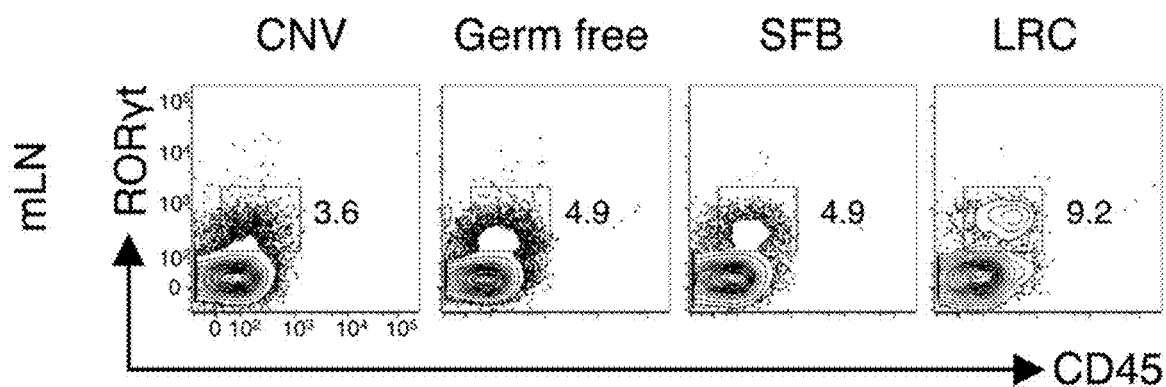
FIGS. 4A-4E. Colonization of intestinal-associated lymphoid tissues by lymphoid tissue-resident commensal bacteria promotes local ILC3 responses. (A) mLN, (B) PP and (C) SI LP of CNV, GF, SFB-monocolonized and *Bordetella* (LRC)-monocolonized mice were analyzed for frequencies of ILC3 cells by flow cytometry. Cells in (A) were gated as live, lineage$^-$ (CD3$^-$, CD5$^-$, CD8α, CD11b$^-$, B220$^-$, NK1.1$^-$). Cells in (B) and (C) were gated as live, CD45$^+$ and lineage$^-$. (D) Quantification of ILC3 frequencies in the mLN, PP and SI LP of CNV, GF, SFB-monocolonized and LRC-monocolonized mice. mLN ILC3 values represent frequencies of CD45$^+$ROR$\gamma$t$^+$ of lineage$^-$ cells. PP and SI LP ILC3 values represent frequencies of CD90$^+$ROR$\gamma$t$^+$ of lineage$^-$ cells. One-way ANOVA, mLN—****p<0.0001; PP—*p<0.05; SI LP—**p<0.01. (E) PPs of CNV, GF, SFB-monocolonized and LRC-monocolonized mice were analyzed for frequencies of IL-22$^+$ ILC3 cells by flow cytometry. Cells are gated as live, lineage$^-$, CD90$^+$ and ROR$\gamma$t$^+$ Data are pooled from 2 independent experiments for a total of 6-8 mice per group. Data are represented as mean±SEM. Statistics shown in panel D were performed using one-way ANOVA with uncorrected Fisher's LSD test. *, p<0.05; , p<0.01; *, p<0.001.
Figure 4B:
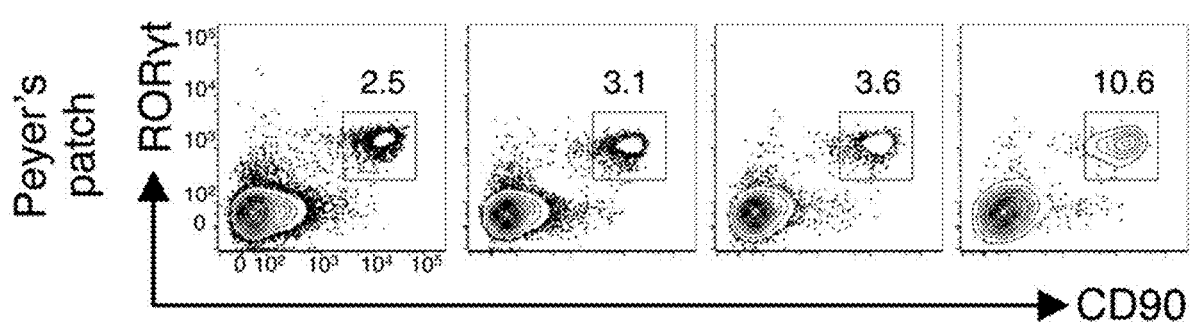
Figure 4C:
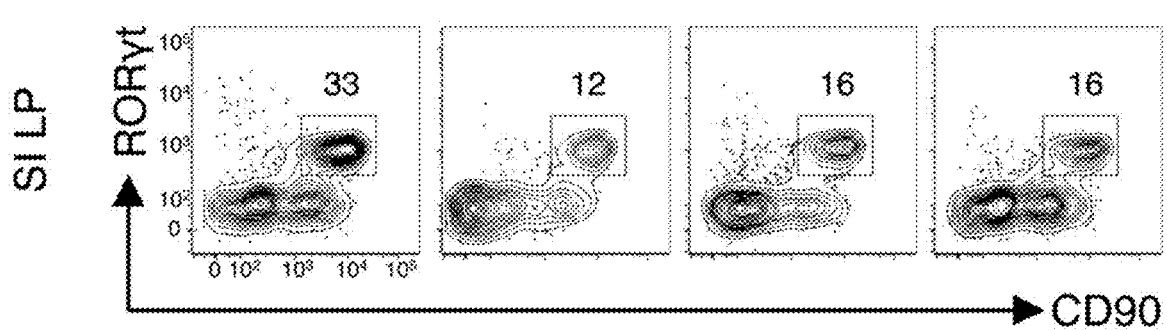
Figure 4D:
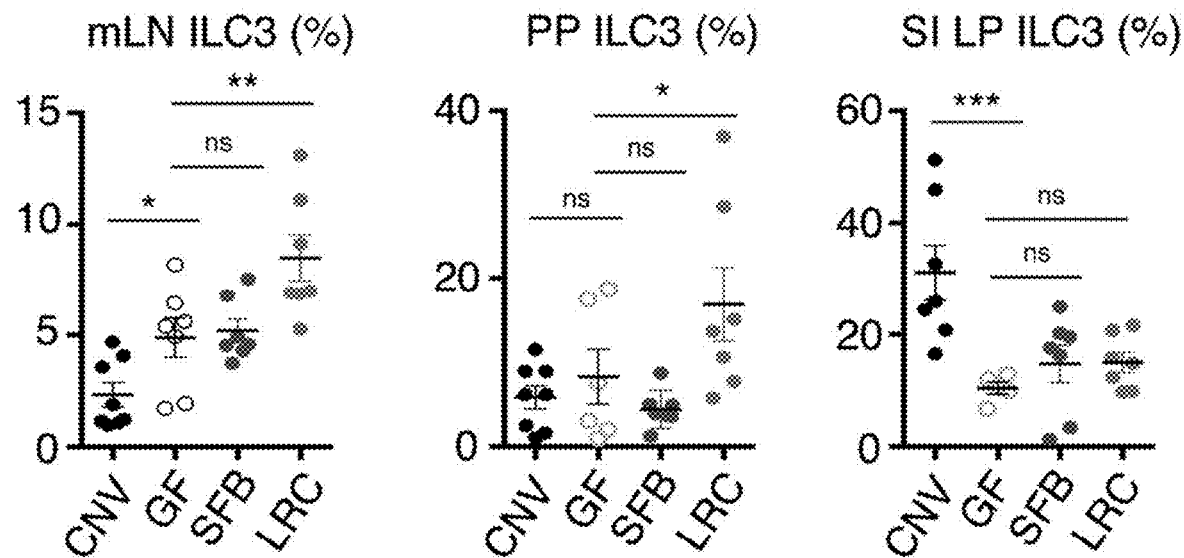
Figure 4E:
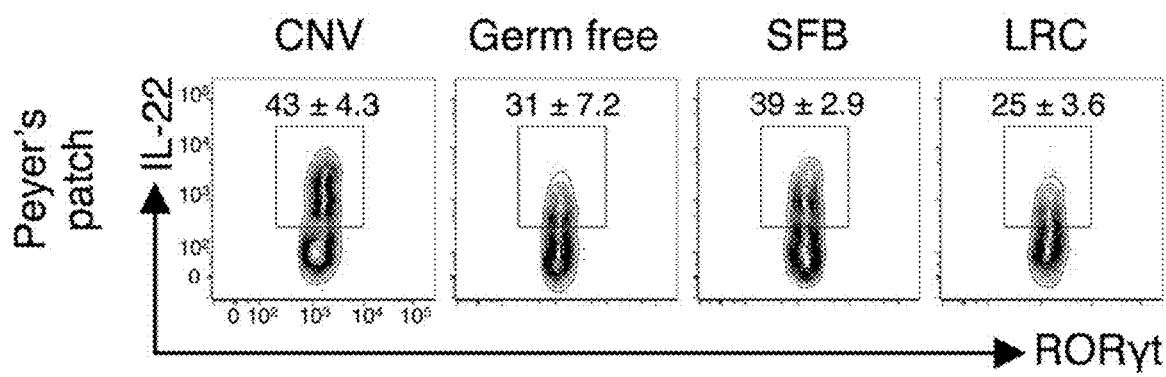
Figure 9E:
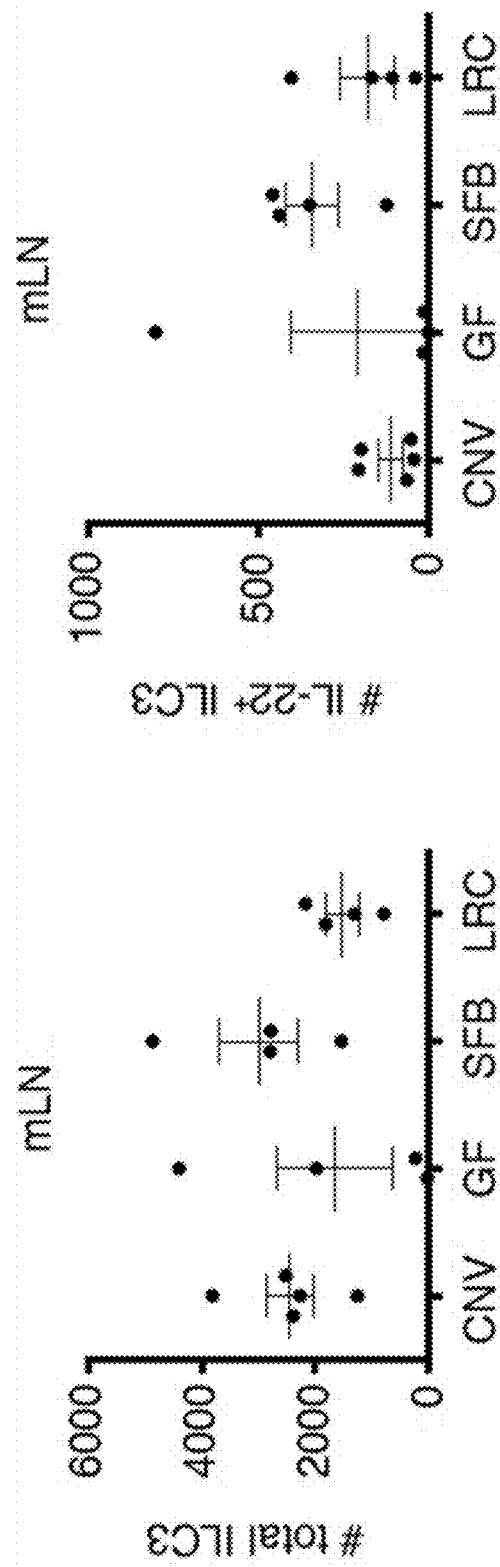

Lymphoid Tissue-Resident Commensal Bacteria Promote Tissue-Specific ILC3 Responses We tested if LRCs also promote ILC3 responses in intestinal-associated lymphoid tissues. We measured ILC3 frequencies in the PP, mLN and SI LP of CNV, GF, SFB-monocolonized and LRC-monocolonized mice. GF mice have reduced frequencies of ILC3 in the SI LP as compared to CNV mice. Monocolonization by SFB did not significantly alter ILC3 frequencies in the PP, mLN and SI LP as compared to GF mice (FIG. 4A-D). In contrast, LRC-monocolonized mice revealed a significant increase in ILC3 frequencies in the PP and mLN (FIGS. 4A, 4B and 4D) but not in the SI LP as compared to GF mice (FIGS. 4C and 4D). However, total numbers of ILC3s in the mLN did not change following LRC monocolonization (FIG. 9E). Notably, ILC3s in the PP of LRC-monocolonized mice produced IL-22 (FIG. 4E). Thus, LRCs modulate tissue-specific Th17 cell and ILC3 responses in healthy mammalian lymphoid tissues.

Figure 5A:
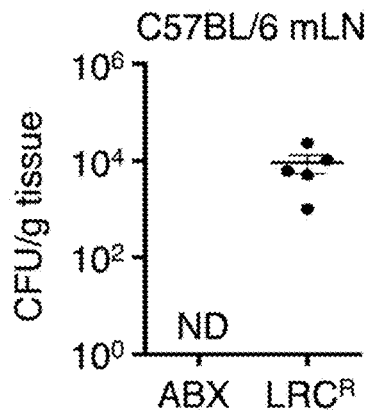
Figure 5B:
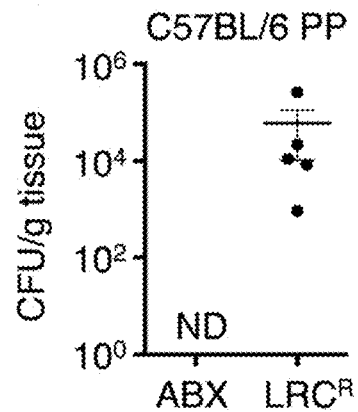
Figure 5C:
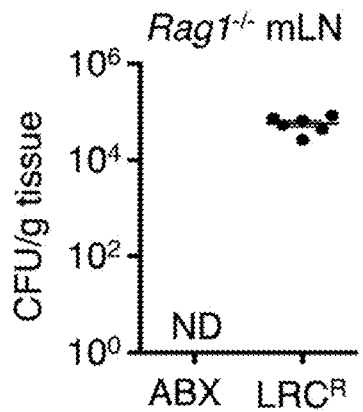
Figure 5D:
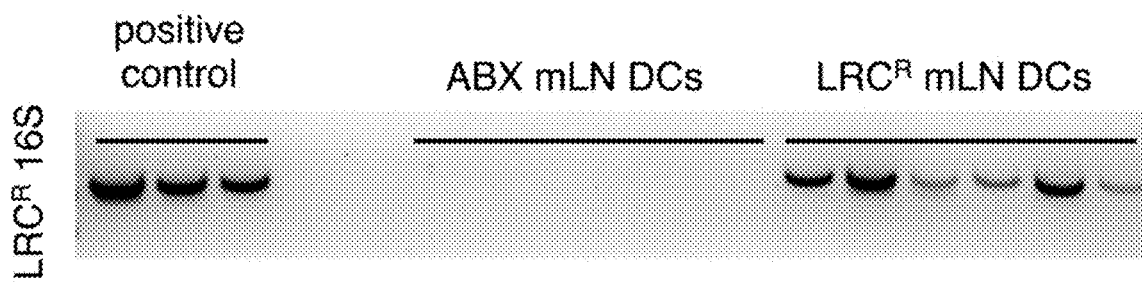
Figure 5E:
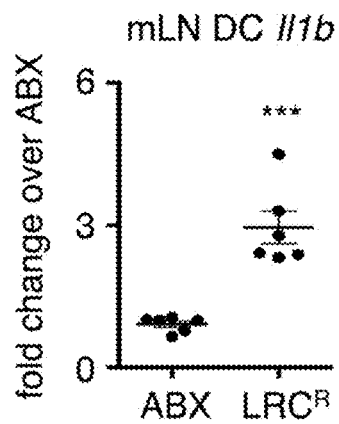
Figure 5E:
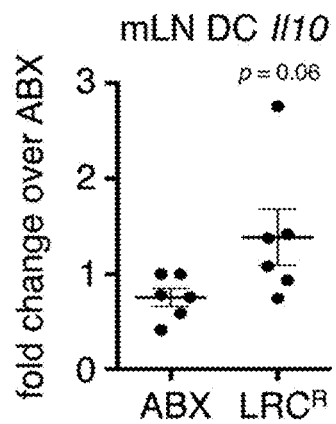
Figure 5E:
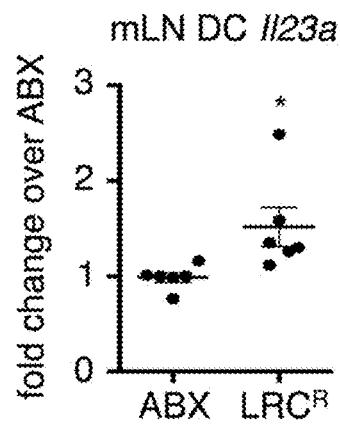
Figure 10A:
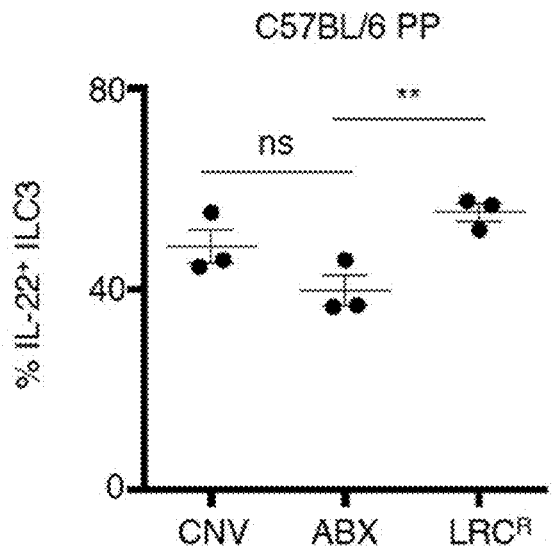
Figure 10B:
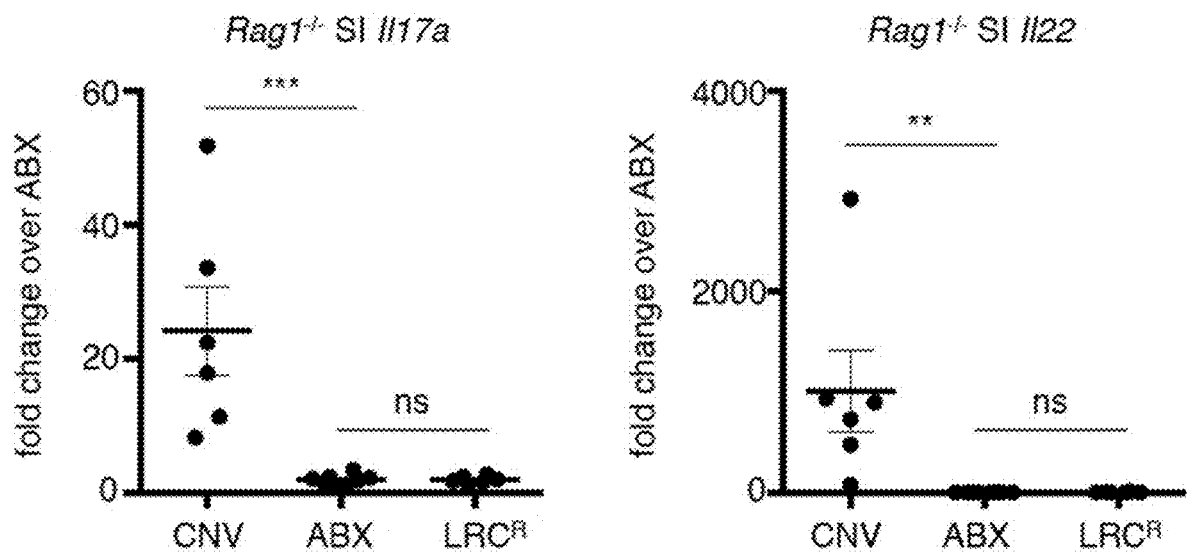

Lymphoid Tissue-Resident Commensal Bacteria Promote ILC3-Derived IL-22 Responses that Enhance Tissue Colonization To test if LRCs induce immune responses that limit its own colonization or the colonization of other bacteria, we established a mouse model of LRC colonization by treating conventional C57BL/6 mice with a limited cocktail of antibiotics (ABX) followed by inoculation with an antibiotic-resistant LRC, *Achromobacter* (LRC$^R$). We confirmed that, similar to our results using LRC-monocolonized mice, LRC$^R$ could be cultured from the mLN, PPs and intestinal lumen of LRC$^R$-colonized C57BL/6 mice (FIG. 5A-B). Furthermore, analyses of ILC3 responses in LRC$^R$-colonized C57BL/6 mice revealed a significant increase in IL-22$^+$ ILC3 frequencies as compared to ABX-treated controls (FIG. 10A). Live LRC$^R$ were also detected in the mLN of LRC$^R$-colonized Rag1$^{-/-}$ mice (FIG. 5C), allowing us to interrogate selective interactions between LRCs and the innate immune system. To investigate whether DC colonization and cytokine modulation by LRCs also occur in the absence an adaptive immune system in vivo, we measured LRC$^R$ 16S rDNA and cytokine gene expression in CD11c$^+$ cells isolated from the mLN of LRC$^R$-colonized Rag1$^{-/-}$ mice. LRC$^R$ 16S rDNA was detected in CD11c$^+$ cells from LRC$^R$-colonized but not in control ABX-treated mice (FIG. 5D). Furthermore, CD11c$^+$ cells from LRC$^R$-colonized mice expressed increased levels of Il1b, Il10 and Il23a as compared to CD11c$^+$ cells from control ABX-treated mice (FIG. 5E). Induction of Il1b and Il23a was associated with an increase in Il17a and Il22 expression in the whole mLN but not the small intestine of LRC$^R$-colonized Rag1$^{-/-}$ mice (FIGS. 5F and 10B).

To test if induction of IL-17A and IL-22 by LRCs would be important in limiting its own colonization in intestinal-associated lymphoid tissues. To test this, ABX-treated C57BL/6, Il17a$^{-/-}$ and Il22$^{-/-}$ mice were inoculated with LRC$^R$ and lymphoid tissue colonization was assessed 10 days later. We also tested if colonization of Il22$^{-/-}$ mice with LRC$^R$ would result in systemic dissemination of LRC$^R$. However, systemic dissemination of LRC$^R$ was not observed in the absence of either IL-17A or IL-22 (FIG. 10C). Furthermore, analysis of intestinal-associated lymphoid tissues revealed an impaired ability of LRC$^R$ to colonize the mLN and PPs of Il22$^{-/-}$ but not C57BL/6 or Il17a$^{-/-}$ mice (FIGS. 5G and 5H). These data suggest that IL-22 may also facilitate colonization of lymphoid tissues by commensal bacteria. To test whether innate cell-derived IL-22 could impact lymphoid tissue colonization by commensal bacteria, we inoculated ABX-treated Rag1$^{-/-}$ and Rag1$^{-/-}$Il22$^{-/-}$ mice with LRC$^R$ and measured lymphoid tissue colonization. Similar to our findings using lymphocyte-sufficient Il22$^{-/-}$ mice, inoculation of Rag1$^{-/-}$Il22$^{-/-}$ mice with LRC$^R$ did not result in systemic dissemination of LRC$^R$ (FIG. 10D), but resulted in impaired LRC$^R$ colonization in the mLN (FIG. 5I). Collectively, these results suggest that induction of ILC3-derived IL-22 is important to facilitate LRC colonization of lymphoid tissues.

Figure 10G:
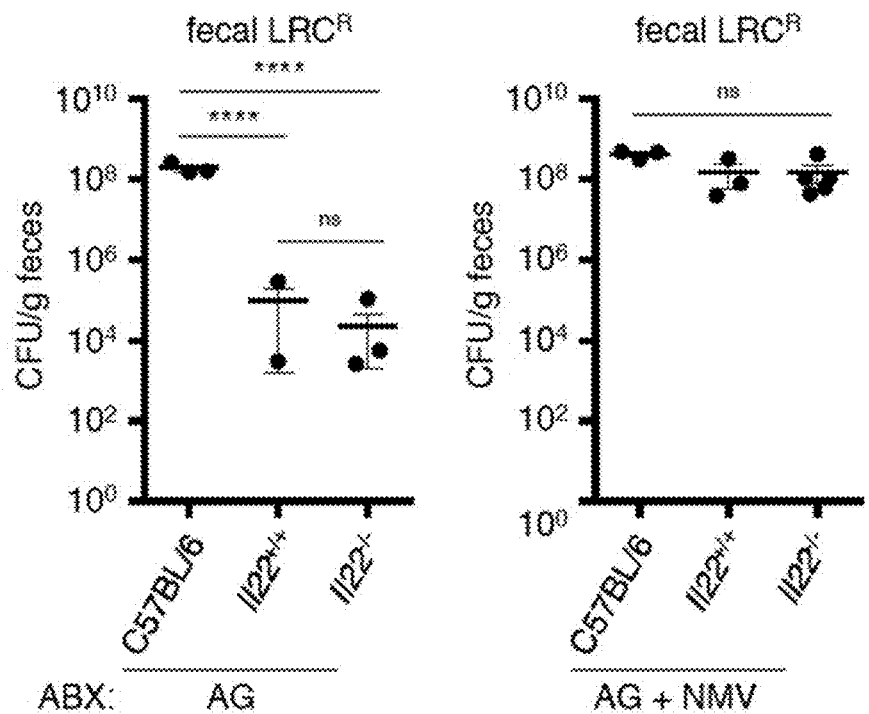
Figure 10H:
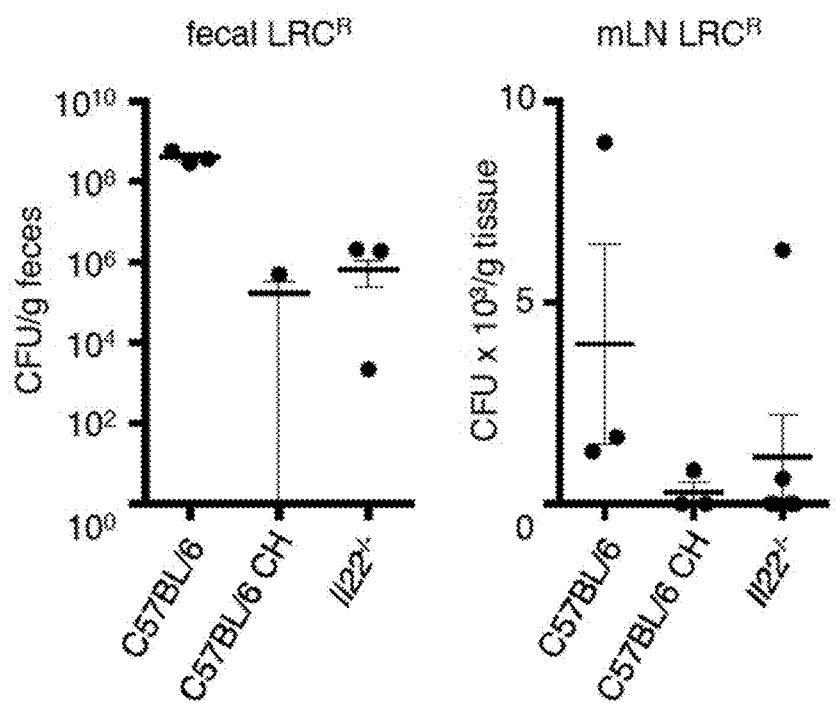

To test if in the absence of IL-22 there may be an expansion of commensal bacteria that outcompete and limit LRC entry and colonization, we examined luminal colonization in C57BL/6, Il22$^{-/-}$, Il17a$^{-/-}$, Rag1$^{-/-}$ and Rag1$^{-/-}$Il22$^{-/-}$ mice that were treated with a limited ABX cocktail followed by LRC$^R$ inoculation. At 10 days post-inoculation, we detected an absence of fecal LRC$^R$ in Il22$^{-/-}$ and Rag1$^{-/-}$Il22$^{-/-}$ but not in C57BL/6, Rag1$^{-/-}$ and Il17a$^{-/-}$ mice (FIG. 10E-F). Il22$^{+/+}$ littermates raised under the same conditions as Il22$^{-/-}$ mice also have impaired ABX-mediated fecal LRC colonization, and administration of additional antibiotics including neomycin, metronidazole and vancomycin, restored fecal LRC colonization in Il22$^{-/-}$ mice and Il22$^{+/+}$ littermates (FIG. 10G). Furthermore, cohousing Il22$^{-/-}$ mice with C57BL/6 mice impaired fecal and lymphoid tissue LRC colonization in C57BL/6 mice (FIG. 10H). Altogether, our data indicate that IL-22 promotes LRC colonization by limiting competition with other commensal microbes.

Figure 5K:
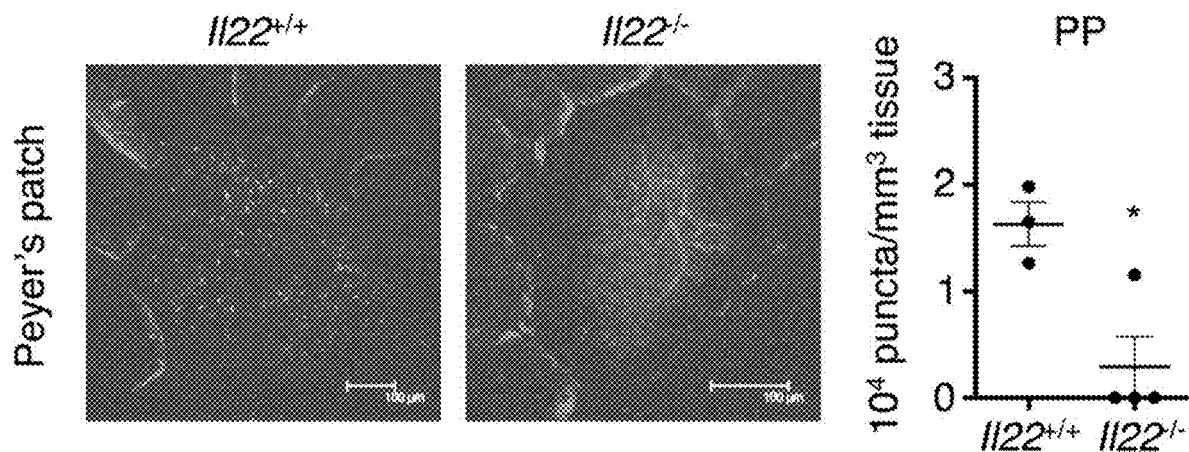
Figure 5L:
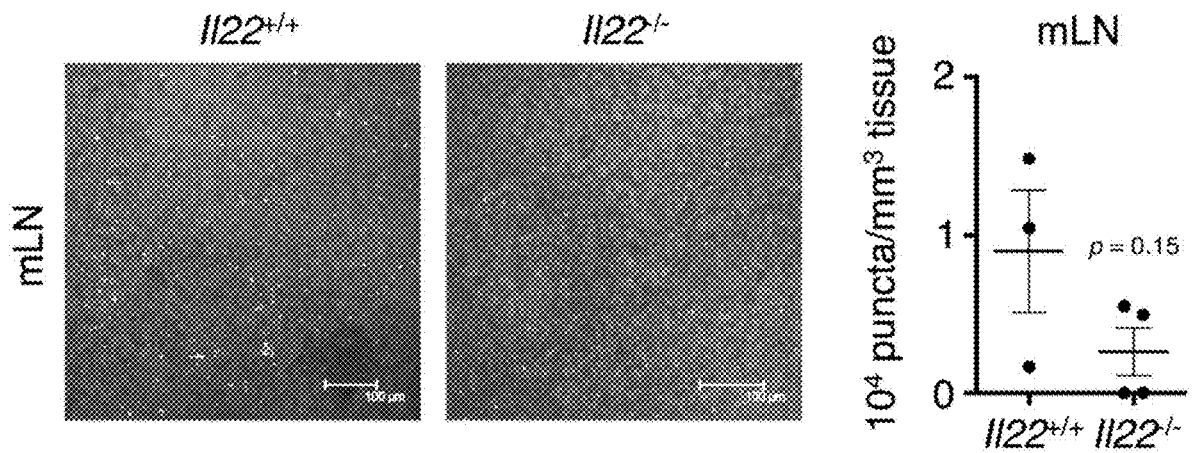

To further interrogate the role of IL-22 in regulating LRC colonization, we pursued a gain-of-function approach. Consistent with a role for IL-22 in promoting lymphoid tissue colonization by LRCs, exogenous administration of recombinant mouse IL-22 to LRC$^R$-colonized Rag1$^{-/-}$ mice significantly enhanced LRC$^R$ levels in the mLN (FIG. 5J). The LRC$^R$ colonization model requires the use of antibiotics that can eliminate other commensal bacteria. To test the requirement for IL-22 in LRC colonization in the presence of a complex microbiota, we measured levels of the endogenous LRC, *Alcaligenes* by FISH in conventional Il22$^{-/-}$ mice and littermate controls. Compared to Il22$^{+/+}$ littermates, conventional Il22$^{-/-}$ mice have reduced *Alcaligenes* puncta in the PP and mLN (FIGS. 5K and 5L). These data demonstrate that IL-22 plays a critical role in enhancing the colonization of intestinal-associated lymphoid tissues by LRCs in the presence of a complex microbiota.

Figures 6A, 6B:
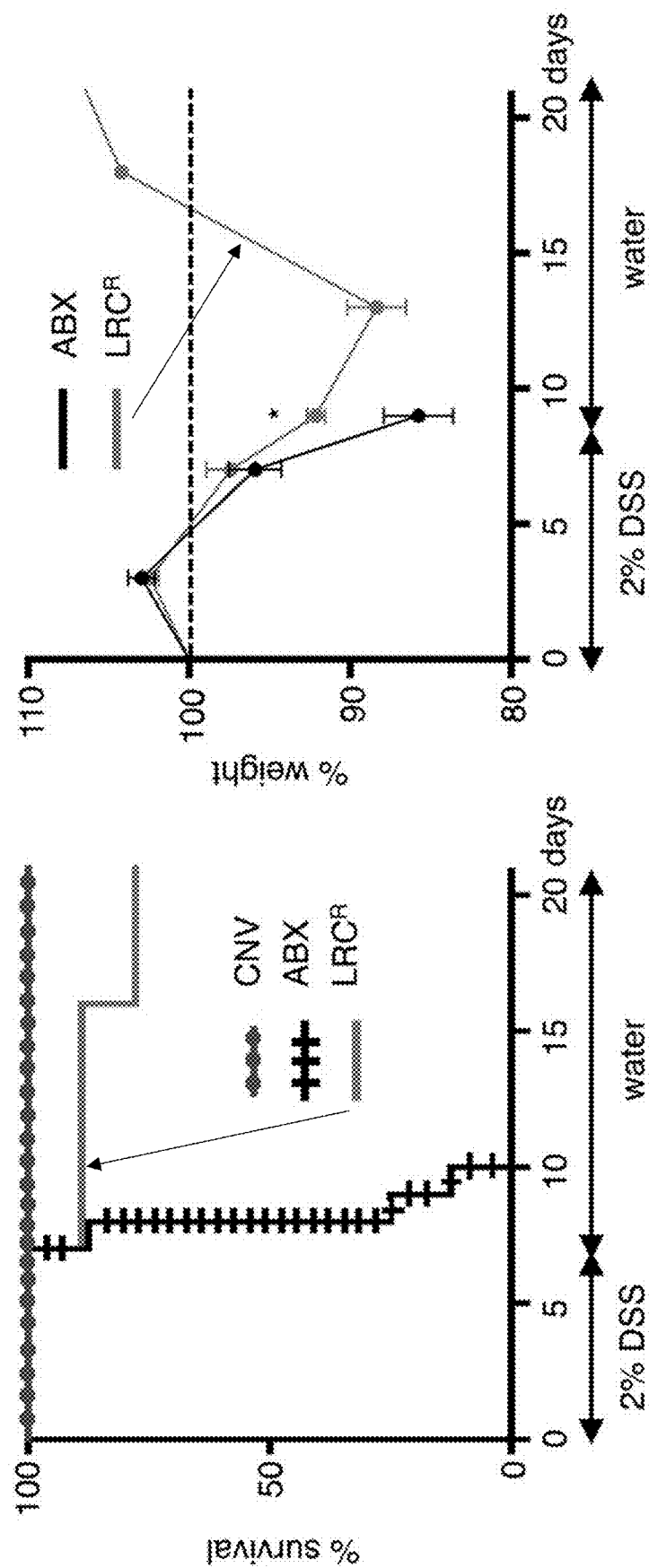
FIGS. 6A-6E. Lymphoid tissue-resident commensal bacteria promote IL-10R-dependent protection from DSS-induced intestinal tissue damage and mortality. CNV, ABX-treated and ABX-resistant *Achromobacter* (LRC$^R$)-colonized-colonized Rag1$^{-/-}$ mice were administered 2% DSS in their drinking water for 6 to 7 days and then placed on regular drinking water. Mice were monitored for survival (A) and weight loss (B) for up to 21 days. Data in panel A are pooled from 2 independent experiments for a total of 8-9 mice per group. (C) Mice were sacrificed on day 6 and analyzed for colon tissue pathology and inflammatory infiltrate by H&E. Data in panel C are representative of 2 independent experiments. Scale bar—100 μm. (D and E) ABX control, IgG- or anti-IL-10R-treated LRC$^R$-colonized Rag1$^{-/-}$ mice were administered 2% DSS for 8 days. Percentage of starting weight on day 7 (D) and serum IFN$\gamma$ on day 8 are quantified (E). One-way ANOVA, D and E—**p<0.01. Data in panel D are pooled from 3 independent experiments for a total of 12-13 mice per group. Data in panel E are pooled from 3 independent experiments for a total of 8-12 mice per group. Data are represented as mean±SEM. Statistics shown in B were performed using unpaired, two-tailed, student's t test. Statistics shown in panels D and E were performed using one-way ANOVA with uncorrected Fisher's LSD test. *, p<0.05; , p<0.01; *, p<0.001. See also FIGS. 11 and 12.
Figure 6C:
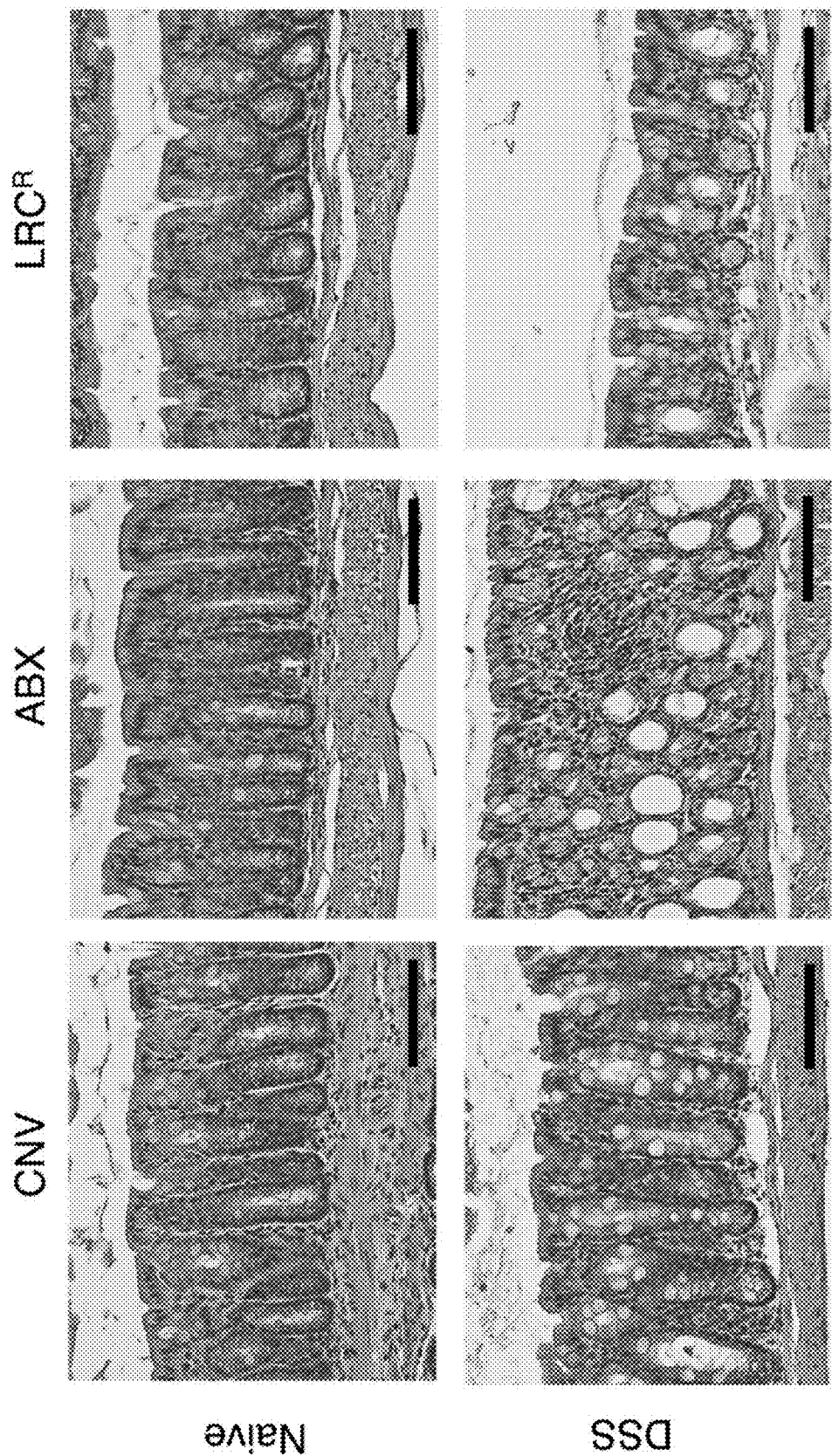
Figure 11A:
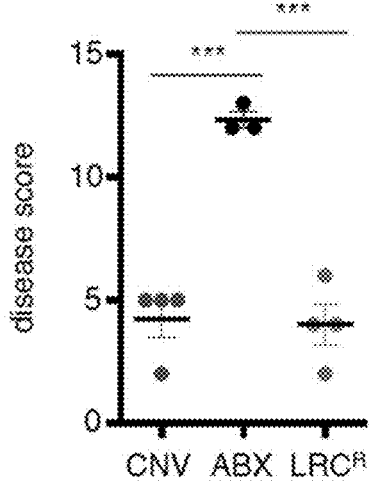
FIGS. 11A-11D. Colonization of antibiotic-treated or germ-free mice with lymphoid tissue-resident commensal bacteria provides protection from DSS-induced intestinal tissue damage and mortality (Related to FIGS. 6A-6E). (A) Disease score for CNV, ABX and LRC$^R$-colonized Rag1$^{-/-}$ mice treated with 2% DSS in drinking water for 6 days. (B) Red blood cell (RBC) counts for ABX and LRC$^R$-colonized Rag1$^{-/-}$ mice treated with 2% DSS in drinking water for 8 days. Data pooled from 2 independent experiments for a total of 4-7 mice per group. (C) CNV, GF and Bordetella-monocolonized C57BL/6 mice were administered 2% DSS in the drinking water for 5 days and then placed on regular drinking water. CNV, n=3; GF, n=7; Bordetella-monocolonized, n=9. (D) GF and Bordetella-monocolonized Rag1$^{-/-}$ mice were administered 2% DSS in the drinking water for 7-9 days and then placed on regular drinking water for the duration of the experiment. GF, n=6; Bordetella-monocolonized, n=6. Data in panels C and D are pooled from 2 independent experiments. Statistics shown in panels A and B were performed using unpaired, two-tailed, student's t test with no correction for multiple comparisons. Data are represented as mean±SEM. ***, $p<0.0001$.
Figure 11B:
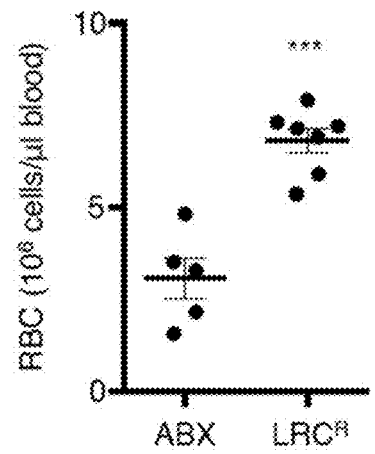
Figure 11C:
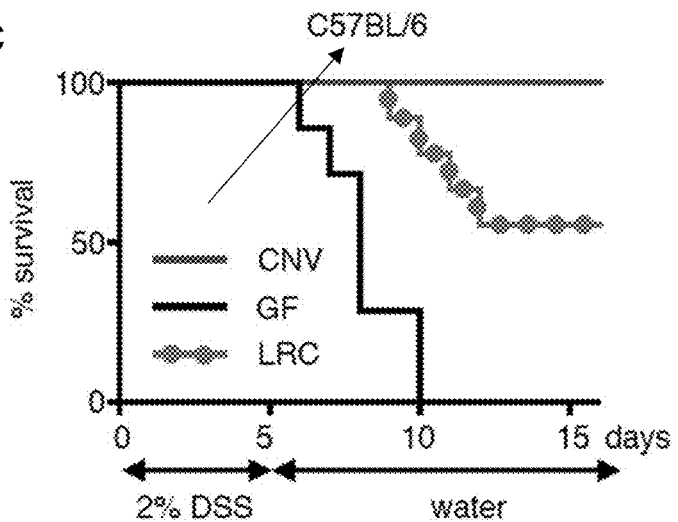
Figure 11D:
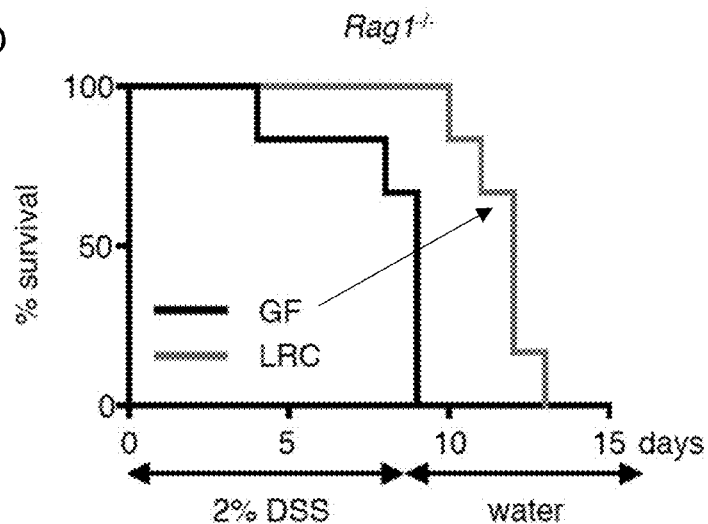

Lymphoid Tissue-Resident Commensal Bacteria Colonization Provides Protection from Chemical-Induced Inflammation and Intestinal Injury in an IL-10-Dependent Manner To test whether there was a benefit to mammalian hosts following LRC colonization, we employed a model of intestinal damage where administration of the chemical, dextran sodium sulfate (DSS), induces significant damage to the colonic epithelium. Compared to CNV mice, mice lacking commensal bacteria or treated orally with a broad-spectrum cocktail of antibiotics are highly sensitive to intestinal damage induced by DSS and succumb to disease (Ayers et al., 2012, Nature medicine 18, 799-80; Kitajima et al., 2001, Experimental animals/Japanese Association for Laboratory Animal Science 50, 387-395; Maslowski et al., 2009, Nature 461, 1282-1286). To test the functional significance of LRC colonization following DSS treatment, we administered 2% DSS to CNV, ABX-treated alone and LRC$^R$-colonized Rag1$^{-/-}$ mice for 6-7 days, then removed DSS, and re-administered normal drinking water. Compared to CNV mice, which survived throughout the duration of the experiment (21 days), ABX-treated mice exhibited significant systemic and intestinal morbidity and succumbed to disease by day 10 post DSS administration (FIG. 6A, FIG. 11A). In contrast, LRC$^R$-colonized mice were largely protected from DSS-induced mortality, and demonstrated significantly reduced weight loss and elevated red blood cell counts as compared to ABX-treated controls (FIG. 6A-B, 11A-B). Further, analyses on day 5 post DSS administration revealed that although CNV mice did not exhibit significant intestinal damage or inflammation in the colon at this low dose of DSS, the colons of ABX-treated mice displayed severe loss of crypt architecture and extensive inflammation (FIG. 6C). In contrast, LRC$^R$-colonized mice had visible but reduced intestinal tissue damage and inflammation (FIG. 6C). LRC-conferred protection from DSS-induced mortality was also observed in gnotobiotic C57BL/6 (FIG. 11C) and Rag1$^{-/-}$ (FIG. 11D) mice monocolonized with *Bordetella* spp., suggesting that host protection can occur in the absence of other commensal bacteria. Collectively, our data demonstrate that colonization of lymphoid tissues by selective commensal bacteria is host beneficial in the context of intestinal damage and inflammation.

Figure 6D:
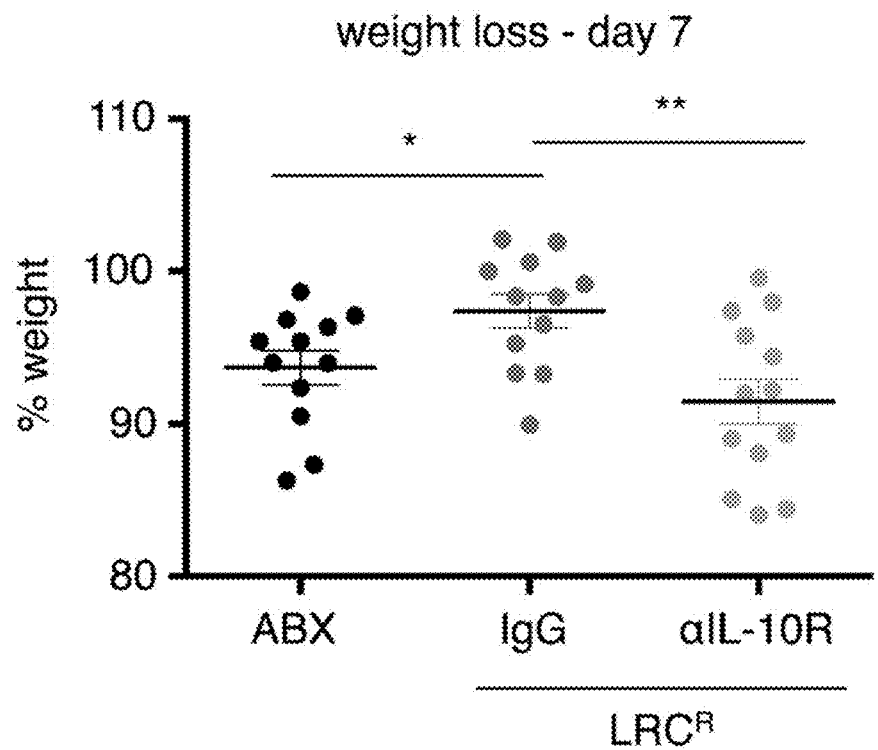
Figure 6E:
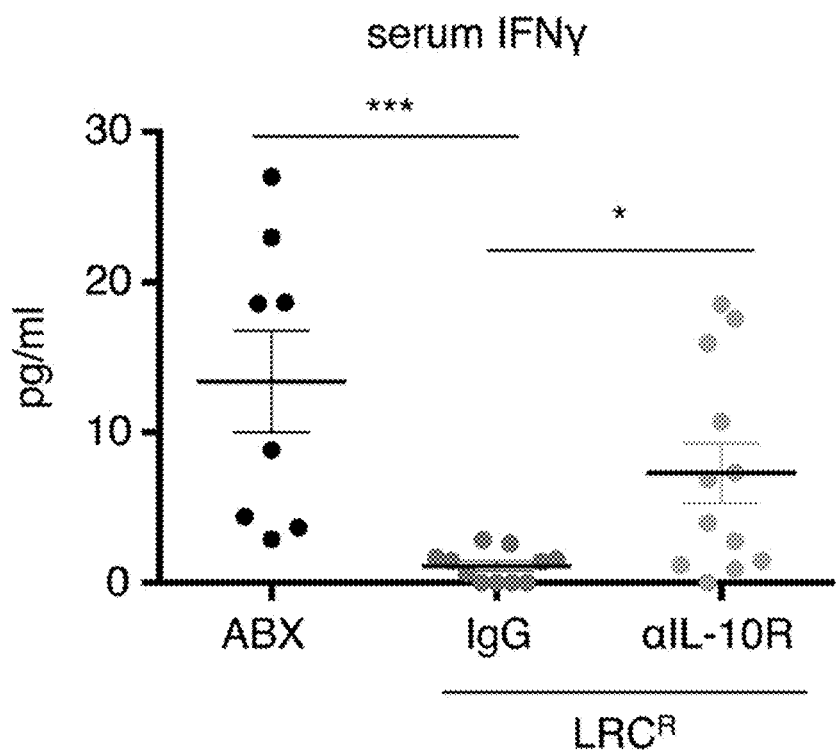
Figure 12A:
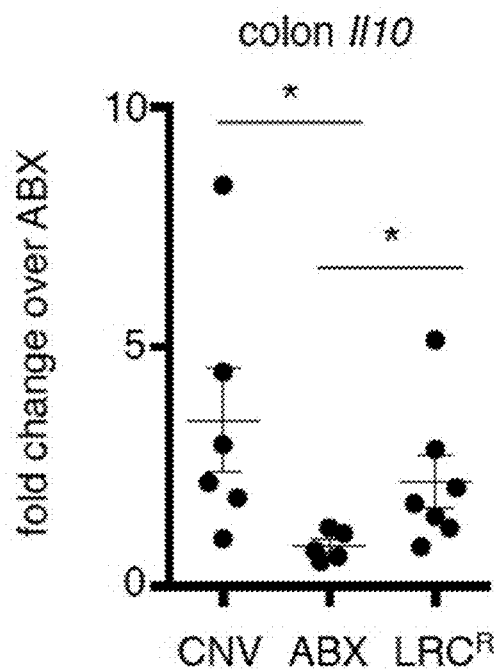
FIGS. 12A-12F. Lymphoid tissue-resident commensal bacteria provide protection from DSS-induced intestinal tissue damage in an IL 10R-dependent and IL-22-independent manner (Related to FIGS. 6A-6E). (A) Expression of Il10 in the colon of 2% DSS-treated CNV, ABX-treated or LRC$^R$-colonized Rag1$^{-/-}$ mice day 6 post-DSS treatment. Data pooled from 2 independent experiments with a total of 5-7 mice per group. (B and C) ABX and LRC$^R$-colonized Rag1$^{-/-}$ mice given rat IgG, anti-IL-22 or anti-IL-10R were treated with 2% DSS in the drinking water for 8 days and monitored for weight loss. Data in B representative of 2 independent experiments. Data in C represent pooled data from 3 independent experiments. (D) ABX, LRC$^R$-colonized Rag1$^{-/-}$ mice given rat IgG or anti-IL-10R were treated with 2% DSS in the drinking water for 8 days and colon pathology was assessed on day 8. Scale bar—100 μm. Data representative of 2 independent experiments. (E) Weight loss and (F) colon pathology of ABX-treated, rat IgG or anti-IL-10R-injected Rag1$^{-/-}$ mice given 2% DSS for 9 days. Scale bar—100 μm. Data in E and F are representative of 2 independent experiments. Statistics in panel A were performed using Mann-Whitney test with no correction for multiple comparisons. Statistics in panel B were performed on day 7 using one-way ANOVA and uncorrected Fisher's LSD test. *, $p<0.05$; **, $p<0.01$.
Figure 12B:
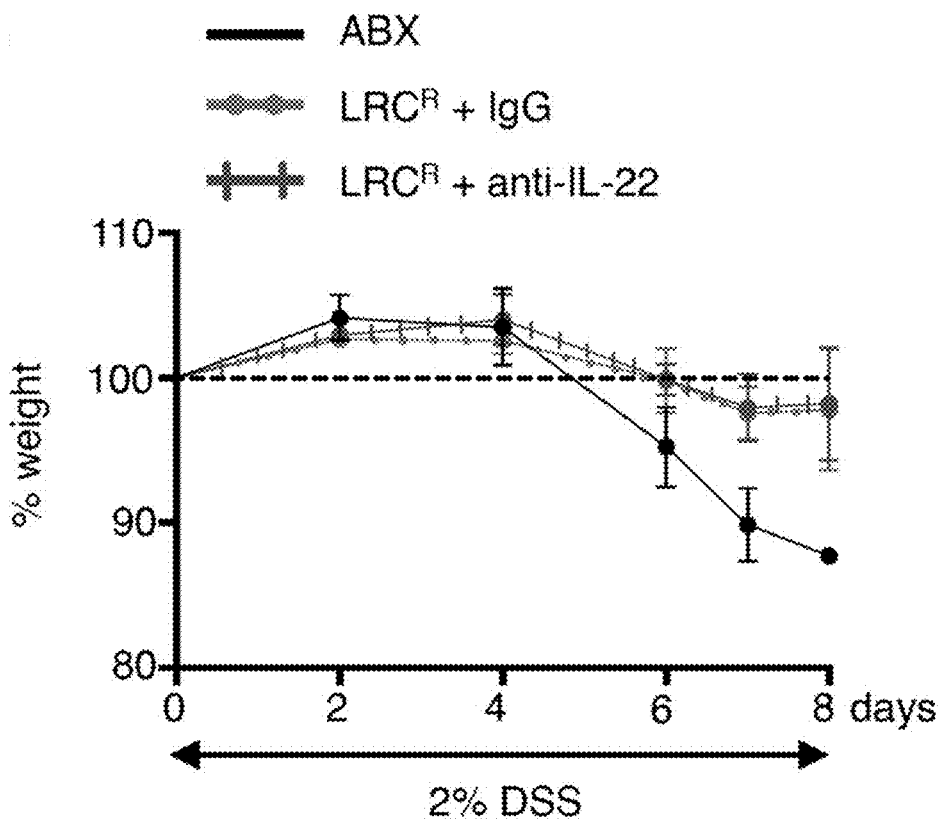
Figure 12C:
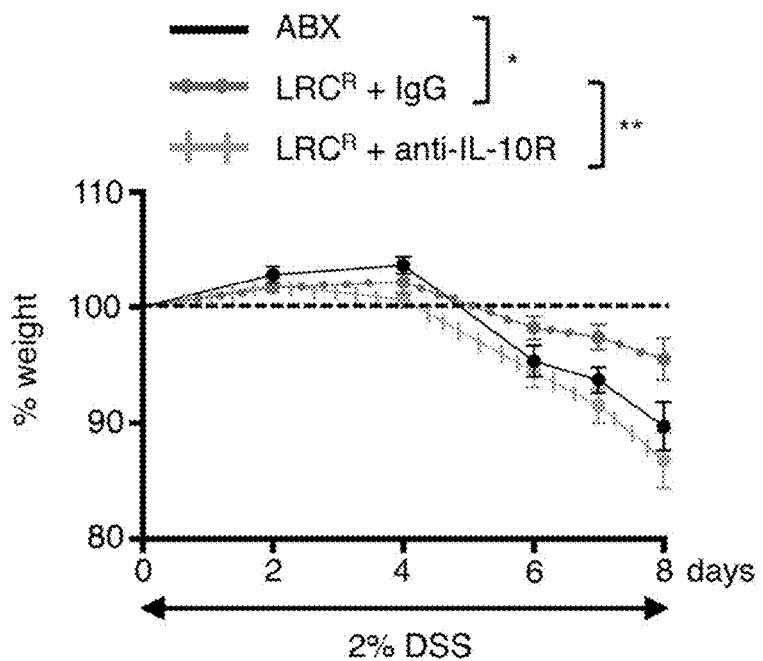
Figure 12D:
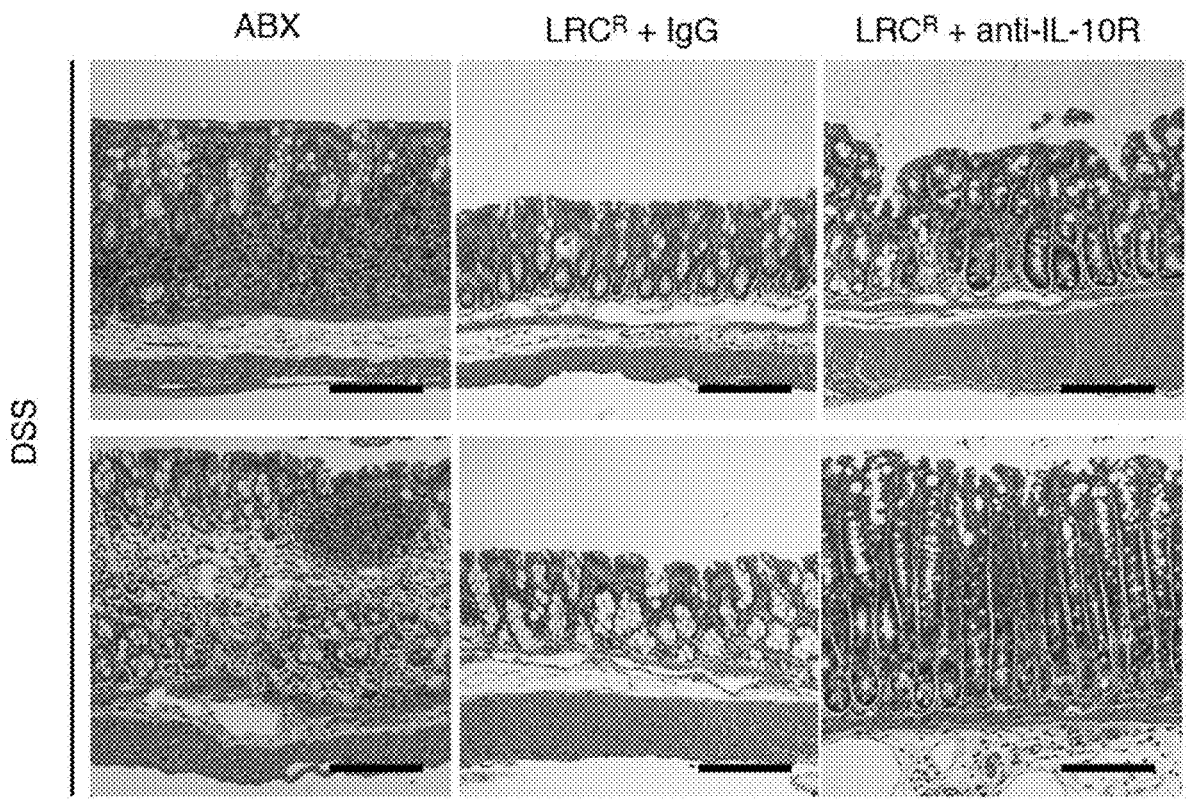
Figure 12E:
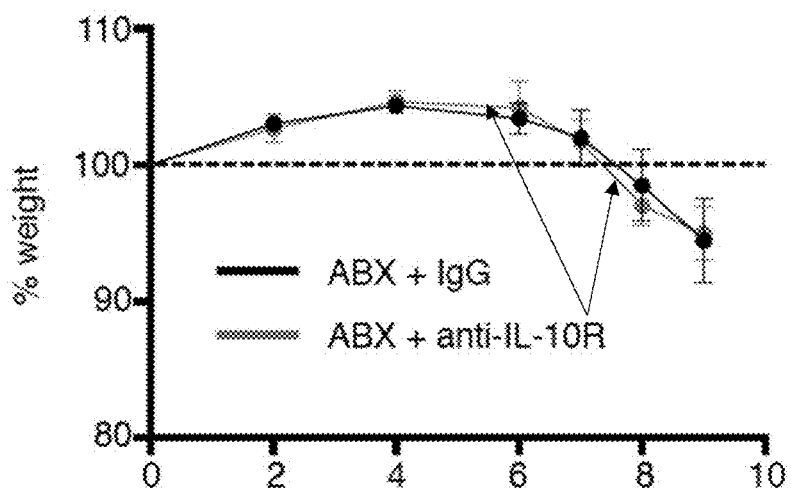
Figure 12F:
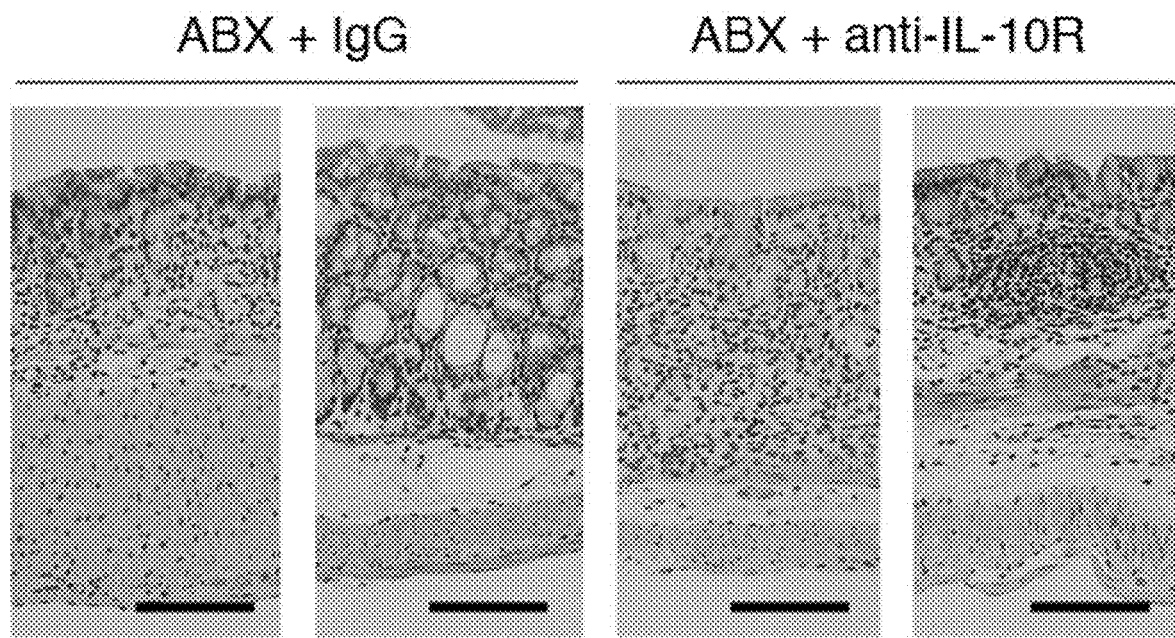

To investigate whether LRC-induced IL-22 is providing host protection in LRC$^R$-colonized mice, we administered anti-IL-22 neutralizing antibody to LRC$^R$-colonized Rag1$^{-/-}$ mice during exposure to DSS. Anti-IL-22-treated mice exhibited comparable weight loss to IgG-treated mice (FIG. 12B), suggesting that IL-22 is not involved in LRC-mediated host protection from DSS. As the anti-inflammatory cytokine IL-10 was also induced upon LRC colonization both in the steady state and during DSS exposure (FIGS. 2A-2C FIG. 2 and FIG. 12A), we interrogated whether innate cell-derived IL-10 is providing host protection in LRC$^R$-colonized mice. To test this, we administered anti-IL-10R neutralizing antibody to LRC$^R$-colonized Rag1$^{-/-}$ mice during exposure to DSS. Blockade of IL-10-IL-10R interactions resulted in increased weight loss and colonic inflammation as compared to IgG-treated controls (FIG. 6D, 12C-D). ABX-treated Rag1$^{-/-}$ mice on DSS display elevated levels of serum IFNγ, which was significantly diminished in LRC$^R$-colonized Rag1$^{-/-}$ mice (FIG. 6E). Conversely, IL-10R neutralization in LRC$^R$-colonized mice partially restored serum IFNγ levels observed in ABX-treated mice (FIG. 6E). Treatment of ABX-control Rag1$^{-/-}$ animals with anti-IL-10R during DSS exposure did not result in further weight loss or colon pathology compared to isotype-treated animals (FIG. 12E-F). Collectively, these data suggest that LRC colonization protects mice from intestinal and systemic inflammatory responses through induction of innate cell-derived IL-10.

Example 2

This example demonstrates that administration of LRC bacteria improves colonization and diversity when used in conjunction with FMT. On day 0, mice were administered broad-spectrum antibiotics ampicillin and neomycin for three days to deplete the endogenous microbiota. Mice were then gavaged with PBS, LRC strain CF220, or *E. coli*. On day 17 mice were removed from antibiotics. On days 18 and 21, all mice received a fecal microbiota transplant (FMT) from C57BL/6 mice. On day 31, mice were administered DSS.

Figure 13:
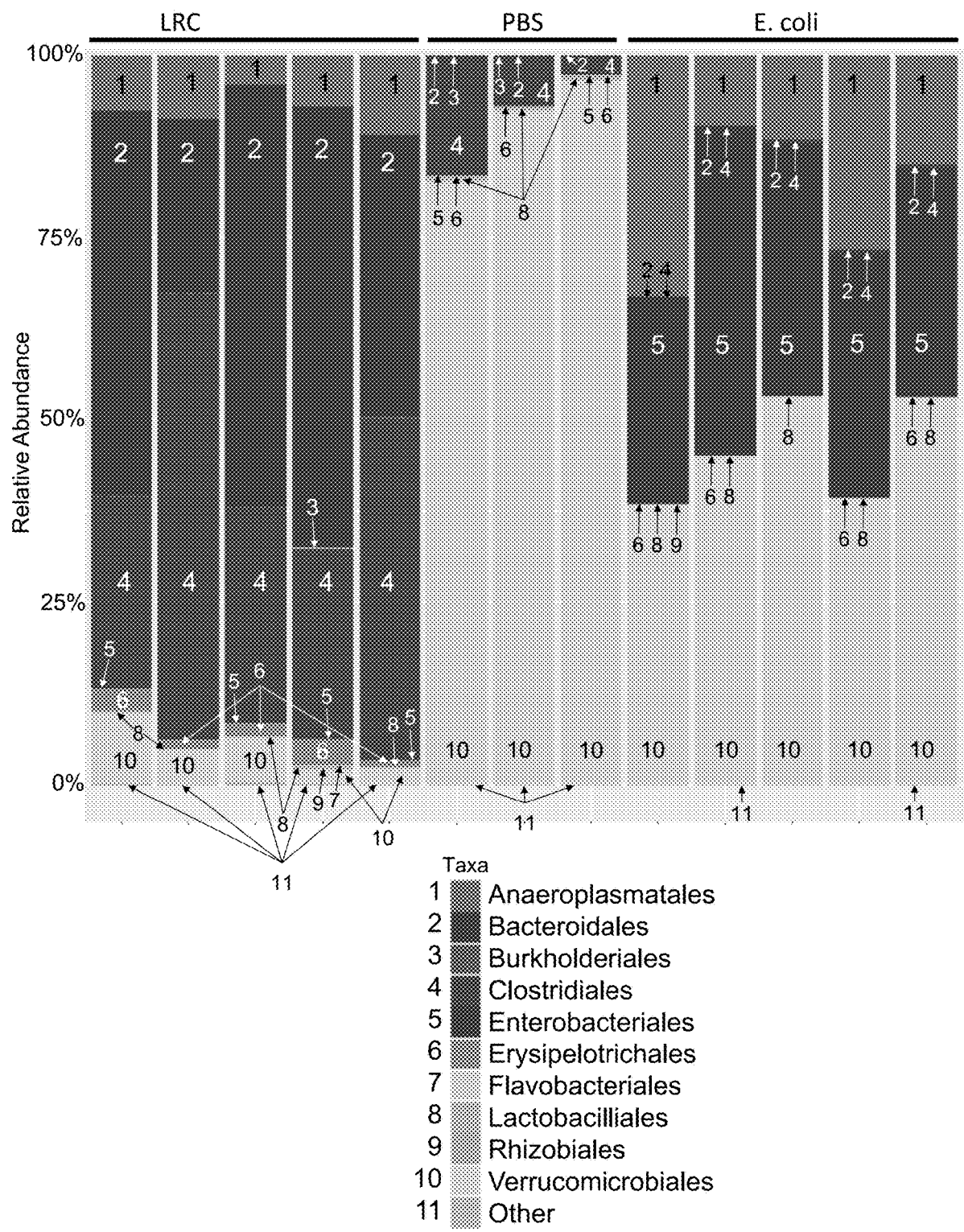
FIG. 13. 16S sequencing on mice that were administered: antibiotics, monocolonized with indicated bacteria and re-colonized by fecal transfer material (FMT). The monocolonization was done with LRC (CF220 strain of Ochrobacter), E. coli or control (PBS). The numbers on the bars correspond as follows: 1 Anaeroplasmatales; 2 Bacteriodales; 3 Burkholderiales; 4 Clostridiales; 5 Enterobacteriales; 6 Erysipelotrichales; 7 Flavobacteriales; 8 Lactobacillales; 9 Rhizobiales; 10 Verrucomicrobiales; 11 Other.
Figure 14:
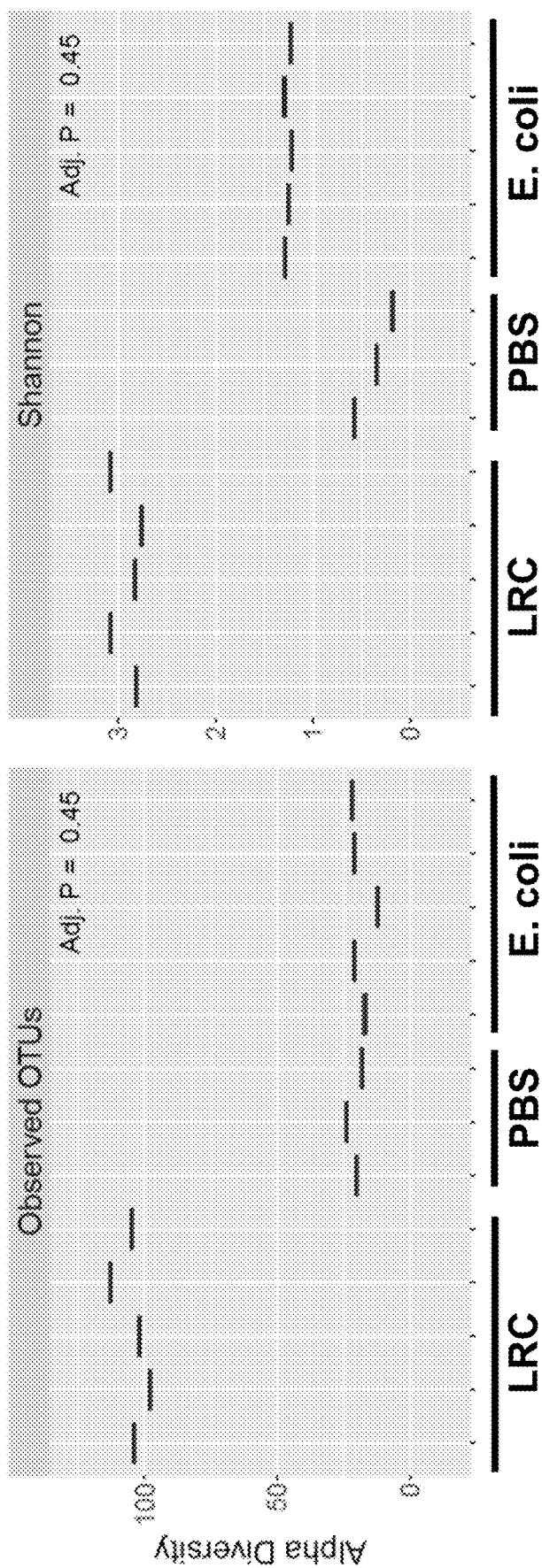
FIG. 14. Analysis of the 16S data for alpha-diversity in mice receiving: antibiotics, monocolonized with indicated bacteria (ORC strain, PBS or E. coli) and re-colonized by fecal transfer material (FMT). Alpha diversity is an indication of diversity of the microbiota, with higher numbers indicating more diversity.
Figure 15:
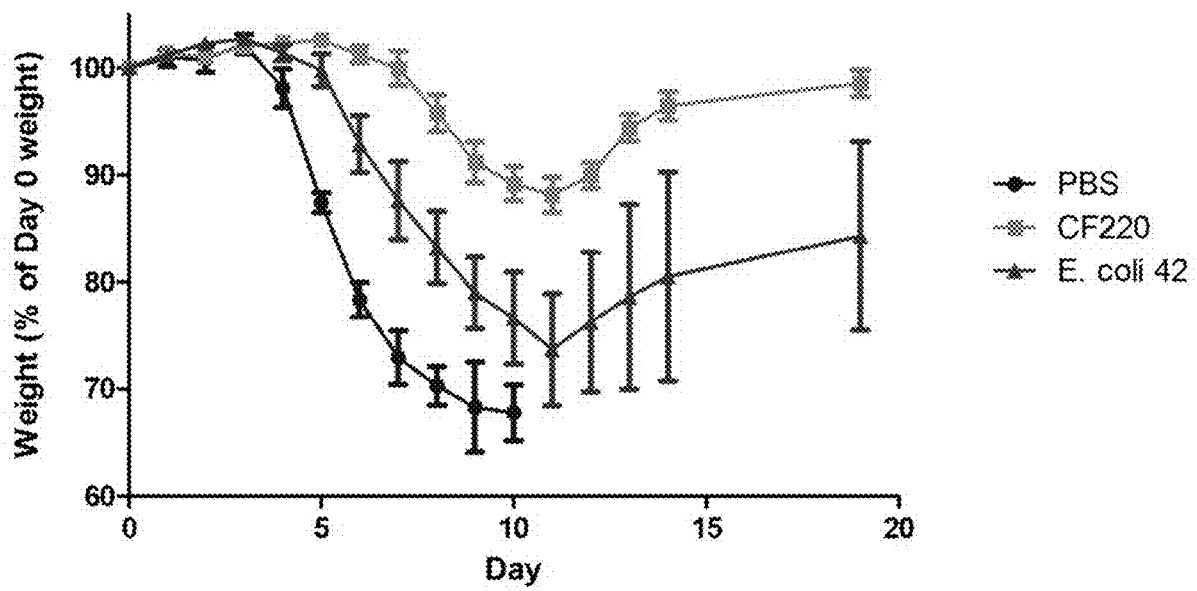
FIG. 15. Weight loss and overall survival in DSS administered mice that received a LCR strain prior to FMT. Male B6 mice received the following treatment: antibiotics and monocolonization with the indicated bacteria (or PBS control) (at about 6 weeks of age), recolonization at about 8 weeks of age (gavaged feces in PBS twice, at 1 and 4 days post antibiotic removal), inflammation was induced by dextran sodium sulfate (DSS) at about 10 weeks of age. Weight loss was followed in the different groups. DSS was removed after 9 days.
Figure 15:
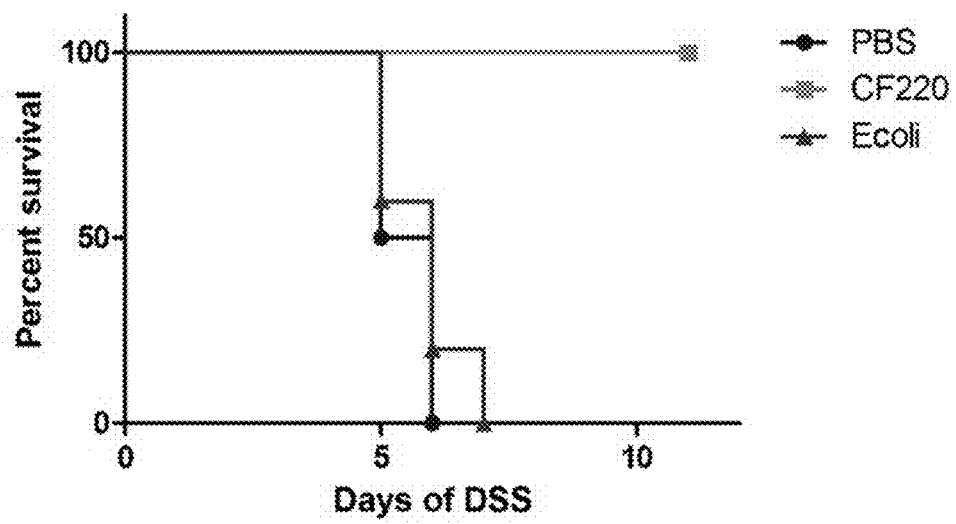

16S sequencing on mice from each experimental condition after FMT and those that were administered an LRC strain exhibit substantially more bacterial diversity as compared to those mice that were administered *E. coli* or PBS (FIG. 13). Analysis of the 16S data also shows substantially higher alpha-diversity in those mice receiving a LRC strain prior to FMT (FIG. 14). Weight loss and overall survival was substantially improved in DSS administered mice that received a LCR strain prior to FMT (FIG. 15).

Example 3

Figure 16:
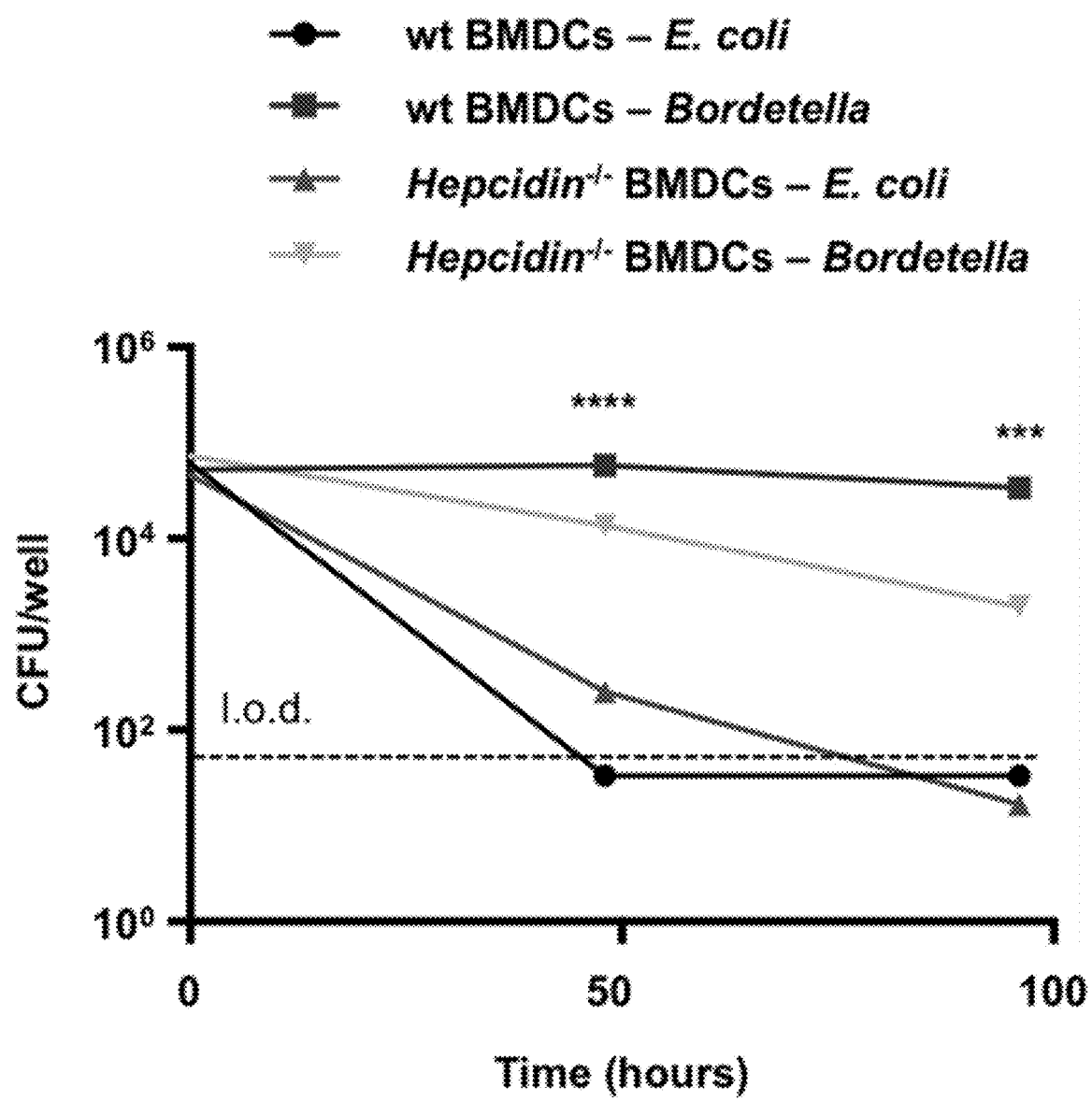
FIG. 16. Bone marrow dendritic cells (BMDCs) were generated from wild-type mice (WT) or hepcidin-deficient mice (Hepcidin−/−) and then were exposed to $E.\ coli$ or a model LRC ($Bordetella$). Colonization of the dendritic cells is indicated for each group.
Figure 17:
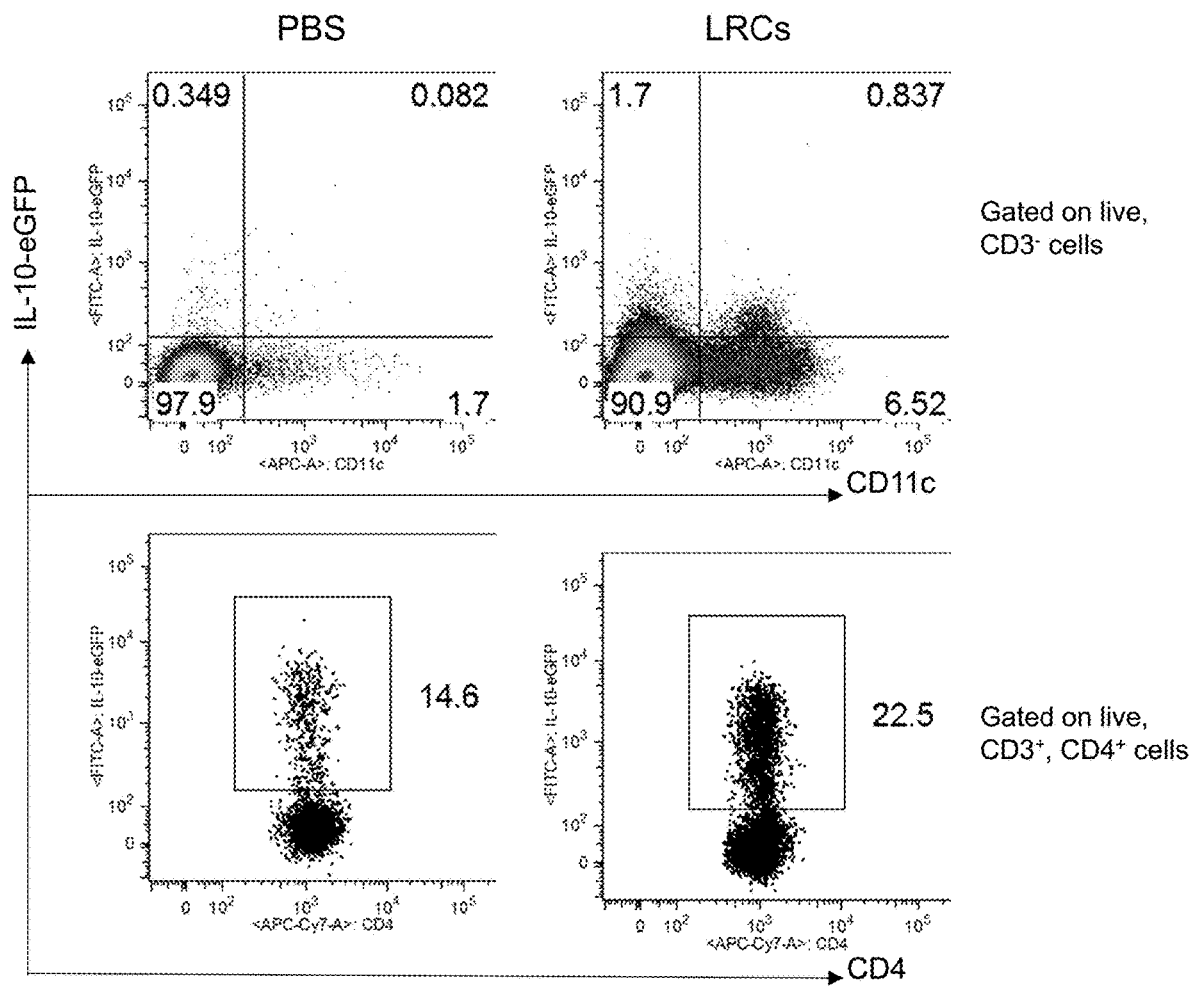
FIG. 17. Representation of analysis of small intestinal lamina propria for IL-10 reporter mice administered control (PBS) or LRC bacteria ($10^8$) by oral gavage. Mice were sacrificed on day 3 and IL-10 production was determined.

This example demonstrates the importance of hepcidin in LRCs colonization of dendritic cells. Bone marrow dendritic cells (BMDCs) were generated from wild-type mice (WT) or hepcidin-deficient mice (Hepcidin−/−) and then were exposed to *E. coli* or a model LRC (*Bordetella*). Colony forming units per well were measured and are shown in FIG. 16 for the indicated groups. These results demonstrate that hepcidin is important for colonization of dendritic cells selectively with LRCs.

While the present invention has been described through various specific embodiments, routine modification to these embodiments will be apparent to those skilled in the art, which modifications are intended to be included within the scope of this disclosure.

What is claimed is:

1. A probiotic composition comprising a therapeutically effective amount of two or more isolated lymphoid tissue-resident commensal bacteria selected from the group consisting of *Alcaligenes faecalis, Achromobacter xylosoxidans, Ochrobactrum* anthropi, *Ochrobactrum intermedium, Bordetella holmesii,* and *Bordetella hinzii,* wherein the composition does not contain bacteria belonging to gamma-proteobacteria, bacteriodetes phylum, and firmicutes phylum.

2. The probiotic composition of claim 1, wherein the probiotic composition comprises 100 million to one billion per dose of the two or more isolated lymphoid-tissue resident commensal bacteria.

3. The probiotic composition of claim 1, wherein the composition comprises a therapeutically effective amount of three of the isolated lymphoid-tissue resident commensal bacteria.

4. The probiotic composition of claim 1, wherein the composition comprises a therapeutically effective amount of four of the isolated lymphoid-tissue resident commensal bacteria.

5. The probiotic composition of claim 1, wherein the composition is a solid composition present in a powdered, granular or freeze-dried form.

6. The probiotic composition of claim 1 further comprising one or more of IL-10, IL-22 and hepcidin.

7. The probiotic composition of claim 4, wherein the one or more of the IL-10, IL-22 and hepcidin are formulated with the probiotic composition.

8. The probiotic composition of claim 1, wherein the composition comprises all of the isolated lymphoid tissue-resident commensal bacteria.

9. The probiotic composition of claim 1, wherein the isolated lymphoid-tissue resident commensal bacteria are the only bacteria present in the probiotic composition.

10. A method of increasing diversity of bacterial microbiota of intestinal tract of a mammalian subject comprising oral administration of the probiotic composition of claim 1 to said subject.

11. The method of claim 10, wherein the mammalian subject is a human individual.

12. The method of claim 11, wherein the human individual has inflammatory bowel disease, irritable bowel syndrome, an autoimmune condition, is undergoing chemotherapy, or is undergoing antibiotic treatment.

13. The method of claim 12, wherein the lymphoid tissue-resident commensal bacteria colonize intestinal-associated lymphoid tissues of the mammalian subject.

14. The method of claim 10, wherein the method further comprises administering to the subject one or more of IL-10, IL-22 and hepcidin.

15. The method of claim 14, wherein the one or more of the IL-10, IL-22 and hepcidin are formulated with the probiotic composition.

16. The method of claim 14, wherein the one or more of the IL-10, IL-22 and hepcidin are administered separately from the probiotic composition.

17. The method of claim 10, further comprising administering to the mammalian subject a composition comprising bacteria that are different from the bacteria in the probiotic composition and are desired to colonize the intestinal tract of the subject.

18. The method of claim 17, wherein the composition comprising the different bacteria that are desired to colonize the intestinal tract is a fecal matter transplant (FMT) material.

19. The method of claim 18, wherein the composition comprising the FMT material is administered to the subject before or after the administration of the probiotic composition.

20. The method of claim 19, wherein the method further comprises administering to the subject one or more of IL-10, IL-22 and hepcidin.

* * * * *